(12) United States Patent
Samizo et al.

(10) Patent No.: US 7,598,240 B2
(45) Date of Patent: Oct. 6, 2009

(54) BENZOTHIAZIN-3-ONE COMPOUND AND INTERMEDIATE THEREFOR

(75) Inventors: Fumio Samizo, Tokyo (JP); Yoshihiro Horiuchi, Tokyo (JP); Nobuhisa Fukuda, Osaka (JP); Katsunori Tsuboi, Osaka (JP); Atsushi Makita, Oita (JP)

(73) Assignee: Dainippon Sumitomo Pharma Co., Ltd., Osaka (JP)

( * ) Notice: Subject to any disclaimer, the term of this patent is extended or adjusted under 35 U.S.C. 154(b) by 284 days.

(21) Appl. No.: 10/598,516

(22) PCT Filed: Feb. 28, 2005

(86) PCT No.: PCT/JP2005/003821

§ 371 (c)(1),
(2), (4) Date: Jun. 18, 2007

(87) PCT Pub. No.: WO2005/082872

PCT Pub. Date: Sep. 9, 2005

(65) Prior Publication Data

US 2008/0058321 A1 Mar. 6, 2008

(30) Foreign Application Priority Data

Mar. 2, 2004 (JP) ............................. 2004-057808

(51) Int. Cl.
*C07D 279/16* (2006.01)
*A61K 31/5415* (2006.01)
(52) U.S. Cl. ...................... 514/224.2; 544/49
(58) Field of Classification Search ............... 544/49; 514/224.2
See application file for complete search history.

(56) References Cited

U.S. PATENT DOCUMENTS

| | | | |
|---|---|---|---|
| 3,873,555 A | 3/1975 | Bowden | |
| 3,910,904 A | 10/1975 | Worley | |
| 3,923,709 A | 12/1975 | Worley | |
| 4,584,300 A | 4/1986 | Iwao et al. | |
| 4,755,509 A | 7/1988 | Teulon | |
| 4,771,050 A | 9/1988 | Meguro et al. | |
| 5,496,817 A | 3/1996 | Kawashima et al. | |
| 6,713,477 B1 | 3/2004 | Scarlato et al. | |
| 2004/0043984 A1 | 3/2004 | O'Brien | |
| 2005/0282905 A1 | 12/2005 | Horiuchi | |

FOREIGN PATENT DOCUMENTS

| | | |
|---|---|---|
| JP | 10-84987 A | 4/1998 |
| JP | 10-120621 A | 5/1998 |
| JP | 2000-309575 A | 11/2000 |
| JP | 2002-37761 A | 2/2002 |
| JP | 2002-128769 A | 5/2002 |
| JP | 2002-542238 A | 12/2002 |
| WO | WO 96/20936 | 7/1996 |
| WO | WO 03/055851 A1 | 7/2003 |
| WO | WO 2004/014389 A1 | 2/2004 |

OTHER PUBLICATIONS

Masanobu Fujita, et al., "A Novel, Convenient Synthesis of 2-Aryl-3-oxo-3,4-dihydro-2H-1,4-benzothiazines", *Synthesis*, Aug. 1988, pp. 599-604.

J.W. Worley, et al., "2-Dialkylphosphonyl- and 2-Alkylidene-3,4-dihydro-3-oxo-2H-1,4-benzothiazines", *J. Org. Chem.*, vol. 40, No. 12, 1975, pp. 1731-1734.

Hiroyuki Tawada, et al., "Studies on Antidiabetic Agents. IX. A New Aldose Reductase Inhibitor, AD-5467, and Related 1-4-Benzoxazine and 1-4-Benzothiazine Derivatives: Synthesis and Biological Activity", *Chem. Pharm. Bull.*, vol. 38, No. 5, 1990, pp. 1238-1245.

Giuseppe Trapani, et al., "Synthesis of 2-Substituted-N-Carboxymethyl-1,5-Benzothiazepin-4-Ones and—1,4-Benzothiazin-3-Ones and their Evaluation as Angiotensin Converting Enzyme Inhibitors", *Il Farmaco*, vol. 50, No. 2, 1995, pp. 107-112.

Masahiro Kajino, et al., "Synthesis and Biological Activities of New 1,4-Benzothiazine Derivatives", *Chem. Pharm. Bull.*, vol. 39, No. 11, 1991, pp. 2888-2895.

Sarah E. Kelly and Thomas G. LaCour, "An Efficient Synthesis of (S)-2-Hexylthiodecanoic Acid", *Tetrahedron: Asymmetry*, vol. 3, No. 6, 1992, pp. 715-718.

Zhe Wang, et al., "Enantioselective Synthesis of α-Hydroxy Carboxylic Acids: Direct Conversion of α-Oxocarboxylic Acids to Enantiomerically Enriched α-Hydroxy Carboxylic Acids via Neighboring Group Control", *Tetrahedron Letters*, vol. 39, 1998, p. 5501-5504.

Yasuo Yoshihara, et al., "Matrix metalloproteinases and tissue inhibitors of metalloproteinases in synovial fluids from patients with rheumatoic arthritis or osteoarthritis", *Annals of the Rheumatic Diseases*, vol. 59, No. 6, 2000, pp. 455-461.

R. Clark Billinghurst, et al., "Enhanced Cleavage of Type II Collagen by Collagenases in Osteoarthritic Articular Cartilage", *J. Clinical Investigation*, vol. 99, No. 7, 1997, pp. 1534-1545.

(Continued)

*Primary Examiner*—Kahsay T Habte
(74) *Attorney, Agent, or Firm*—Sughrue Mion, PLLC

(57) ABSTRACT

A medicine which contains as an active ingredient a benzothiazin-3-one-compound represented by the formula (1):

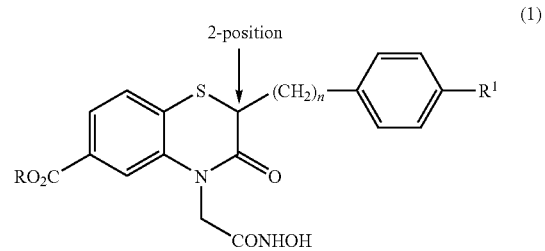

(wherein n is 3 or 4; R represents ethyl or hydrogen; and $R^1$ represents hologeno, alkoxy, haloalkyl, or haloalkoxy) or a pharmaceutically acceptable salt thereof. It is useful as a therapeutic or preventive agent for arthrosis deformans, chondrodegenerative discases such as chronic articular rheumatism, cancers, gingivitis, etc. Also provided are an intermediate for the compound and a process for producing the compound.

8 Claims, 1 Drawing Sheet

OTHER PUBLICATIONS

Yuichi Nagakawa, et al., "Histologic Features of Venous Invasion, Expression of Vascular Endothelial Growth Factor and Matrix Metalloproteinase-2 and Matrix Metalloproteinase-9, and the Relation with Liver Metastasis in Pancreatic Cancer", *Pancreas*, vol. 24, No. 2, 2002, pp. 169-178.

Francesco Sinigaglia and Juergen Hammer, "Motifs and Supermotifs for MHC Class II Binding Peptides", *J. Exp. Med.*, vol. 181, Feb. 1995, pp. 449-451.

E.M. O'Byrne, et al., "Oral administration of a matrix metalloproteinase inhibitor, CGS 27023A, protects the cartilage proteoglycan matrix in a partial meniscectomy model of osteoarthritis in rabbits", *Inflamm. Res.*, vol. 44, Supplement 2, 1995, pp. S117-S118.

A. Yamada, et al., "ONO-4817, an orally active matrix metalloproteinase inhibitor, prevents lipopolysaccharide-induced proteoglycan release from the joint cartilage in guinea pigs", *Inflamm. Res.*, vol. 49, 2000, pp. 144-146.

E.J. Lewis, et al., "Ro 32-3555, an orally active collagenase inhibitor, prevents cartilage breakdown in vitro and in vivo", *British Journal of Pharmacology*, vol. 121, 1997, pp. 540-546.

Alexander Rosemurgy, et al., "Marimastat in Patients With Advanced Pancreatic Cancer", *Am. J. Clin. Oncol. (CCT)*, vol. 22, No. 3, 1999, pp. 247-252.

M. J. Janusz, et al., "Induction of osteoarthritis in the rat by surgical tear of the meniscus: Inhibition of joint damage by a matrix metalloproteinase inhibitor", *Osteoarthritis and Cartilage*, vol. 10, 2002, pp. 785-791.

```
                        SEQUENCE LISTING

<160> NUMBER OF SEQ ID NOS: 3

<210> SEQ ID NO 1
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1 ataagcttc caccatgcat ccaggggtcc tggc                                34

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ccgctcgagt taccccaaat gctcttcagg                                    30

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: 7-methoxycoumarin-4-yl proline
<220> FEATURE:
<221> NAME/KEY: MOD_RES
<222> LOCATION: (5)
<223> OTHER INFORMATION: L-[N-(2,4-dinitrophenyl)-L-2,3-
      diaminopropionyl]-alanine

<400> SEQUENCE: 3

Xaa Leu Gly Leu Xaa Arg
1               5
```

BENZOTHIAZIN-3-ONE COMPOUND AND INTERMEDIATE THEREFOR

TECHNICAL FIELD

The present invention relates to a novel benzothiazin-3-one compound or a pharmaceutically acceptable salt thereof, which is useful as a matrix metallo-proteinase inhibitor, an intermediate for production of the compound and a process for producing the compound.

BACKGROUND ART

Extracellular matrix constituting connective tissues, represented by collagen and proteoglycan is metabolized by a group of proteases referred to as matrix metallo-proteinase (hereinafter abbreviated as MMPs in some cases). As MMPs, there are known at present 23 enzymes such as collagenase (referred to also as matrix metallo-proteinase-1 or MMP-1), gelatinase A (referred to also as matrix metallo-proteinase-2 or MMP-2), stromelysin (referred to also as matrix metallo-proteinase-3 or MMP-3), gelatinase B (referred to also as matrix metallo-proteinase-9 or MMP-9), collagenase 3 (referred to also as matrix metallo-proteinase-13 or MMP-13) and membrane-bound matrix metallo-proteinase-1 (e.g. MT1-MMP and MMP-14). The amount of the extracellular matrix in a living body is strictly controlled by endogenous inhibitors of MMPs (e.g. TIMP (tissue inhibitor of matrix metallo-proteinase)). However, when such a balance is disturbed, the enzyme activity of MMP is abnormally enhanced, resulting in various diseases accompanied by the destruction of connective tissues as symptom.

As the diseases, there are exemplified arthrosis deformans and chronic articular rheumatism which are accompanied by the destruction of articular cartilage. As MMPs which participate in arthrosis deformans and chronic articular rheumatism, there are exemplified stromelysin and collagenase 3 etc. (see Annals of the Rheumatic Diseases. 59(6):455-61 (2000) and Journal of Clinical Investigation. 99(7):1534-45 (1997)).

In addition, MMPs are enzymes capable of decomposing basement membrane and participate in the infiltration of cancerous cells into vascular endothelium from peripheral tissues, namely, cancer metastasis. As such MMPs, gelatinases A and B are exemplified (see Pancreas. 24(2):169-78 (2002)).

The therapeutic or preventive effect of MMP inhibitors on the above-exemplified diseases is revealed by J. Exp. Med., 182, 449-457 (1995), Inflamm. Res, 44, S117-S118 (1995), British J. Pharmacol., 121, 540-546 (1997), Inflamm. Res, 49, 144-146 (2000), Am. J. Clin. Oncol., 22, 247-252 (1999), Osteoarthritis and Cartilage, 10, 785-791 (2002), etc. Therefore, MMP inhibitors are considered effective as therapeutic or preventive agents for chondrodegenerative diseases (e.g. arthrosis deformans, chronic articular rheumatism), cancers, etc.

As MMP inhibitors, many compounds are known (see Exp. Opin. Ther. Patents, 8, 259-282 (1998)). There may be exemplified 2-benzylbenzothiazin-3-one compounds (International Publication No. WO00/63197 pamphlet and Japanese Patent Unexamined Publication JP-A-2002-12876).

However, an MMP inhibitor capable of exhibiting a more remarkable effect in a living body is desired even now.

On the other hand, a process for producing a benzothiazin-3-one compound is disclosed in International Publication No. WO00/63197 pamphlet and is thus well known. In addition, there have been reported a process in which an α-bromocarboxylic acid derivative is condensed with a thiophenol derivative in DMF (see Chem. Pharm. Bull., 39, 2888 (1991)) and a process in which the hydroxyl group of an α-hydroxycarboxylic acid is converted to a trifluoromethanesulfonyloxy group in acetonitrile, followed by condensing with a nucleophile in one pot (see Tetrahedron. Asymmetry, 3, 715 (1992)). However, there has been a desire for a process for efficient production of an optically active α-phenylthiocarboxylic acid derivative with little racemization.

As a process for producing an α-hydroxycarboxylic acid as an intermediate for production of the above-mentioned benzothiazin-3-one compound, there are known, for example, the process using baker's yeast disclosed in Japanese Patent Unexamined Publication JP-A-10-84987; the process of carrying out catalytic asymmetric hydrogenation which is disclosed in Japanese Patent Unexamined Publication JP-A-10-120621, with a hydantoin derivative disclosed in Japanese Patent Unexamined Publication JP-A-2000-309575; the process using Grignard reaction of a chiral epoxide compound disclosed in Japanese Patent Unexamined Publication JP-A-2000-37761; and the process using DIP-Cl and disclosed in Tetrahedron Lett., 39, 5501 (1998). However, there has been a desire for a process for producing an α-hydroxycarboxylic acid with a high optical purity in higher yield.

DISCLOSURE OF THE INVENTION

An object of the present invention is to provide a novel agent useful as, for example, a therapeutic or preventive agent for chondrodegenerative diseases (e.g. arthrosis deformans, chronic articular rheumatism), cancers, etc., an intermediate for production of the agent and a process for producing the agent.

The present inventors earnestly investigated in order to achieve the above object, and consequently found that the benzothiazin-3-one compound of the present invention exhibits an excellent pharmacological activity on an arthrosis deformans animal model when orally administered. Furthermore, the present inventors found that said compound acts as a prodrug since it is converted to a highly active carboxylic acid compound by hydrolysis of its ethoxycarbonyl group in its metabolism in a living body.

In addition, the present inventors found a process for producing an intermediate for production of the benzothiazin-3-one compound from an α-hydroxycarboxylic acid derivative in high yield, a method for optical resolution of the starting α-hydroxycarboxylic acid, and the like.

The present invention has been accomplished on the basis of the above findings.

The present invention relates to the benzothiazin-3-one compounds or pharmaceutically acceptable salts thereof, which are useful as MMP inhibitors and are described below in [1] to [22]:

[1] A benzothiazin-3-one compound represented by the formula (1):

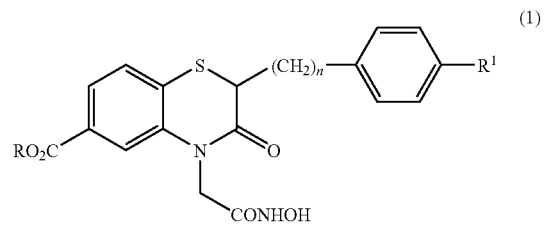

wherein n is 3 or 4; R is an ethyl group or a hydrogen atom; and $R^1$ is a halogen atom, an alkoxy group, a haloalkyl group or a haloalkoxy group, or a pharmaceutically acceptable salt thereof;

[2] A benzothiazin-3-one compound according to [1], characterized by being represented by the formula (1S):

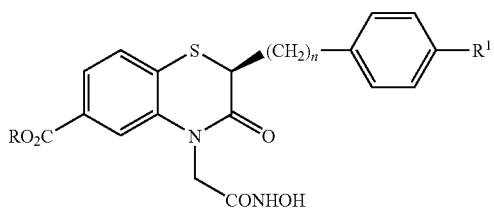

(1S)

wherein n, R and $R^1$ are as defined above, or a pharmaceutically acceptable salt thereof;

[3] A benzothiazin-3-one compound or a pharmaceutically acceptable salt thereof according to [1] or [2], wherein $R^1$ is a fluorine atom, a chlorine atom, a methoxy group, a trifluoromethyl group or a trifluoromethoxy group;

[4] A benzothiazin-3-one compound or a pharmaceutically acceptable salt thereof according to any one of [1] to [3], wherein R is an ethyl group;

[5] A benzothiazin-3-one compound or a pharmaceutically acceptable salt thereof according to any one of [1] to [3], wherein R is a hydrogen atom;

[6] A compound or a pharmaceutically acceptable salt thereof according to [4], wherein the compound represented by the formula (1) is selected from the following group of compounds: ethyl 4-[2-(hydroxyamino)-2-oxoethyl]-2-[3-(4-methoxy-phenyl)propyl]-3-oxo-3,4-dihydro-2H-1,4-benzothiazine-6-carboxylate, ethyl 2-[3-(4-chlorophenyl)propyl]-4-[2-(hydroxyamino)-2-oxoethyl]-3-oxo-3,4-dihydro-2H-1,4-benzothiazine-6-carboxylate, ethyl 2-[3-(4-fluorophenyl)propyl]-4-[2-(hydroxyamino)-2-oxoethyl]-3-oxo-3,4-dihydro-2H-1,4-benzothiazine-6-carboxylate, ethyl 4-[2-(hydroxyamino)-2-oxoethyl]-3-oxo-2-[3-(4-trifluoromethylphenyl)propyl]-3,4-dihydro-2H-1,4-benzothiazine-6-carboxylate, ethyl 4-[2-(hydroxyamino)-2-oxoethyl]-3-oxo-2-[3-(4-trifluoromethoxyphenyl)propyl]-3,4-dihydro-2H-1,4-benzothiazine-6-carboxylate and ethyl 4-[2-(hydroxyamino)-2-oxoethyl]-2-[4-(4-methoxyphenyl)butyl]-3-oxo-3,4-dihydro-2H-1,4-benzothiazine-6-carboxylate;

[7] A compound or a pharmaceutically acceptable salt thereof according to [1], wherein the compound represented by the formula (1) is (−)-ethyl 4-[2-(hydroxyamino)-2-oxoethyl]-2-[3-(4-methoxyphenyl)propyl]-3-oxo-3,4-dihydro-2H-1,4-benzothiazine-6-carboxylate;

[8] A compound or a pharmaceutically acceptable salt thereof according to [5], wherein the compound represented by the formula (1) is selected from the following group of compounds: 4-[2-(hydroxyamino)-2-oxoethyl]-2-[3-(4-methoxy-phenyl)propyl]-3-oxo-3,4-dihydro-2H-1,4-benzothiazine-6-carboxylic acid, 2-[3-(4-chlorophenyl)propyl]-4-[2-(hydroxyamino)-2-oxoethyl]-3-oxo-3,4-dihydro-2H-1,4-benzothiazine-6-carboxylic acid, 2-[3-(4-fluoro-phenyl)propyl]-4-[2-(hydroxyamino)-2-oxoethyl]-3-oxo-3,4-dihydro-2H-1,4-benzothiazine-6-carboxylic acid, 4-[2-(hydroxyamino)-2-oxoethyl]-3-oxo-2-[3-(4-trifluoromethylphenyl)propyl]-3,4-dihydro-2H-1,4-benzothiazine-6-carboxylic acid, 4-[2-(hydroxyamino)-2-oxoethyl]-3-oxo-2-[3-(4-trifluoromethoxyphenyl)propyl]-3,4-dihydro-2H-1,4-benzothiazine-6-carboxylic acid and 4-[2-(hydroxyamino)-2-oxoethyl]-2-[4-(4-methoxyphenyl)butyl]-3-oxo-3,4-dihydro-2H-1,4-benzothiazine-6-carboxylic acid;

[9] A compound or a pharmaceutically acceptable salt thereof according to [1], wherein the compound represented by the formula (1) is (−)-4-[2-(hydroxyamino)-2-oxoethyl]-2-[3-(4-methoxyphenyl)propyl]-3-oxo-3,4-dihydro-2H-1,4-benzothiazine-6-carboxylic acid.

The present invention also relates to the pharmaceutical compositions or remedies described below in [10] to [14]:

[10] A pharmaceutical composition comprising a benzothiazin-3-one compound or a pharmaceutically acceptable salt thereof according to any one of [1] to [9] as an active ingredient;

[11] A matrix metallo-proteinase inhibitor comprising a benzothiazin-3-one compound or a pharmaceutically acceptable salt thereof according to any one of [1] to [9] as an active ingredient;

[12] A remedy or prophylactic for chondro-degenerative diseases or inflammatory diseases comprising a benzothiazin-3-one compound or a pharmaceutically acceptable salt thereof according to any one of [1] to [9] as an active ingredient;

[13] A cancer metastasis suppressant comprising a benzothiazin-3-one compound or a pharmaceutically acceptable salt thereof according to any one of [1] to [9] as an active ingredient;

[14] A pharmaceutical composition for oral administration comprising a benzothiazin-3-one compound or a pharmaceutically acceptable salt thereof according to [4], [6] or [7].

In addition, the present invention relates to the intermediates for production of the compound of the formula (1) described below in [15] to [22]:

[15] A compound represented by the formula (2)

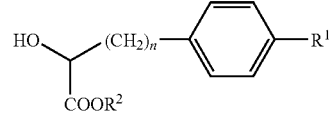

(2)

wherein n and $R^1$ are as defined in the formula (1) and $R^2$ is an alkyl group of 2 or 3 carbon atoms, a 4-nitrobenzyl group or a 2,2,2-trichloroethyl group;

[16] A compound according to [15], wherein the alkyl group of 2 or 3 carbon atoms is an ethyl group;

[17] A compound according to [15] or [16], which has an S-configuration;

[18] A compound according to [15] or [16], which has an R-configuration;

[19] A compound represented by the formula (3):

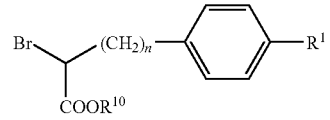

(3)

wherein n and $R^1$ are as defined in the formula (1) and $R^{10}$ is a hydrogen atom, an alkyl group of 1 to 6 carbon atoms, a 4-nitrobenzyl group or a 2,2,2-trichloroethyl group;

[20] A compound according to [19], wherein the alkyl group of 1 to 6 carbon atoms is a methyl group or an ethyl group;

[21] A compound according to [19] or [20], which has an S-configuration;

[22] A compound according to [19] or [20], which has an R-configuration.

Further, the present invention relates to the processes for producing a benzothiazin-3-one compound according to any one of [1] to [9] or an intermediate for production of the compound which are described below in [23] and [24]:

[23] A process for producing an optically active form of a compound represented by the formula (4):

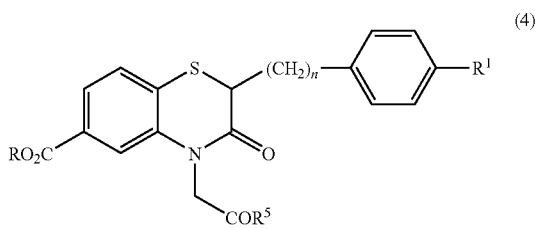

(4)

wherein n, R and $R^1$ are as defined above and $R^5$ is a hydroxyl group, an alkoxy group or a hydroxyamino group, characterized by oxidizing the compound with a Water-modified Sharpless reagent, (−)-8,8-(dichlorocamphorylsulfonyl)oxaziridine or (+)-8,8-(dichlorocamphorylsulfonyl)oxaziridine;

[24] A production process according to [23], characterized in that the oxidizing agent is (+)-8,8-(dichlorocamphorylsulfonyl)oxaziridine and that the optically active form is represented by the formula (4S):

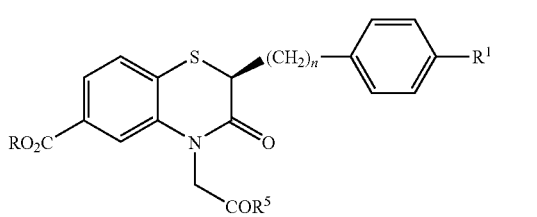

(4S)

wherein n, R, $R^1$ and $R^5$ are as defined above.

Still further, the present invention relates to the processes for producing an intermediate for production of a benzothiazin-3-one compound described in [25] and [26] and the intermediate for production described in [27]:

[25] A process for producing a compound represented by the formula (9):

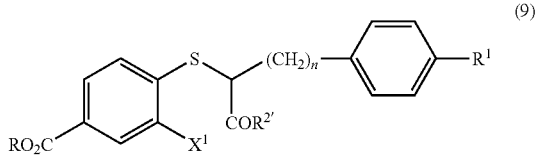

(9)

wherein n, $R^1$ and R are as defined above and $X^1$ and $R^{2'}$ are as defined below, characterized by reacting a compound represented by the formula (5):

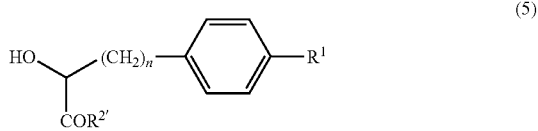

(5)

wherein n and $R^1$ are as defined above and $R^2$ is a protective group for carboxyl group or a group represented by the formula (6):

(6)

wherein $R^3$ is an alkyl group or an aryl group, with a brominating reagent or a trifluoromethanesulfonylating reagent to convert to a compound represented by the formula (7):

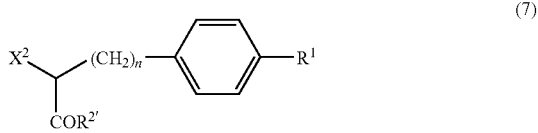

(7)

wherein n, $R^1$ and $R^{2'}$ are as defined above and $X^2$ is a bromine atom or a trifluoromethanesulfonyloxy group, and then reacting this compound with a compound represented by the formula (8):

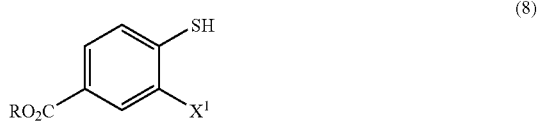

(8)

wherein $X^1$ is a halogen atom or a nitro group and R is as defined above, or a salt thereof in the presence of a base.

[26] A production process according to [25], wherein $X^1$ is a bromine atom or a nitro group and $X^2$ is a trifluoromethanesulfonyloxy group;

[27] A compound represented by the formula (3'):

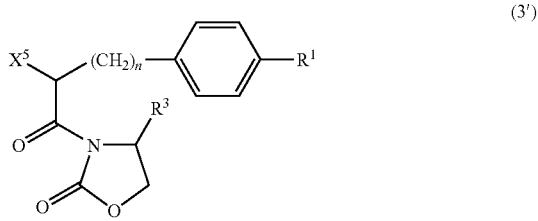

(3')

wherein n, $R^1$ and $R^3$ are as defined above and $X^5$ is a bromine atom or a hydroxyl group.

Still further, the present invention relates to the processes for producing an optically active α-hydroxycarboxylic acid described in [28] to [30]:

[28] A process for producing an optically active form of a compound represented by the formula (10):

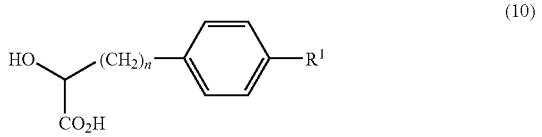

wherein n and $R^1$ are as defined above, characterized by optically resolving a racemic modification of the compound of the formula (10) by adding an optically active α-tolylethylamine to the racemic modification in an inert solvent to form diastereomers;

[29] A production process according to [28], wherein the optically active α-tolylethylamine is (−)-α-tolylethylamine and the optically active form of a compound represented by the formula (10) is a compound with an S-configuration represented by the formula (10S):

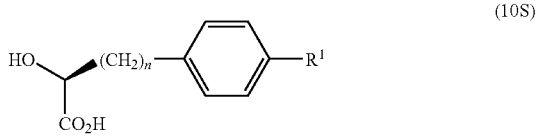

wherein n and $R^1$ are as defined in the above formula (10), or a salt thereof.

A production process according to [28], wherein the optically active α-tolylethylamine is (+)-α-tolylethylamine and the optically active form of a compound represented by the formula (10) is a compound with an R-configuration represented by the formula (10R):

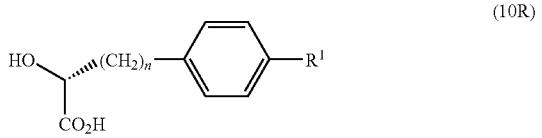

wherein n and $R^1$ are as defined in the above formula (10), or a salt thereof.

BEST MODE FOR CARRYING OUT THE INVENTION

Figure 1:
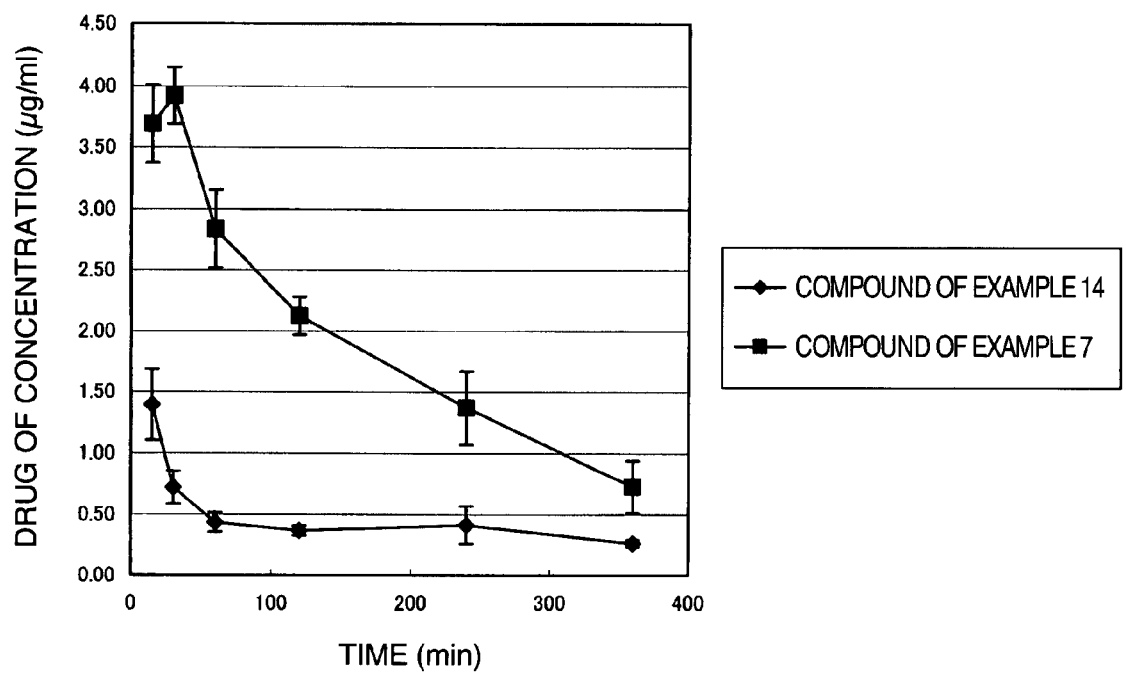
FIG. 1 is a graph showing the result of oral-absorbability evaluation test on rats.

In the present specification, the halogen atom for $R^1$ includes fluorine atom, chlorine atom, bromine atom and iodine atom. The halogen atom for $R^1$ is preferably a fluorine atom or a chlorine atom.

In the present specification, the alkoxy group for $R^1$ is a linear or branched alkoxy group of 1 to 4 carbon atoms. Specific examples thereof are methoxy group, ethoxy group, propoxy group, isopropoxy group, butoxy group, 1-methyl-1-propoxy group, 1-methyl-2-propoxy group, 2-methyl-1-propoxy group, 2-methyl-2-propoxy group, etc. The alkoxy group for $R^1$ is preferably a methoxy group.

In the present specification, the haloalkyl group for $R^1$ is a linear or branched haloalkyl group of 1 to 4 carbon atoms having 1 to 5 halogen atoms which are the same or different. Specific examples thereof are trifluoromethyl group, 2,2,2-trifluoroethyl group, 2-fluoroethyl group, etc. $R^1$ is preferably a trifluoromethyl group.

In the present specification, the haloalkoxy group for $R^1$ is a linear or branched haloalkoxy group of 1 to 4 carbon atoms having 1 to 5 halogen atoms which are the same or different. Specific examples thereof are trifluoromethoxy group, 2,2,2-trifluoroethoxy group, 2-fluoroethoxy group, etc. $R^1$ is preferably a trifluoromethoxy group.

In the present specification, the alkyl group for $R^3$ is a linear or branched alkyl group of 1 to 4 carbon atoms. Specific examples thereof are isopropyl group, isobutyl group, etc. The aryl group for $R^3$ includes phenyl group, 1-naphthyl group, 2-naphthyl group, benzyl group, etc.

A first aspect of the present invention is directed to a compound represented by the above formula (1) or a pharmaceutically acceptable salt thereof.

The compound of the formula (1) has an asymmetric carbon atom at the 2-position in its benzothiazine skeleton, and the formula (1) also represents optical isomers due to the asymmetric carbon atom. The compound of the formula (1) is preferably an optically active substance, and the configuration relating to the asymmetric carbon atom is preferably an S-configuration (in the present specification, the symbols R and S for expressing the configuration relating to the asymmetric carbon atom are used according to the IUPAC rules of organic chemistry nomenclature). Especially preferable examples of the optically active substance are (−)-ethyl 4-[2-(hydroxyamino)-2-oxoethyl]-2-[3-(4-methoxyphenyl)propyl]-3-oxo-3,4-dihydro-2H-1,4-benzothiazine-6-carboxylate and (−)-4-[2-(hydroxyamino)-2-oxoethyl]-2-[3-(4-methoxyphenyl)propyl]-3-oxo-3,4-dihydro-2H-1,4-benzothiazine-6-carboxylic acid.

The compound represented by the formula (1) of the present invention may be produced by a proper combination of a well-known process such as the process disclosed in International Publication No. WO00/63197 pamphlet, a process based thereon and the process of the present invention. Specific examples of production process of the compound are given below.

When R is an ethyl group in the formula (1), the compound may be produced according to any of the following production processes 1 to 4.

Production Process 1

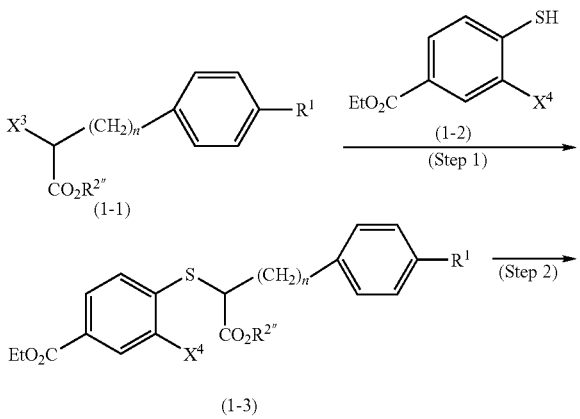

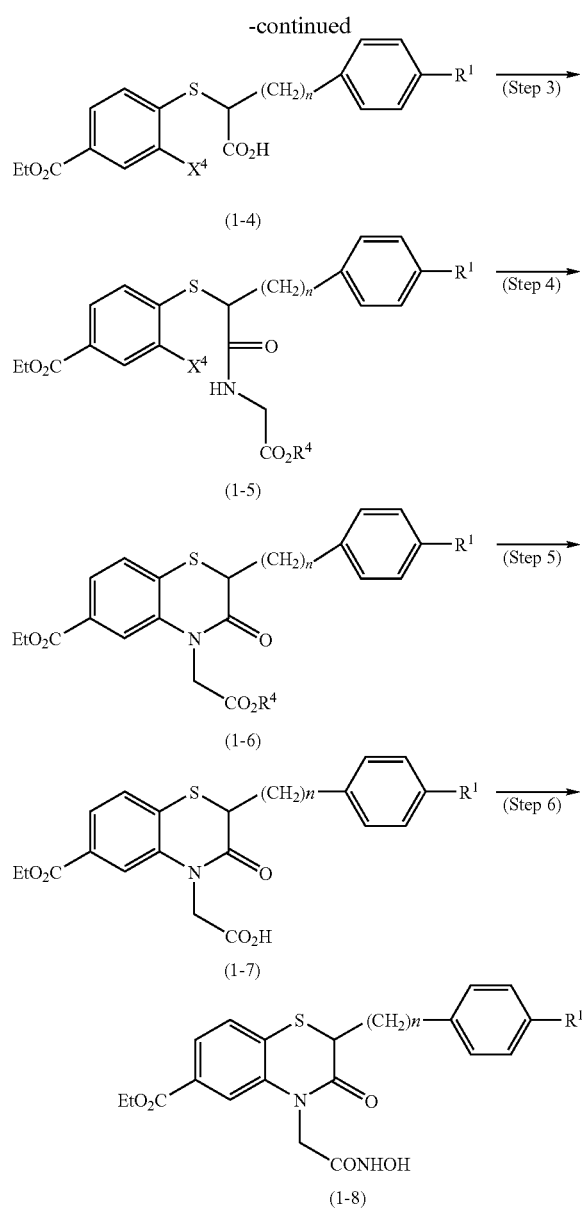

wherein n and $R^1$ are as defined above; $X^3$ and $X^4$ are independently a leaving group; and $R^{2\prime\prime}$ and $R^4$ are independently a protective group for carboxyl group.

In the production process 1, as the protective groups for carboxyl group represented by $R^{2\prime\prime}$ and $R^4$, there are exemplified protective groups which are generally used by those skilled in the art and are removable under conditions under which the ethyl ester is not hydrolyzed. Specific preferable examples thereof are protective groups such as benzyl group, p-nitrobenzyl group, p-methoxybenzyl group, tert-butyl group, etc. These protective groups are described in T. W. Green, "Protective Groups in Organic Synthesis", 3rd ed., John Wiley & Sons, Inc. (1999) (hereinafter referred to as Green reference). As the leaving groups represented by $X^3$ and $X^4$, there are exemplified halogen atoms such as bromine atom and iodine atom and sulfonyloxy groups. The sulfonyloxy groups include haloalkylsulfonyloxy groups (e.g. trifluoromethanesulfonyloxy group), alkylsulfonyloxy groups (e.g. methanesulfonyloxy group), and arylsulfonyloxy groups (e.g. p-toluenesulfonyloxy group). $X^4$ is preferably a bromine atom.

(Step 1)

A compound of the formula (1-3) may be produced by reacting a compound of the formula (1-1) with a compound of the formula (1-2) in an inert solvent such as acetonitrile or THF in the presence of a suitable base such as N-methylmorpholine or triethylamine.

(Step 2)

The protective group for carboxyl group (i.e. the group represented by $R^{2\prime\prime}$) of the compound of the formula (1-3) may be removed under conditions under which the ethyl ester is not hydrolyzed and which are employed in the method described in the above-mentioned "Green reference" and the like. For example, when $R^{2\prime\prime}$ is a p-nitrobenzyl group, a compound of the formula (1-4) may be produced by reacting the compound of the formula (1-3) with a metal such as iron or zinc without a solvent or in a hydrophilic solvent such as THF in the presence of an acid such as acetic acid or ammonium chloride.

(Step 3)

A compound of the formula (1-5) may be produced by reacting the compound of the formula (1-4) with a glycine ester in an inert solvent such as methylene chloride in the presence of a base such as triethylamine by the use of a condensing agent such as N,N'-dicyclohexylcarbodiimide (DCC), 1-ethyl-3-(3'-dimethylaminopropyl)carbodiimide (EDC) or carbonyl diimidazole (CDI). In this case, if necessary, an activator may be added. The activator includes, for example, N-hydroxybenzotriazole (HOBt) and N-hydroxysuccinimide (HOSu).

(Step 4)

A benzothiazin-3-one compound of the formula (1-6) may be produced by adding a metal catalyst and a ligand therefor to the compound of the formula (1-5) in an inert solvent such as toluene in the presence of a base such as cesium carbonate to subject the compound of the formula (1-5) to intramolecular amidation. This procedure may be carried out according to, for example, the method described in Buchwald et al., J. Am. Chem. Soc., Vol. 119, p 8451-8458 (1997). Specific examples of the metal catalyst are tris(dibenzylideneacetone)palladium(0), tetrakis(triphenylphosphine)palladium(0), etc. The ligand includes, for example, 1,1'-bis(diphenylphosphino)ferrocene (dppf) and tris(o-tolylphosphine). An especially preferable example of the ligand is dppf.

The inert solvent used here is not particularly limited. For example, toluene may be used as the inert solvent. The inert solvent may be used in a volume of 10 to 50 ml, preferably 30 ml to 40 ml, per g of the starting material. Although the reaction temperature is not particularly limited, the reaction is usually carried out at 60° C. to 120° C. The reaction time may be properly controlled by taking the disappearance of the starting material as an indication and is usually 3 hours to 8 hours.

(Step 5)

A compound of the formula (1-7) may be produced by a method properly chosen depending on the kind of ester portion of the compound of the formula (1-6). As the method, there is exemplified the method described in R. C. Ralock, "Comprehensive Organic Transformations", 2nd ed., VCH Publications Inc., New York (1999) (hereinafter referred to as Ralock reference). For example, when $R^4$ is a tert-butyl group, an acid such as trifluoroacetic acid or hydrochloric acid may be used optionally in the presence of a scavenger such as dimethyl sulfide, anisole or water, or a Lewis acid such as boron trichloride may be used in an aprotic solvent such as methylene chloride optionally in the presence of a sulfide compound such as dimethyl sulfide. When $R^4$ is a benzyl group, the compound of the formula (1-6) may be hydrogenated in an inert solvent such as ethanol in the presence of a catalyst such as palladium-carbon. When $R^4$ is a p-nitrobenzyl group, the same method as the above method adopted in the case of $R^4$ being a benzyl group may be adopted, or reduction may be carried out in acetic acid in the presence of zinc or iron.

(Step 6)

After the activation of the carboxyl group of the compound of the formula (1-7), the resulting compound is reacted with hydroxylamine or a hydroxylamine derivative, whereby the compound of the formula (1-7) may be converted to a compound of the formula (1-8) corresponding to the formula (1) in which R is an ethyl group. As a method for the activation of the carboxyl group, an amide linkage formation reaction generally used by those skilled in the art is exemplified. This method is described, for example, in "Ralock reference" or Nobuo Izumiya et al., "Fundamentals and Practice of Peptide Synthesis", Maruzen Co., Ltd., 1985. Specific examples of the method are an acid chloride method using pivaloyl chloride or the like; a mixed acid anhydride method using an alkyl chloroformate; an active ester method using a pentafluorophenyl ester or the like; and the like. After the carboxyl group is activated by such a method, the resulting compound may be reacted with hydroxylamine or a hydroxylamine derivative. The compound of the formula (1-8) corresponding to the formula (1) in which R is an ethyl group may be produced, for example, by treating the compound of the formula (1-7) with isobutyl chloroformate in an inert solvent such as THF in the presence of a base such as N-methylmorpholine, and reacting the thus treated compound with a reagent such as O-trimethylsilylhydroxylamine, followed by desilylation of the resulting product with an acid such as dilute hydrochloric acid.

The compound of the formula (1-1) as an intermediate for production of the compound of the formula (1) is novel in itself.

The compound of the formula (1-1) may be produced, for example, by the following process:

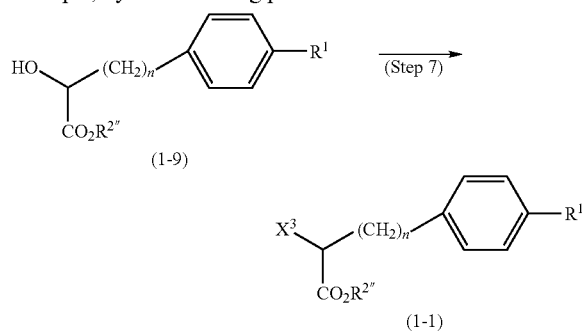

wherein n, $R^1$, $R^{2''}$ and $X^3$ are as defined above.

That is, when $X^3$ is a sulfonyloxy group, the compound of the formula (1-1) may be produced by reacting a compound of the formula (1-9) with sulfonic acid anhydride or sulfonyl chloride in an inert solvent such as acetonitrile, methylene chloride or THF in the presence of a base such as triethylamine.

On the other hand, when $X^3$ is a bromine atom, the compound of the formula (1-1) may be produced by reacting a compound of the formula (1-9) with carbon tetrabromide and triphenylphosphine. The compound of the formula (1-1) may be produced also by reacting a compound of the formula (1-9) with thionyl bromide or phosphorus tribromide. In addition, when $X^3$ is a bromine atom, the compound of the formula (1-1) may be produced also by the following process:

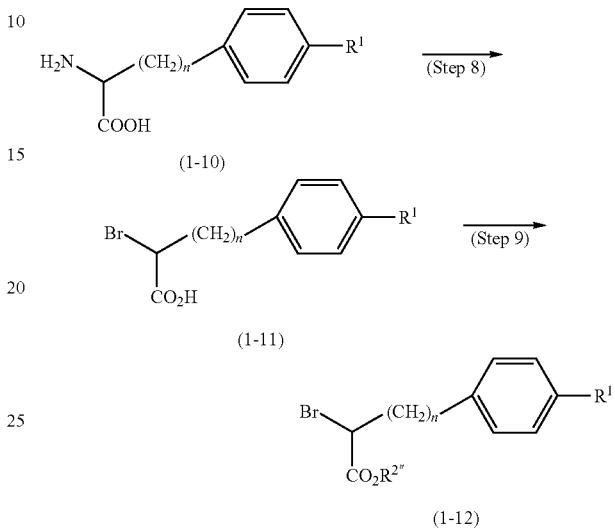

wherein n, $R^1$ and $R^{2''}$ are as defined above.

That is, a compound of the formula (1-10) is diazotized with sodium nitrite in an acidic aqueous solution (e.g. an aqueous hydrogen chloride solution, an aqueous hydrogen bromide solution or an aqueous sulfuric acid solution), an organic acid solvent (e.g. acetic acid) or a mixture of the aforesaid organic acid solvent and an inert organic solvent such as toluene, dioxane, THF, or the like, and then the diazotized compound is treated with an aqueous potassium bromide, sodium bromide or lithium bromide solution or the like, whereby the compound of the formula (1-10) may be converted to a compound of the formula (1-11). The compound of the formula (1-11) may be converted to a compound of the formula (1-12) by esterification according to a method well known to those skilled in the art. This method is described in International Publication No. WO00/63197 pamphlet, Synthesis, 583 (1999), or Tetrahedron Letters, 28, 1993 (1987).

The compound of the formula (1-1) may be produced also by the well-known process described in Tetrahedron Asymmetry, 6, 1919 (1995).

The compound of the formula (1-10) is a well-known compound and may be prepared by a process well known to those skilled in the art. Specifically, it may be synthesized by the process described in Tetrahedron, 58, 6117 (2002).

The compound of the formula (1-9) may be produced, for example, by a well-known process or the process described in the working example in the present specification. A process for producing an optically active form of the compound of the formula (1-9) is explained in the production process 6 or 7 hereinafter described, or the like.

The above-mentioned compound of the formula (1-6) may be produced according to the following production process 2.

Production Process 2

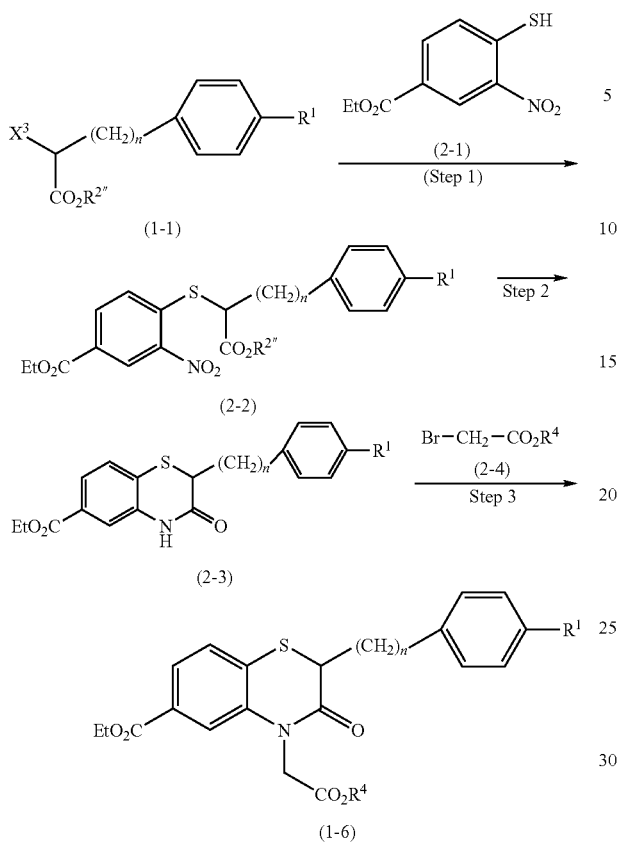

A compound of the formula (3-3) corresponding to a compound of the formula (1) in which R is a hydrogen atom may be produced according to the following production process 3.

Production Process 3

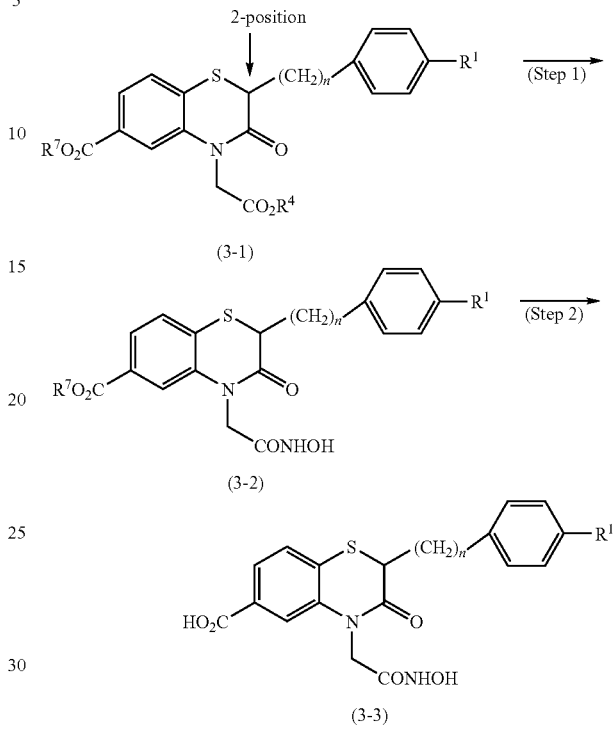

wherein n, $R^1$, $R^{2''}$, $R^4$ and $X^3$ are as defined above.

Here, as the leaving group represented by $X^3$, there are exemplified halogen atoms such as bromine atom, iodine atom, etc.; and sulfonyloxy groups such as trifluoromethanesulfonyloxy group, methanesulfonyloxy group, etc.

(Step 1)

A compound of the formula (2-2) may be produced by reacting a compound of the formula (1-1) with a compound of the formula (2-1) in an inert solvent such as THF in the presence of a suitable base such as N-methylmorpholine or triethylamine.

(Step 2)

A compound of the formula (2-3) may be produced by reacting the compound of the formula (2-2) with iron or zinc without a solvent or in a solvent such as toluene in the presence of acetic acid or ammonium chloride to carry out cyclization. In the production process 2, as the protective group for carboxyl group represented by $R^{2''}$, protective groups generally used by those skilled in the art are exemplified. Specifically, protective groups such as methyl group, ethyl group, p-nitrobenzyl group and the like are suitable.

(Step 3)

The compound of the formula (1-6) may be produced by reacting the compound of the formula (2-3) with a compound of the formula (2-4) in an inert solvent such as dimethylformamide in the presence of a base such as cesium carbonate, potassium carbonate or sodium hydride.

The compound of the formula (1-6) may be converted to the compound of the formula (1-8) by the method described in the above-mentioned production process 1.

wherein $R^1$, $R^4$ and n are as defined above, and $R^7$ is a protective group for carboxyl group.

(Step 1)

A compound of the formula (3-2) may be produced by selectively removing $R^4$ of a compound of the formula (3-1) and by a method similar to the method described in the step 2 or step 5 in the above-mentioned production process 1. Here, a combination of the protective groups represented by $R^4$ and $R^7$ may be any combination so long as it permits choice of conditions under which $R^7$ is not removed simultaneously with the removal of $R^4$. There are used, for example, a combination of an ethyl ester and a (substituted) benzyl ester, a combination of an ethyl ester and a tert-butyl ester, a combination of a (substituted) benzyl ester and a tert-butyl ester, and a combination of a 2,2,2-trichloroethyl ester and a tert-butyl ester. A combination of p-nitrobenzyl ester and a tert-butyl ester, a combination of a benzyl ester and a tert-butyl ester, a combination of a 2,2,2-trichloroethyl ester and a tert-butyl ester, and the like are suitable. Reference to "Green reference" is sufficient to determine conditions for the protection and deprotection in the case of each protective group.

The compound of the formula (3-1) may be produced in the same manner as in the production process 1.

(Step 2)

The compound of the formula (3-3) may be produced by converting the ester portion of the compound of the formula (3-2) to a carboxyl group by deprotection reaction. When $R^7$ is an alkyl group such as ethyl group, the compound of the formula (3-2) may be hydrolyzed with an alkaline aqueous solution in an alcohol solvent such as ethanol. As the alkaline aqueous solution, there are exemplified an aqueous lithium hydroxide solution, an aqueous potassium hydroxide solution, an aqueous sodium hydroxide solution, an aqueous cesium hydroxide solution and an aqueous barium hydroxide solution. Preferable examples thereof are an aqueous lithium hydroxide solution, an aqueous potassium hydroxide solution and an aqueous sodium hydroxide solution.

When the compound of the formula (3-2) is an optically active substance synthesized by the production process described hereinafter or the like, racemization proceeds under conditions of, for example, the above-mentioned hydrolysis with the alkaline aqueous solution, so that the optical purity of the compound of the formula (3-3) is remarkably decreased in some cases. As a method for avoiding the progress of the racemization, there is exemplified a method of adding a 1% to 50% alkaline aqueous solution at a low temperature in 5 mM to 5M tetrahydrofuran solvent. The reaction temperature is, for example, −25° C. to 15° C., preferably −20° C. to 5° C., more preferably −15° C. to −5° C. Preferable examples of the alkaline aqueous solution are an aqueous potassium hydroxide solution and an aqueous sodium hydroxide solution. The number of equivalents of the alkali metal salt added is, for example, 1 to 10 equivalents, preferably 2 to 5 equivalents, more preferably 2 to 3 equivalents.

It is also possible to produce the compound of the formula (3-3) while keeping the optical purity of the compound of the formula (3-2) as starting material, by hydrolyzing the compound of the formula (3-2) with a hydrolase well known to those skilled in the art, such as lipase or esterase.

The intermediate for production such as the compound of the formula (1-3) as intermediate for production in the production process 1, the compound of the formula (2-2) as intermediate for production in the production process 2, or a compound of the formula (5-7) as intermediate for production in the production process 6 described hereinafter may be produced according to the following production process 4. A production process of a compound of the formula (9) based on the production process 4 is also within the scope of the present invention.

Production Process 4

A process for producing a compound of the formula (9) as intermediate for production of a benzothiazin-3-one compound such as a compound of the formula (1) is explained below in detail.

(Step 1)

A compound of the formula (5) as starting material may be produced by the above-mentioned production process and the process described in the working example in the present specification.

In the formula (5), formula (7) and formula (9), n is preferably 3 or 4.

A compound of the formula (7) may be produced from the compound of the formula (5) by the following process:

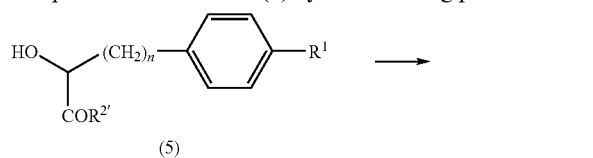

(5)

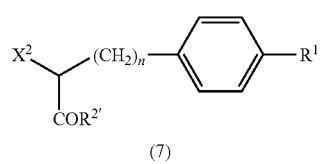

(7)

wherein n, $R^1$, $R^{2\prime}$ and $X^2$ are as defined above.

That is, when $X^2$ is a trifluoromethanesulfonyloxy group, the compound of the formula (7) may be produced by reacting the compound of the formula (5) with trifluoromethanesulfonic acid anhydride as trifluoromethanesulfonylating reagent in an inert solvent in the presence of a base represented by organic amines such as triethylamine, N-methylmorpholine, etc. The base may be used usually in an amount of 1.0 mole to 1.2 moles per mole of the starting material.

In the production process 4, preferable examples of $R^{2\prime}$ are alkoxy groups of 1 to 6 carbon atoms, 4-nitrobenzyloxy group and 2,2,2-trichloroethoxy group. Preferable examples of the aforesaid alkoxy groups are alkoxy groups of 2 or 3 carbon atoms.

Here, although the inert solvent is not particularly limited, acetonitrile, methylene chloride, THF and the like are preferably usable as the inert solvent. A more preferable inert solvent is acetonitrile. The inert solvent may be used in a volume of 3 ml to 5 ml per g of the starting material. Although the reaction temperature is not particularly limited, the reaction is usually carried out at −30° C. to −5° C. The reaction time may be properly controlled by monitoring the disappearance of the starting material and takes usually 0.5 hour to 2 hours.

On the other hand, when $X^2$ is a bromine atom, the compound of the formula (7) may be produced, for example, by the process described in the above-mentioned production process 1, i.e., the process using triphenylphosphine and carbon tetrabromide as brominating agents.

When $X^2$ is a bromine atom, a well-known compound of the formula (4-1) (see Helvetica Chimica Acta, 40, 1812 (1957)) may be brominated with a brominating agent such as N-bromosuccinimide as follows after converting the hydrogen atom on the α carbon atom of the compound to a silyl enol ether by the use of a base such as LDA and a silylating agent such as trimethylsilyl chloride (Tetrahedron Asymmetry, 6 1919 (1995)):

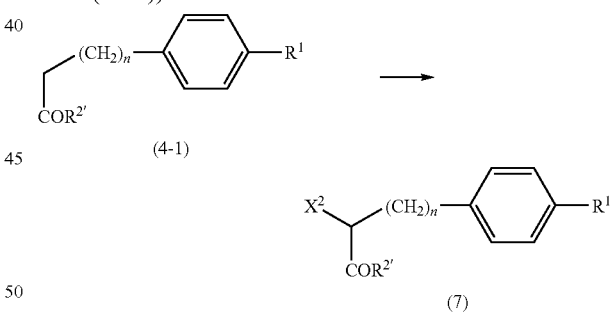

(4-1)

(7)

wherein n, $R^1$, $R^{2\prime}$ and $X^2$ are as defined above.

(Step 2)

The compound of the formula (9) may be produced by condensing the compound of the formula (7) with a compound of the formula (8) in an inert solvent in the presence of a base:

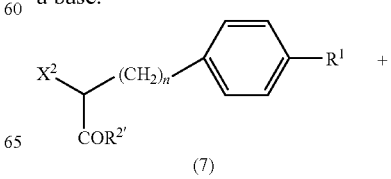

(7)

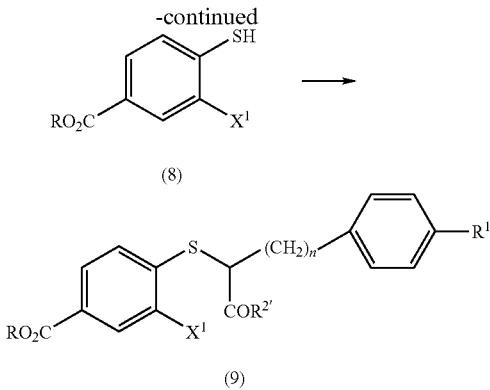

(8)

(9)

wherein n, $R^1$, $R^{2'}$, R, $X^1$ and $X^2$ are as defined above.

When $X^2$ is a trifluoromethanesulfonyloxy group, the inert solvent is not particularly limited. Preferable examples of the inert solvent are acetonitrile, methylene chloride and THF. A more preferable example thereof is THF. Here, the step 2 may be carried out in the same system as in the step 1 without isolating the product obtained in the step 1, i.e., the compound of the formula (7).

When the compound of the formula (5) and the compound of the formula (7) are optically active substances, employment of DMF or acetonitrile causes partial racemization. However, it was found that employment of THF makes it possible to produce the compound of the formula (9) with a high optical purity in high yield without racemization.

The inert solvent may be used in a volume of 2 ml to 10 ml per g of the starting material. As the base, there are exemplified organic amines such as N-methylmorpholine, triethylamine, etc. The base may be used usually in an amount of 1.0 mole to 1.2 moles per mole of the starting material.

The compound of the formula (8) may be used usually in an amount of 1.0 mole to 1.2 moles per mole of the starting material. Although the reaction temperature is not particularly limited, the reaction is usually carried out at −50° C. to 5° C., preferably −20° C. to 0° C. The reaction time may be properly controlled by monitoring the disappearance of the starting material and takes usually 0.5 hour to 2 hours.

On the other hand, also when $X^2$ is a bromine atom, the compound of the formula (9) may be produced by the same process as above.

The compound of the formula (8) may be produced by a process well known to those skilled in the art. A specific example of the process is the process described in the working example in the present specification.

The above-mentioned compounds of the formula (2) and the formula (3) as intermediates for production of the compound of the formula (1) are novel compounds in themselves.

That is, the compound of the formula (2):

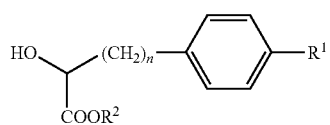

(2)

wherein n, $R^1$ and $R^2$ are as defined above, and the compound of the following formula (3):

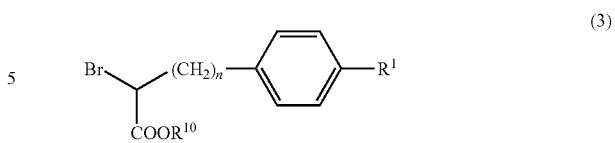

(3)

wherein n and $R^1$ are as defined in the formula (1) and $R^{10}$ is a hydrogen atom, an alkyl group of 1 to 6 carbon atoms, a 4-nitrobenzyl group or a 2,2,2-trichloroethyl group, are within the scope of the present invention.

Here, $R^1$ in the formula (2) and the formula (3) is preferably a methoxy group. As the alkyl groups of 2 or 3 carbon atoms for $R^2$ in the formula (2), ethyl group, propyl group and isopropyl group are exemplified.

The alkyl group of 1 to 6 carbon atoms for $R^{10}$ in the formula (3) is a linear or branched alkyl group. Specific examples thereof are methyl group, ethyl group, propyl group, 1-methylethyl group, butyl group, 1-methylpropyl group, 1,1-dimethylethyl group, pentyl group, hexyl group, etc. $R^{10}$ is preferably an alkyl group of 1 to 3 carbon atoms, more preferably a methyl group or an ethyl group.

The compounds of the formula (2) and formula (3) are compounds having an asymmetric carbon atom, and the present invention includes both a mixture of optically active forms of each compound (a racemic modification) and these optically active substances.

The optically active form of each compound may be produced by the process described hereinafter, and by the use of such an optically active substance, an optically active compound of the formula (1) and an intermediate for production of this compound may be produced.

The compound of the formula (1) or a pharmaceutically acceptable salt thereof may be in the form of a solvate. The solvent in the solvate includes, for example, alcohols such as methanol, ethanol, propanol, isopropanol, etc.; ketones such as acetone, etc.; ethers such as tetrahydrofuran, dioxane, etc.; and water. Although the amount of the solvent per molecule of the compound of the formula (1) is not particularly limited, the solvate is, for example, one containing 0 to 3 molecules (specifically ½ molecule, 1 molecule, 2 molecules or 3 molecules) of the solvent.

The compound of the formula (1) and an intermediate for production of this compound may be purified by a method well known to those skilled in the art. They may be purified, for example, by any of various normal-phase or reversed-phase column chromatographies using silica gel, an ion-exchange resin, molecular sieve or the like, high performance liquid chromatography (HPLC) or recrystallization. A solvent for the recrystallization includes, for example, alcohol solvents such as methanol, ethanol, 2-propanol, etc.; aprotic solvents such as dimethylformamide, dimethyl sulfoxide, etc.; ether solvents such as diethyl ether, etc.; ester solvents such as ethyl acetate, etc.; aromatic hydrocarbon solvents such as toluene, etc.; ketone solvents such as acetone, etc.; hydrocarbon solvents such as hexane, etc.; halogenated hydrocarbon solvents such as chloroform, dichloroethane, etc.; and mixed solvents thereof.

The compound of the formula (1) may be converted to a pharmaceutically acceptable salt as follows. As the pharmaceutically acceptable salt, base addition salts are exemplified. The base addition salts include inorganic base salts such as sodium salt, potassium salt, cesium salt, ammonium salt, etc.;

and organic base salts such as meglumine salt, tris(hydroxymethyl)aminomethane salt, triethylamine salt, lysine salt, etc.

The compound of the formula (1) is a compound having an asymmetric carbon atom, and the present invention includes both a mixture of optically active forms of the compound (a racemic modification) and these optically active substances. When the compound of the formula (1) or an intermediate for production of this compound is a racemic modification, the racemic modification may be resolved into optically active substances by the method described hereinafter in the present specification. Thus, the optically active substance may be produced according to the any of above-mentioned production processes 1 to 3. The optically active form of the compound of the formula (1) may be produced by using the optically active form of the intermediate for production of the formula (1-1) described hereinafter.

An optically active form of each of the compound of the formula (1) and an intermediate for production of this compound is preferably producible by any of the production processes described as the following production processes 5 to 8. That is, the production processes of optically active forms of the compound of the formula (1), a pharmaceutically acceptable salt thereof and an intermediate for production of the compound described as the production process 5 to 8 are also within the scope of the present invention.

An intermediate for production of the compound of the formula (1) represented by the formula (4) may be optically resolved by adopting the following production process 5.

Production Process 5

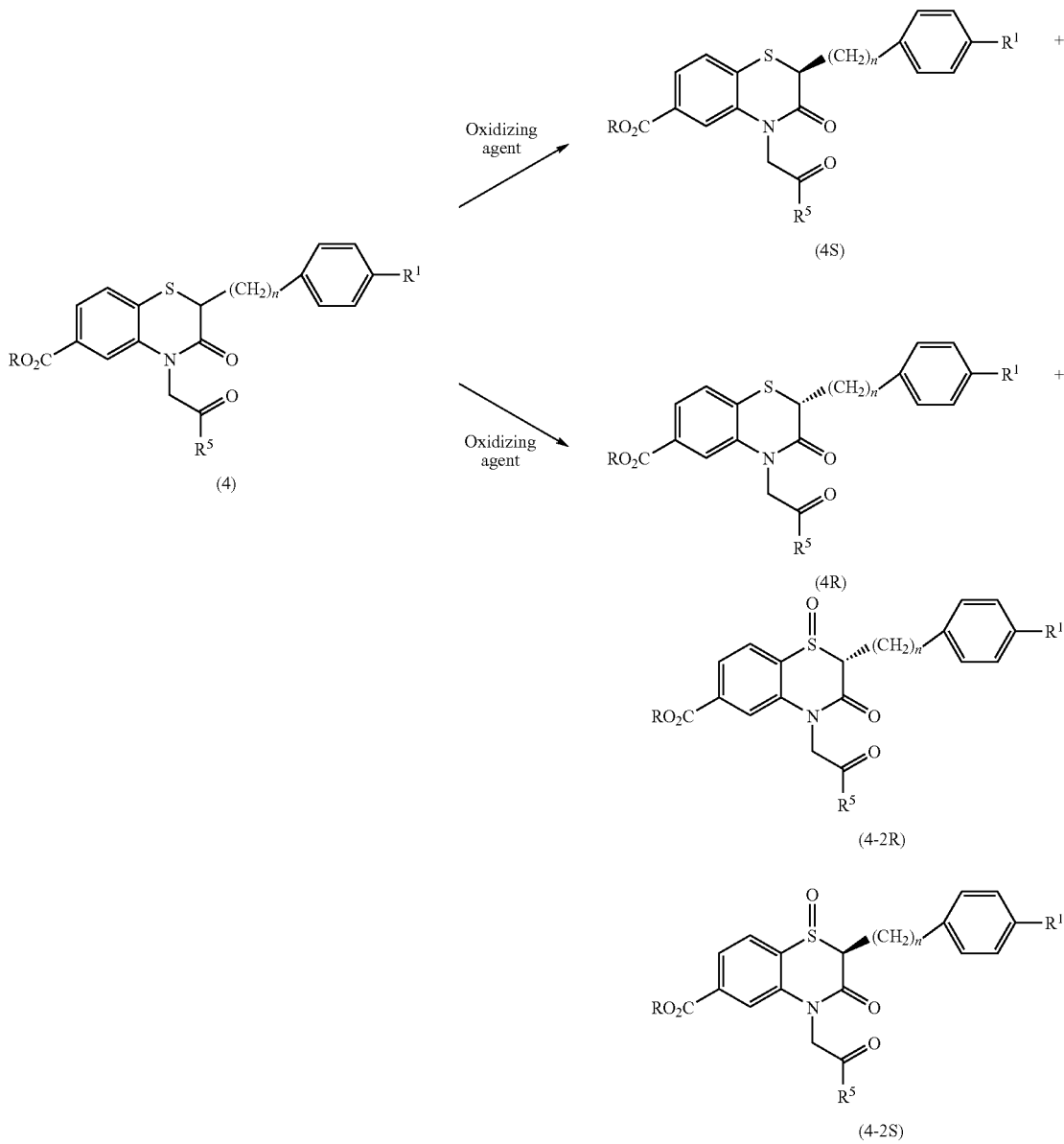

wherein n, R, R¹ and R⁵ are as defined above.

In the production process 5, the alkoxy group for $R^5$ is not particularly limited so long as it is an alkoxy group used as a protective group for carboxyl group. Specific examples thereof are tert-butoxy group, benzyloxy group, etc.

A racemic modification of the compound of the formula (4) [corresponding to the compound of the formula (1) or an intermediate for production of this compound] may be optically resolved by selective oxidization of one of the optical isomers by treating the racemic modification with an optically active oxidizing agent in an inert solvent. As the oxidizing agent used here, there are exemplified the Water-modified Sharpless reagent described in Tetrahedron Asymmetry, 8, 13, 2109-2114 (1997), i.e., a mixture of (+)- or (−)-diisopropyl tartrate, titanium tetraisopropoxide, t-butyl hydroperoxide, a small volume of water and molecular sieve (4A); and the N-sulfonyloxaziridine reagent described in J. Org. Chem., 57, 7274 (1992).

A specific example of the optically active oxidizing agent is (+)-(8,8-dichlorocamphorylsulfonyl)oxaziridine. In this case, an S-form of the compound of the formula (1) represented by the formula (4S) is selectively obtainable. On the other hand, an R-form of the compound of the formula (1) represented by the formula (4R) is selectively obtainable by using (−)-(8,8-dichlorocamphorylsulfonyl)oxaziridine as the oxidizing agent.

When R is an ethyl group and $R^5$ is an NHOH group or an O-tert-butyl group, the compound may be efficiently optical resolved by treating the racemic modification with 2 equivalents of the optically active oxidizing agent in methylene chloride. On the other hand, when R is a hydrogen atom and $R^5$ is an NHOH group, the compound may be efficiently optical resolved by treating the racemic modification with 5 equivalents of the optically active oxidizing agent in ethyl acetate.

The inert solvent used here is not particularly limited. For example, acetonitrile, methylene chloride and ethyl acetate may be used as the inert solvent. The amount of the inert solvent is not particularly limited so long as the whole starting material is soluble in the inert solvent. Although the reaction temperature is not particularly limited, the reaction is usually carried out at 0° C. to 30° C. The reaction time may be properly controlled by monitoring the disappearance rate of the starting material and takes usually 1 hour to 10 days.

The compound of the formula (4) may be regenerated by reducing a compound of the formula (4-2R) or (4-2S) obtained by the above production process 5, with titanium tetraiodide. This reaction is described in Synlett, 2000, 10, 1437-1438.

A compound of the formula (5-5), an optically active form of an intermediate for production of the compound of the formula (1) may be produced by the following production process 6.

Production Process 6

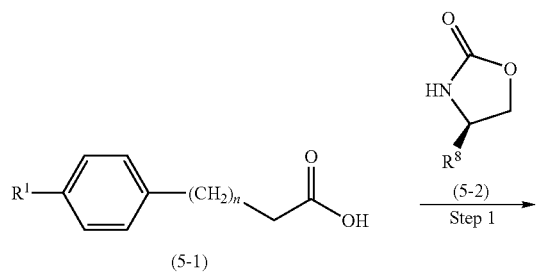

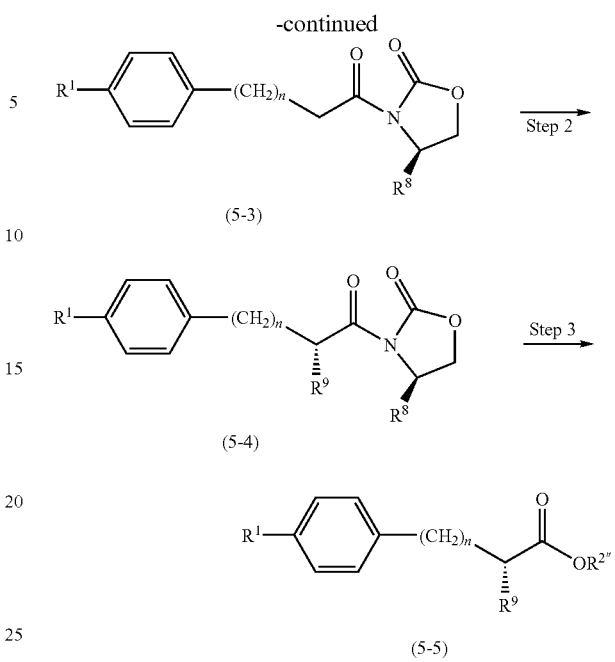

wherein n, $R^1$ and $R^{2''}$ are as defined above; $R^8$ is an isopropyl group, an isobutyl group, a phenyl group, a 1-naphthyl group, a 2-naphthyl group or a benzyl group; and $R^9$ is a bromine atom or a hydroxyl group.

In the step 1 in the above reaction scheme, a compound of the formula (5-3) may be obtained by condensing a compound of the formula (5-1) with a compound of the formula (5-2) by a method well known to those skilled in the art. That is, the compound of the formula (5-1) is converted to an acid chloride by treatment with oxalyl chloride and then the acid chloride may be reacted with the compound of the formula (5-2) (a commercial product). The above procedure is described in Tetrahedron Lett., 38, 3853 (1997).

In the step 2, a compound of the formula (5-4) may be obtained by treating the compound of the formula (5-3) with an oxidizing agent or a brominating agent in an inert solvent.

That is, when $R^9$ is a hydroxyl group in the formula (5-4), Davis reagent may be used in an inert solvent in the presence of a strong base. In this case, $R^8$ is preferably a phenyl group. As the strong base used here, sodium hexamethyldisilazide is exemplified. As the inert solvent, THF and the like may be used. The amount of the inert solvent is not particularly limited so long as the whole starting material is soluble in the inert solvent. The inert solvent may be used, for example, in a volume of 5 ml to 40 ml per g of the starting material. Although the reaction temperature is not particularly limited, the reaction is usually carried out at −78° C. to 0° C., preferably at −78° C. The reaction time may be properly controlled by monitoring the disappearance of the starting material and takes usually 1 hour to 5 hours.

On the other hand, when $R^9$ is a bromine atom in the formula (5-4), the compound of the formula (5-3) may be brominated with N-bromosuccinimide as brominating agent after treatment with dibutylboron triflate and diisopropylethylamine. In this case, $R^8$ is preferably a benzyl group or an isopropyl group.

The inert solvent used here is not particularly limited. For example, methylene chloride may be used as the inert solvent. The amount of the inert solvent is not particularly limited so long as the whole starting material is soluble in the inert solvent. The inert solvent may be used, for example, in a volume of 10 ml to 50 ml per g of the starting material. Although the reaction temperature is not particularly limited, the reaction is usually carried out at −78° C. to 0° C., preferably at −78° C. The reaction time may be properly controlled by monitoring the disappearance of the starting material and takes usually 1 hour to 5 hours.

In the step 3, the compound of the formula (5-5) may be obtained by treating the compound of the formula (5-4) with a metal alkoxide. For example, when $R^{2''}$ is a methyl group, sodium methoxide, potassium methoxide or the like may be used in methanol.

When $R^9$ is a bromine atom in the compound of the formula (5-4), a benzothiazine compound as intermediate for production of the compound of the formula (1) may be obtained according to the following reaction scheme:

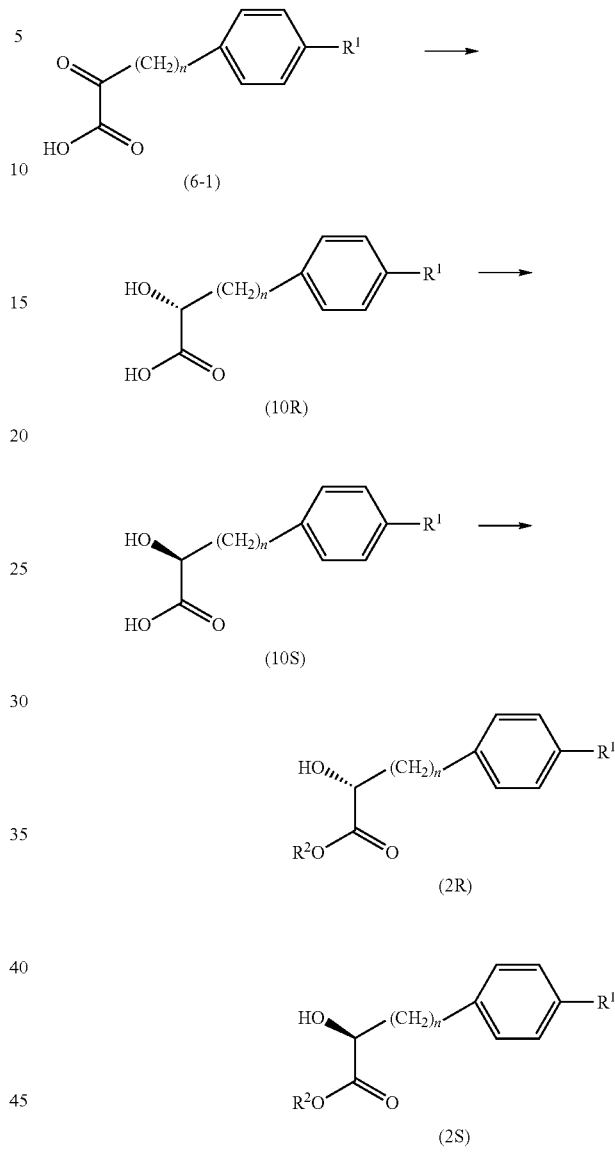

wherein n, $R^1$ and $R^8$ are as defined above.

That is, the step 4 and the step 5 may be carried out in the same manner as in the step 1 and step 2 in the above-mentioned production process 2.

An optically active form of the compound of the formula (2) may be produced by the following production process 7 (see Tetrahedron Lett., 39, 5501 (1998)).

Production Process 7

The optically active form may be produced by treating a compound of the formula (6-1) with an optically active reducing agent such as (+)- or (−)-diisopinocampheylborane chloride (DIP-Cl), and then reacting the treated compound with an alcohol in the presence of an acid such as sulfuric acid to esterify the carboxyl group.

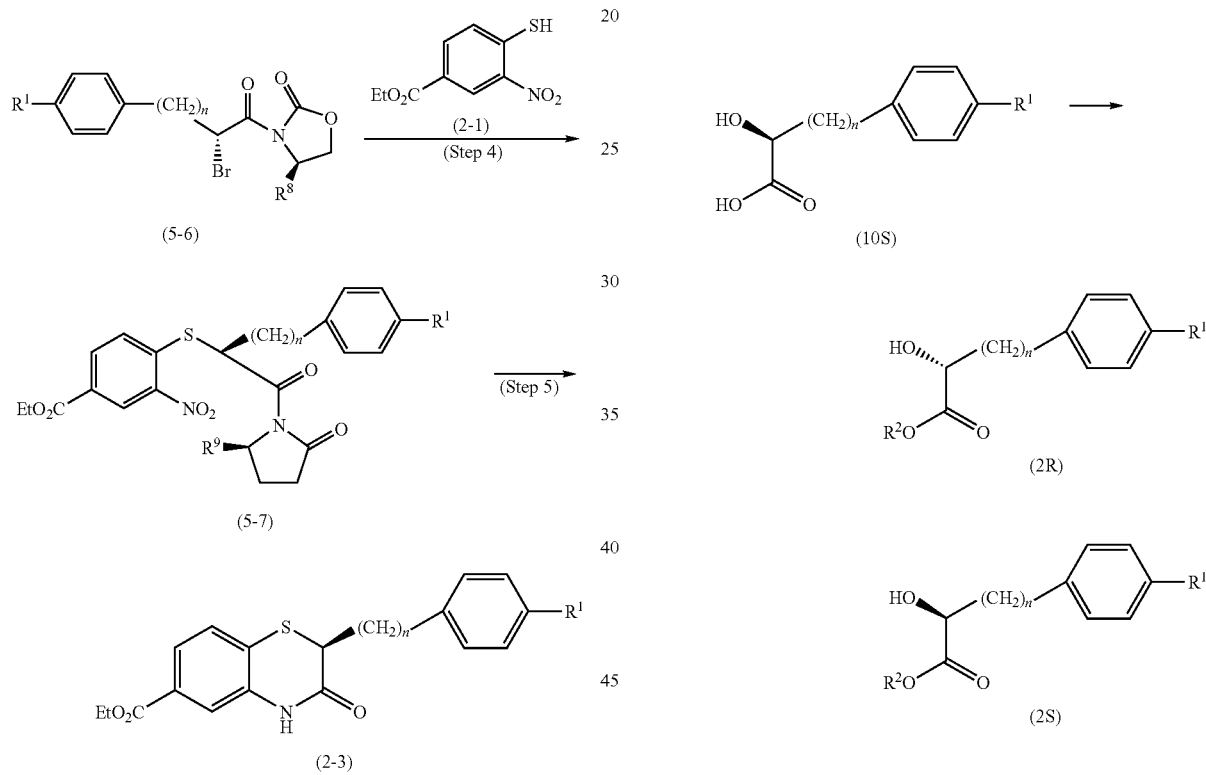

wherein n, $R^1$ and $R^2$ are as defined above.

Specifically, an (S) form of the formula (10S) may be produced by treating the compound of the formula (6-1) with (+)-diisopinocampheylborane chloride, and an (R) form of the formula (10R) may be produced by treating the compound of the formula (6-1) with (−)-diisopinocampheylborane chloride.

The compound of the formula (10R) or (10S) may be converted to, for example, an optically active substance of the formula (2R) or (2S) by esterification by a well-known method.

An optically active form of α-hydroxycarboxylic acid as intermediate for production of the compound of the formula (2) may be produced by the following production process 8.

Production Process 8

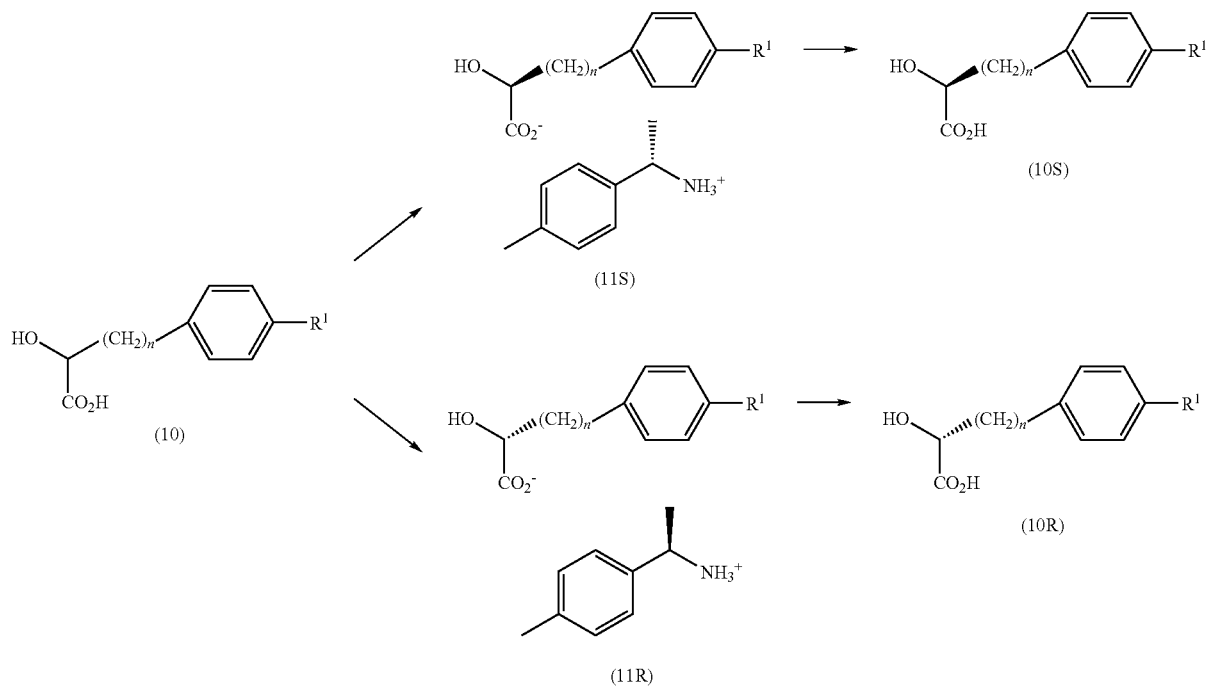

wherein n and $R^1$ are as defined above.

In the formula (10), formula (10S), formula (10R), formula (11S) and formula (11R) in the above reaction scheme, n is preferably 3 or 4.

A compound of the formula (10) as starting material may be produced by a well-known process or the process described in the working example in the present specification.

As shown in the above reaction scheme, a (−)-α-tolylethylamine salt of a compound of the formula (10S) may be isolated as a diastereomeric salt by treating the compound of the formula (10) with (−)-α-tolylethylamine in an inert solvent. The compound of the formula (10S) may be produced by treating the diastereomeric salt with an acid by a conventional method.

A (+)-α-tolylethylamine salt of a compound of the formula (10R) may be isolated as a diastereomeric salt by treating the compound of the formula (10) with (+)-α-tolylethylamine in an inert solvent. The compound of the formula (10R) may be produced by treating this diastereomeric salt with an acid by a conventional method.

Specifically, the optical resolution of the compound of the formula (10) may be carried out by the following steps:

(step 1) a step of dissolving the compound of the formula (10) and an optically active α-tolylethylamine in an inert solvent, (step 2) a step of precipitating crystals of a diastereomeric salt represented by the formula (11S) or (11R), and (step 3) a step of isolating the crystals obtained in (step 2).

The inert solvent used in (step 1) is not particularly limited so long as it can dissolve the compound of the formula (10). Specific examples thereof are acetone, aqueous acetone, acetonitrile, tetrahydrofuran (THF), 1,4-dioxane, ethyl acetate, toluene, alcohols (e.g. ethanol), etc. Preferable examples thereof are acetone and aqueous acetone. The inert solvent may be used in a volume of 5 ml to 10 ml per g of the starting material.

The amount of the optically active α-tolylethylamine used is suitably about 0.8 to about 1.5 equivalents, preferably 1 equivalent, per equivalent of the substrate.

The temperature at the formation of the salt by the dissolution of the compound of the formula (10) and the optically active α-tolylethylamine ranges from room temperature to the boiling point of the inert solvent. The reaction is usually carried out at 40° C. to 70° C. For improving the optical purity, the temperature is preferably once raised close to the boiling point of the solvent.

The reaction time may be properly controlled by monitoring the dissolution of the whole starting material and takes usually 0.5 hour to 2 hours.

A method for precipitating crystals of the α-tolylethylamine salt represented by the formula (11S) or (11R) in (step 2) is not particularly limited, and a method well known to those skilled in the art may be adopted. For example, the crystals may be precipitated by allowing the solution to stand. In this case, the yield may be improved by cooling the solution according to need before collecting the precipitated salt by filtration. In addition, the solvent may be properly distilled off at atmospheric pressure or under reduced pressure and at room temperature or with heating.

In (step 3), the α-tolylethylamine salt represented by the formula (11S) or (11R) may be obtained in high purity by collecting the formed crystals by filtration, and if necessary, recrystallizing the crystals from an inert solvent (for example, an alcohol solvent such as methanol, ethanol or 2-propanol; an ether solvent such as diethyl ether; an ester solvent such as ethyl acetate; an aromatic hydrocarbon solvent such as toluene; acetonitrile; or a mixed solvent thereof). Here, the term "high purity" means a purity of usually 90% ee or more, preferably 95% ee or more, more preferably 98% ee or more.

If necessary, the α-tolylethylamine salt represented by the formula (11S) or (11R) may be converted to the optically active carboxylic acid compound of the formula (10S) or (10R), respectively, by the use of an acid such as hydrochloric acid, phosphoric acid, sulfuric acid or the like. For example, desalting may be conducted by dissolving the α-tolylethylamine salt represented by the formula (11S) or (11R) in an organic solvent such as ethyl acetate, followed by extraction with a 0.1 to 2N aqueous hydrochloric acid solution.

The compound of the formula (10) includes not only a complete racemic modification (0% ee) consisting of the (+) form and the (−) form in the ratio of 1:1 but also a mixture of the (+) form and the (−) form having a certain degree of optical purity. For example, an optically active form of the compound of the formula (10) may be produced by the process described in the production process 7 and may be given a higher purity by the method according to the present invention.

The thus obtained optically active form of the compound of the present invention and optically active form of the intermediate for production of the compound of the present invention may be improved in optical purity, for example, by a method well known to those skilled in the art.

Specifically, such an optically active substance may be separated by purification by a fractional recrystallization method comprising the formation of a salt with an optically active base, a chromatographic method using an optically active column, or the like. As the aforesaid fractional recrystallization method, there is exemplified a method in which a salt with an optically active base (e.g. an organic amine such as α-phenethylamine, α-tolylethylamine, quinine, quinidine, cinchonidine, cinchonine or strychnine) is formed in an inert solvent (e.g. an alcohol solvent such as methanol, ethanol or 2-propanol; an ether solvent such as diethyl ether; an ester solvent such as ethyl acetate; an aromatic hydrocarbon solvent such as toluene; acetonitrile; or a mixed solvent thereof). The temperature at the formation of the salt ranges from room temperature to the boiling point of the solvent. For improving the optical purity, the temperature is preferably once raised close to the boiling point of the solvent. The yield may be improved by cooling the reaction solution according to need before collecting the precipitated salt by filtration. In general, the amount of the optically active acid or amine used is suitably in a range of about 0.5 to about 2.0 equivalents, preferably in a range of about 1 equivalent per equivalent of the substrate. If necessary, an optically active salt having a high purity may be obtained by recrystallizing the crystals from an inert solvent (for example, an alcohol solvent such as methanol, ethanol or 2-propanol; an ether solvent such as diethyl ether; an ester solvent such as ethyl acetate; an aromatic hydrocarbon solvent such as toluene; acetonitrile; or a mixed solvent thereof). If necessary, the salt obtained may be treated with an acid or a base by a conventional method to obtain the optically active substance in the free state.

As the optically active column used in the above-mentioned chromatographic method, optically active columns generally used by those skilled in the art may be used. There is, for example, a method in which the compound of the formula (1) (including the compounds of the formula (1-8) and the formula (3-3)) is optically resolved by the use of, for example, CHIRALCEL (trade name) AD-H or CHIRALCEL AS-RH manufactured by DAICEL Chemical Industries Ltd.

Of optically active forms of the compound of the formula (1) of the present invention, optically active substances having an S-configuration exhibit higher activity. Specific examples of such compounds are the compounds of Example 7 and Example 14.

When the compound of the formula (1) and an intermediate for production of this compound are produced, techniques for protection and deprotection generally known to those skilled in the art may be used if necessary. The techniques for protection and deprotection are described in detail in the above-mentioned "Green reference".

When used as a medicine, the compound of the formula (1) or a pharmaceutically acceptable salt thereof may be administered orally or parenterally and systemically or locally.

A dosage form in the case of the oral administration includes, for example, capsules, tablets, powders, cachets and solutions. As to a dosage form in the case of the parenteral administration, the compound or the salt may be administered in the form of, for example, an injection, transdermal preparation, trans-nasal preparation or intrarectal preparation. As the injection, sterile solutions or suspensions are exemplified. The transdermal preparation includes creams, ointments, lotions, patch preparations, matrix preparations, etc. The intrarectal preparation includes suppositories, enemas (solution injection), etc. The trans-nasal preparation includes aerosols, nasal drops, etc.

When the compound of the formula (1) is used as a preparation for local administration, specific examples of the administration route of the compound are intraarticular administration, transdermal administration, etc.

The compound of the formula (1) or a pharmaceutically acceptable salt thereof may be formulated into a pharmaceutical composition together with pharmaceutically acceptable excipients and additives generally used by those skilled in the art. The pharmaceutically acceptable excipients and additives include carriers, binders, flavoring materials, buffers, thickening agents, coloring agents, stabilizers, emulsifying agents, dispersing agents, suspending agents, antiseptics, etc.

The pharmaceutically acceptable carriers include, for example, magnesium carbonate, magnesium stearate, talc, sugar, lactose, pectin, dextrin, starch, gelatin, tragacanth, methyl cellulose, sodium carboxymethyl cellulose, low-melting wax, and cacao butter. The capsules may be prepared by encapsulating the compound of the present invention together with the pharmaceutically acceptable carrier. The benzothiazin-3-one compound or pharmaceutically acceptable salt thereof of the present invention may be encapsulated together with the pharmaceutically acceptable excipient mixed therewith or without the excipient. The cachets may be prepared in the same manner as above.

As a solution for injection, there are exemplified solutions, suspensions and emulsions, such as aqueous solutions, water-propylene glycol solutions, and the like. The solution for injection may be prepared in the form of a solution in a poly(ethylene glycol) and/or propylene glycol which may contain water. A solution suitable for the oral administration may be prepared by adding the compound of the present invention to water and adding thereto a coloring agent, a flavoring material, a stabilizer, a sweetener, a solvent, a thickening agent and the like according to need. A solution suitable for the oral administration may be prepared also by adding the benzothiazin-3-one compound or pharmaceutically acceptable salt thereof of the present invention to water together with a dispersing agent to increase the viscosity. The thickening agent includes, for example, pharmaceutically acceptable natural or synthetic gums, resins, methyl cellulose, sodium carboxymethyl cellulose, and well-known suspending agents.

The preparation for local administration includes the above-mentioned solutions, creams, aerosols, sprays, powders, lotions, ointments, etc. The above-exemplified preparation for local administration may be produced by mixing the benzothiazin-3-one derivative or salt thereof of the present invention with a diluent and a carrier which are pharmaceutically acceptable and conventionally used. Each of the ointment and the cream is obtained, for example, by adding a thickening agent and/or a gelling agent to an aqueous or oily base ingredient, followed by formulation into a pharmaceutical composition. The base ingredient includes, for example, water, liquid paraffins, and vegetable oils (e.g. peanut oil and castor oil). The thickening agent includes, for example, soft paraffins, aluminum stearate, cetostearyl alcohol, propylene glycol, poly(ethylene glycol)s, lanolin, hydrogenated lanolin, and beeswax.

In the case of the lotion, one or more pharmaceutically acceptable stabilizers, suspending agents, emulsifying agents, dispersing agents, thickening agents, coloring agents, flavoring materials and the like may be added to an aqueous or oily base ingredient.

The powder is obtained by formulating the compound of the formula (1) or a pharmaceutically acceptable salt thereof into the powder together with a pharmaceutically acceptable base ingredient for powder. The base ingredient includes talc, lactose, starch and the like. Drops may be obtained by formulating the compound of the formula (1) or a pharmaceutically acceptable salt thereof into the drops together with an aqueous or nonaqueous base ingredient and one or more pharmaceutically acceptable dispersing agents, suspending agents, solvents and the like.

If necessary, the preparation for local administration may contain antiseptics and bacterial multiplication inhibitors, such as methyl hydroxybenzoate, propyl hydroxybenzoate, chlorocresol, benzalkonium chlorides, etc.

It is also possible to administer through nose a pharmaceutical composition in the form of a solution spray, a powder or drops, which contain the benzothiazin-3-one derivative or salt thereof of the present invention as an active ingredient.

A compound of the formula (1) in which R is an ethyl group and a pharmaceutically acceptable salt thereof are characterized in that they have an excellent oral absorbability and act as a prodrug which is converted to a highly active substance by metabolizing in a living body. That is, as shown in the following scheme:

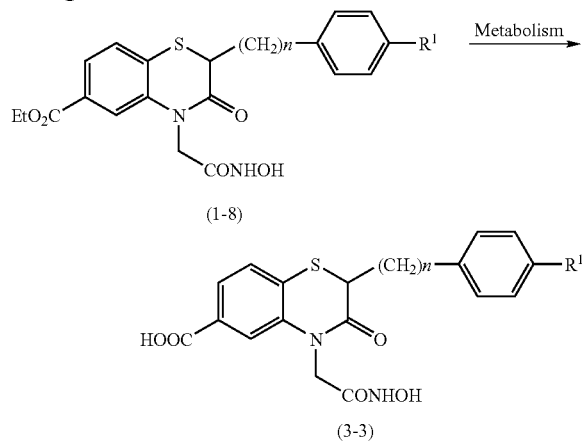

wherein n and $R^1$ are as defined above, a compound of the formula (1-8) is metabolized by enzymes in a living body to be converted to a metabolite represented by the formula (3-3).

When the compound of the formula (1-8) is orally administered, the compound of the formula (3-3) exhibits an excellent MMP inhibitory activity and has a marked MMP inhibitory activity particularly against MMP-3 and MMP-13, in the living body.

That is, the compound of the formula (1-8) or a pharmaceutically acceptable salt thereof is preferably orally administered as a preparation for systemic administration or is parenterally administered as a preparation for local administration.

The compound of the formula (3-3) or a pharmaceutically acceptable salt thereof is preferably parenterally administered.

The dose and the number of administrations of a pharmaceutical composition containing the compound of the formula (1) (the compound of the formula (1-8) or the formula (3-3)) or a pharmaceutically acceptable salt thereof are varied depending on symptom, age, body weight, administration route, etc. When orally administered, the pharmaceutical composition may be administered to an adult in a dose in the range of usually about 1 to about 1000 mg, preferably about 5 to about 300 mg per day in one portion or several portions. When administered as an injection, the pharmaceutical composition may be administered to an adult in a dose in the range of usually about 0.1 to about 300 mg, preferably about 1 to about 100 mg per day in one portion or several portions.

The compound of the formula (1) or a pharmaceutically acceptable salt thereof is usable as a therapeutic or preventive agent for diseases such as chondrodegenerative diseases such as arthrosis deformans and chronic articular rheumatism, cancers, inflammatory diseases, COPD (chronic obstructive pulmonary disease), asthma, multiple sclerosis, dermatitis, spondylosis, periodontal disease, wounds, myalgia, ulcers, stenosis, eating disorder, septicemia, etc.

The compound of the formula (1) or a pharmaceutically acceptable salt thereof is preferably useful as, in particular, a therapeutic agent for chondrodegenerative diseases and is very effective as, in particular, a therapeutic agent for arthrosis deformans.

When used as a therapeutic agent for a specific disease, the compound of the formula (1) or a pharmaceutically acceptable salt thereof may be used in combination with various therapeutic agents for said disease. In the case of chondrodegenerative diseases, the compound of the formula (1) or a pharmaceutically acceptable salt thereof may be used in combination with TNF-α inhibitors (including anti-TNF antibodies), methotrexate, Leflunomide, hydroxychloroquine, d-penicillamine, nonsteroidal anti-inflammatory drugs (e.g. Diclofenac, naproxen, flurbiprofen and ibuprofen), cyclooxygenase 2 inhibitors (e.g. Meloxicam and Celecoxib), salicylic acids (e.g. aspirin), steroids (e.g. corticosteroid), immunosuppressants (e.g. Ciclosporin and Tacrolimus), hyaluronic acids (e.g. Hyalgan and Synvisc), etc. In the case of cancers, the compound of the formula (1) or a pharmaceutically acceptable salt thereof may be used in combination with various anticancer drugs (e.g. Angiostatin, Adriamycin, cisplatin and Taxol).

The present invention is more concretely illustrated with reference to the following examples, which are merely for exemplification and should not be construed as limiting the scope of the invention.

In the following examples, the term "room temperature" or "ambient temperature" means a temperature of 15° C. to 30° C. All of the nonaqueous reactions were carried out under a nitrogen atmosphere. The term "concentration under reduced pressure" means that a rotary evaporator was used.

If necessary, the desired compound obtained may be separated and purified, for example, by recrystallization, reprecipitation, or a proper combination of methods conventionally adopted for separation and purification of an organic compound [for example, an adsorption column chromatography method using a support such as silica gel, alumina, or magnesium-silica gel type Florisil; a method using a synthetic adsorbent, such as partition column chromatography using a support such as Sephadex LH-20 (mfd. by Pharmacia AB), Amberlite XAD-11 (mfd. by Rohm & Haas Co.) or Diaion HP-20 (mfd. by Mitsubishi Chemical Company); a method using ion-exchange chromatography; and a normal-phase or reversed-phase column chromatography (preferably high performance liquid chromatography) using silica gel or lower-alkylated silica gel] followed by elution with a suitable eluent.

In the following description, the NMR data are reported in ppm (δ) and are based on comparison with lock signals of deuterium from a solvent for sample. Commercial reagents were used without further purification. CDCl$_3$ denotes deuterated chloroform and DMSO-d6 denotes deuterated dimethyl sulfoxide. As these reagents, commercial reagents were used without further purification. Abbreviations used in the NMR data are as follows:

s: singlet d: doublet t: triplet dd: doublet doublet m: multiplet br broad brs: broad singlet

EXAMPLE 1

Ethyl 4-[2-(hydroxyamino)-2-oxoethyl]-2-[3-(4-methoxyphenyl)propyl]-3-oxo-3,4-dihydro-2H-1,4-benzothiazine-6-carboxylate

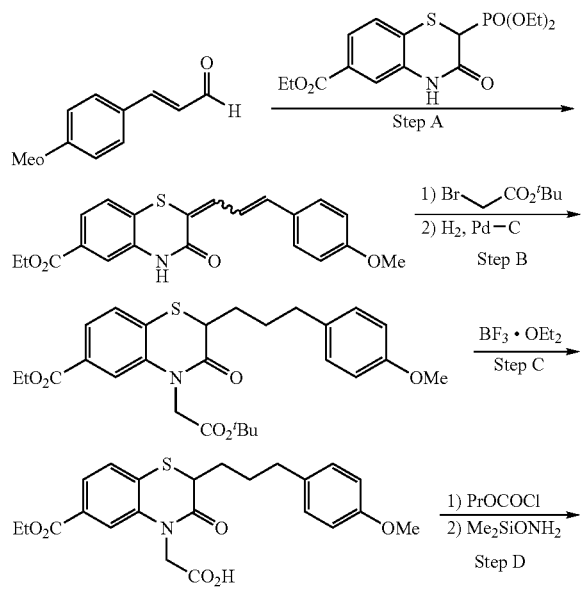

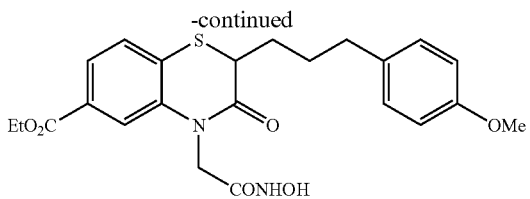

Step A

Under ice-cooling, sodium hydride (4.65 g, content 60%) was added in small portions to a THF solution (300 ml) containing (2E)-3-(4-methoxyphenyl)acrylaldehyde (10 g) synthesized by the process described in Reference Example 1 and ethyl 2-(diethoxyphosphoryl)-3-oxo-3,4-dihydro-2H-1,4-benzothiazine-6-carboxylate (21.7 g, synthesized according to the process disclosed in WO00/63197). The resulting mixture was slowly warmed up to room temperature and stirred overnight. The same aldehyde as above (1.5 g) was added thereto and stirred for another 2 hours. The resulting mixture was concentrated under reduced pressure, and ethyl acetate (30 ml), hexane (100 ml), a 1N aqueous hydrochloric acid solution (50 ml) and water (600 ml) were added to the residue, followed by stirring at room temperature for 6 hours. The solid was collected by filtration and dried under reduced pressure. Ethyl 2-[3-(4-methoxyphenyl)prop-2-en-1-ylidene]-3-oxo-3,4-dihydro-2H-1,4-benzothiazine-6-carboxylate (22.43 g) was obtained as a yellow solid.

$^1$H-NMR (DMSO-d6) δ

1.33 (t, J=7.1 Hz, 3H), 3.76+3.80 (s, 3H), 4.30 (q, J=7.1 Hz, 2H), 6.92-7.08 (m, 4H), 7.35-7.45 (m, 2H), 7.52-7.58 (m, 3H), 7.66 (d, J=1.7 Hz, 1H), 10.90+10.95 (brs, 1H).

Step B

Under ice-cooling, sodium hydride (1.68 g, content 60%) was added in small portions to ethyl 2-[3-(4-methoxyphenyl)prop-2-en-1-ylidene]-3-oxo-3,4-dihydro-2H-1,4-benzothiazine-6-carboxylate (12.3 g) and DMF (150 ml). After 10 minutes, the resulting mixture was stirred at room temperature. After 4 hours, tert-butyl bromoacetate (5.7 ml) was added dropwise thereto under ice-cooling. After 1 hour, the resulting mixture was poured into an aqueous sodium chloride solution and extracted with ethyl acetate. The oil layer was dehydrated over anhydrous sodium sulfate and concentrated under reduced pressure. The residue was purified by a silica gel chromatography (eluent: hexane/ethyl acetate=2/1) to obtain a yellow oil (14.45 g). To this yellow oil were added 1,4-dioxane (200 ml), methanol (200 ml), acetic acid (10 ml) and 10%-palladium-carbon (10 g, containing 50% water), and the resulting mixture was stirred under a hydrogen atmosphere at room temperature and atmospheric pressure. After 12 hours, the solid was filtered off and washed with ethyl acetate and the filtrate was concentrated under reduced pressure. The residue was purified by a silica gel chromatography (hexane/ethyl acetate=3/1) to obtain ethyl 4-(2-tert-butoxy-2-oxoethyl)-2-[3-(4-methoxyphenyl)propyl]-3-oxo-3,4-dihydro-2H-1,4-benzothiazine-6-carboxylate (13.16 g) as a yellow oil.

$^1$H-NMR (CDCl$_3$) δ

1.38 (t, J=7.1 Hz, 3H), 1.49 (s, 9H), 1.60 (m, 1H), 1.71 (m, 1H), 1.75-1.98 (m, 2H), 2.54 (m, 2H), 3.48 (m, 1H), 3.76 (s, 3H), 4.32-4.41 (m, 3H), 4.82 (m, 1H), 6.76-6.80 (m, 2H), 7.02-7.06 (m, 2H), 7.40 (m, 1H), 7.50 (m, 1H), 7.70 (m, 1H).

Step C

Under ice-cooling, a boron trifluoride-diethyl ether complex (26.6 ml) was added dropwise to a solution of ethyl 4-(2-tert-butoxy-2-oxoethyl)-2-[3-(4-methoxyphenyl)propyl]-3-oxo-3,4-dihydro-2H-1,4-benzothiazine-6-carboxylate (13.16 g) and dimethyl sulfide (26.3 ml) in dichloromethane (250 ml). The resulting mixture was slowly warmed up to room temperature and then stirred overnight. The mixture was poured into a 1N aqueous hydrochloric acid solution and extracted with chloroform. The oil layer was washed twice with a 1N aqueous hydrochloric acid solution, dehydrated over anhydrous sodium sulfate and then concentrated under reduced pressure. {6-(Ethoxycarbonyl)-2-[3-(4-methoxyphenyl)propyl]-3-oxo-2,3-dihydro-4H-1,4-benzothiazin-4-yl}acetic acid (10.64 g) was obtained as a yellow oil.

$^1$H-NMR (CDCl$_3$) δ

1.39 (t, J=7.2 Hz, 3H), 1.60 (m, 1H), 1.70 (m, 1H), 1.75-1.93 (m, 2H), 2.52 (m, 2H), 3.50 (m, 1H), 3.77 (s, 3H), 4.38 (q, J=7.2 Hz, 2H), 4.59 (m, 1H), 4.92 (m, 1H), 6.76-6.80 (m, 2H), 7.00-7.04 (m, 2H), 7.41 (d, J=8.1 Hz, 1H), 7.55 (m, 1H), 7.71 (m, 1H).

Step D

At −15° C., isopropyl chloroformate (2.84 ml) was added dropwise to a solution of {6-(ethoxycarbonyl)-2-[3-(4-methoxyphenyl)propyl]-3-oxo-2,3-dihydro-4H-1,4-benzothiazin-4-yl}acetic acid (10.64 g) and N-methylmorpholine (3.2 ml) in tetrahydrofuran (200 ml). After the dropwise addition of the whole isopropyl chloroformate, the resulting mixture was stirred for 25 minutes and then O-(trimethylsilyl)hydroxylamine (3.52 ml) was added dropwise thereto. After 3 hours, the reaction mixture was poured into a 0.5N aqueous hydrochloric acid solution and extracted with ethyl acetate. The oil layer was washed with a saturated aqueous sodium chloride solution, dehydrated over anhydrous sodium sulfate and then concentrated under reduced pressure. The residue was purified by a silica gel chromatography (hexane/ethyl acetate=⅔ to ⅓). To the resulting yellow oil were added toluene and hexane to effect crystallization. The solid obtained was collected by filtration and concentrated under reduced pressure. Ethyl 4-[2-(hydroxyamino)-2-oxoethyl]-2-[3-(4-methoxyphenyl)propyl]-3-oxo-3,4-dihydro-2H-1,4-benzothiazine-6-carboxylate (8.24 g) was obtained as a yellow solid.

$^1$H-NMR (CDCl$_3$) δ

1.40 (t, J=7.2 Hz, 3H), 1.59 (m, 1H), 1.67 (m, 1H), 1.77-1.93 (m, 2H), 2.54 (m, 2H), 3.47 (m, 1H), 3.77 (s, 3H), 4.38 (q, J=7.2 Hz, 2H), 4.51 (d, J=16.0 Hz, 1H), 4.68 (d, J=16.0 Hz, 1H), 6.80 (m, 2H), 7.04 (m, 2H), 7.41 (d, J=8.0 Hz, 1H), 7.52 (br, 1H), 7.73 (m, 1H), 7.98 (br, 1H), 9.16 (br, 1H).

EXAMPLE 2

Ethyl 2-[3-(4-chlorophenyl)propyl]-4-[2-(hydroxyamino)-2-oxoethyl]-3-oxo-3,4-dihydro-2H-1,4-benzothiazine-6-carboxylate

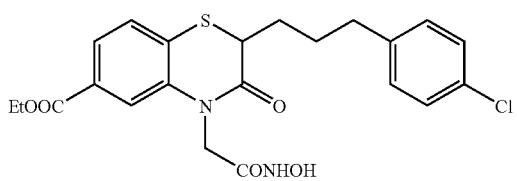

Ethyl 2-[3-(4-chlorophenyl)propyl]-4-[2-(hydroxyamino)-2-oxoethyl]-3-oxo-3,4-dihydro-2H-1,4-benzothiazine-6-carboxylate was obtained by the same process as in Example 1.

$^1$H-NMR (CDCl$_3$) δ: 1.40 (t, J=7.2 Hz, 3H), 1.60 (m, 2H), 1.85 (m, 2H), 2.56 (m, 2H), 3.47 (m, 1H), 4.38 (q, J=7.2 Hz, 2H), 4.52 (d, J=16.0 Hz, 1H), 4.68 (d, J=16.0 Hz, 1H), 7.05 (m, 2H), 7.21 (m, 2H), 7.40 (d, J=8.0 Hz, 1H), 7.60-7.76 (m, 2H), 7.96 (br, 1H), 8.63+9.28 (br, 1H).

EXAMPLE 3

Ethyl 2-[3-(4-fluorophenyl)propyl]-4-[2-(hydroxyamino)-2-oxoethyl]-3-oxo-3,4-dihydro-2H-1,4-benzothiazine-6-carboxylate

Ethyl 2-[3-(4-fluorophenyl)propyl]-4-[2-(hydroxyamino)-2-oxoethyl]-3-oxo-3,4-dihydro-2H-1,4-benzothiazine-6-carboxylate was obtained by the same process as in Example 1.

$^1$H-NMR (CDCl$_3$) δ: 1.40 (t, J=7.2 Hz, 3H), 1.56 (m, 1H), 1.66 (m, 1H), 1.85 (m, 2H), 2.57 (m, 2H), 3.47 (m, 1H), 4.39 (q, J=7.2 Hz, 2H), 4.52 (d, J=15.6 Hz, 1H), 4.69 (d, J=15.6 Hz, 1H), 6.93 (m, 2H), 7.07 (m, 2H), 7.41 (d, J=8.0 Hz, 1H), 7.50 (br, 1H), 7.73 (m, 1H), 7.98 (br, 1H), 9.27 (br, 1H)

EXAMPLE 4

Ethyl 4-[2-(hydroxyamino)-2-oxoethyl]-3-oxo-2-{3-[4-(trifluoromethoxy)phenyl]propyl}-3,4-dihydro-2H-1,4-benzothiazine-6-carboxylate

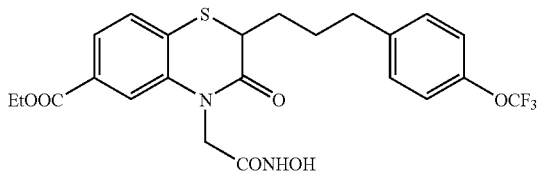

Ethyl 4-[2-(hydroxyamino)-2-oxoethyl]-3-oxo-2-{3-[4-(trifluoromethoxy)phenyl]propyl}-3,4-dihydro-2H-1,4-benzothiazine-6-carboxylate was obtained by the same process as in Example 1.

$^1$H-NMR (CDCl$_3$) δ: 1.40 (t, J=7.2 Hz, 3H), 1.61 (m, 1H), 1.69 (m, 1H), 1.84 (m, 2H), 2.60 (m, 2H), 3.49 (m, 1H), 4.39 (t, J=7.2 Hz, 2H), 4.52 (d, J=16.4 Hz, 1H), 4.70 (d, J=16.4 Hz, 1H), 7.08-7.16 (m, 4H), 7.41 (d, J=8.0 Hz, 2H), 7.73 (m, 2H), 7.99 (br, 1H), 9.21 (br, 1H).

EXAMPLE 5

Ethyl 4-[2-(hydroxyamino)-2-oxoethyl]-3-oxo-2-{3-[4-(trifluoromethyl)phenyl]propyl}-3,4-dihydro-2H-1,4-benzothiazine-6-carboxylate

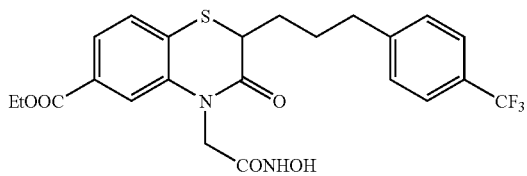

Ethyl 4-[2-(hydroxyamino)-2-oxoethyl]-3-oxo-2-{3-[4-(trifluoromethyl)phenyl]propyl}-3,4-dihydro-2H-1,4-benzothiazine-6-carboxylate was obtained by the same process as in Example 1.

$^1$H-NMR (DMSO-d6) δ: 1.31 (t, J=7.2 Hz, 3H), 1.45 (m, 1H), 1.71 (m, 3H), 2.65 (m, 2H), 3.76 (m, 1H), 4.30 (q, J=7.2 Hz, 2H), 4.37 (d, J=8.4 Hz, 1H), 4.58 (d, J=8.4 Hz, 1H), 7.38 (m, 2H), 7.52-7.61 (m, 5H), 9.04+9.44 (s, 1H), 10.39+10.84 (s, 1H).

EXAMPLE 6

Ethyl 4-[2-(hydroxyamino)-2-oxoethyl]-2-[4-(4-methoxyphenyl)butyl]-3-oxo-3,4-dihydro-2H-1,4-benzothiazine-6-carboxylate

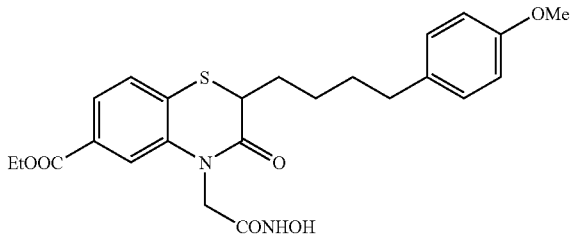

Ethyl 4-[2-(hydroxyamino)-2-oxoethyl]-2-[4-(4-methoxyphenyl)butyl]-3-oxo-3,4-dihydro-2H-1,4-benzothiazine-6-carboxylate was obtained by the same process as in Example 1.

$^1$H-NMR (DMSO-d6) δ: 1.31 (t, J=7.2 Hz, 3H), 1.35-1.54 (m, 5H), 1.73 (m, 1H), 2.44 (m, 2H), 3.63-3.72 (m, 4H), 4.31 (q, J=7.2 Hz, 2H), 4.41 (d, J=16.8 Hz, 1H), 4.55 (d, J=16.8 Hz, 1H), 6.80 (m, 2H), 7.05 (m, 2H), 7.55 (d, J=8.4 Hz, 1H), 7.60-7.64 (m, 2H), 9.04+9.43 (s, 1H), 10.38+10.83 (s, 1H).

EXAMPLE 7

(−)-Ethyl 4-[2-(hydroxyamino)-2-oxoethyl]-2-[3-(4-methoxyphenyl)propyl]-3-oxo-3,4-dihydro-2H-1,4-benzothiazine-6-carboxylate

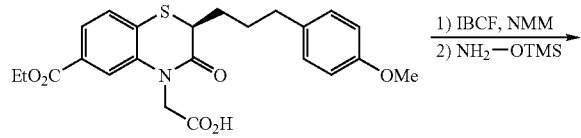

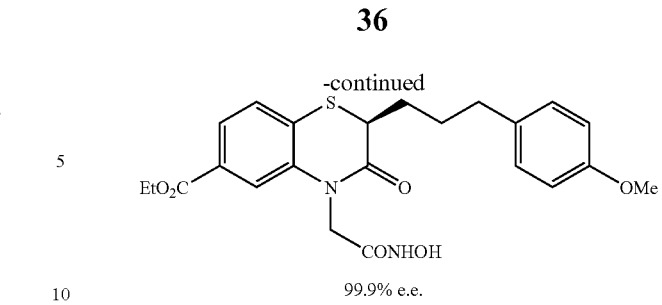

99.9% e.e.

In THF (40 ml) was dissolved {(2S)-6-(ethoxycarbonyl)-2-[3-(4-methoxyphenyl)propyl]-3-oxo-2,3-dihydro-4H-1,4-benzothiazin-4-yl}acetic acid (the compound of Reference Example 11) (2.06 g), and isobutyl chloroformate (0.72 ml) and N-methylmorpholine (0.51 ml) were added thereto at −20° C. and stirred at −10 to −20° C. for 30 minutes. After O-(trimethylsilyl)hydroxylamine (0.87 ml) was added thereto, the resulting mixture was warmed up to room temperature and stirred for 1 hour. The reaction mixture was poured into a saturated aqueous sodium hydrogencabonate solution and extracted with ethyl acetate, and the organic layer was washed with a saturated aqueous ammonium chloride solution and a saturated aqueous sodium chloride solution and then dried over anhydrous sodium sulfate. The drying agent was removed by filtration and the solvent was distilled off under reduced pressure. The residue was recrystallized from a mixed solvent of ethyl acetate and diisopropyl ether to obtain (−)-ethyl 4-[2-(hydroxyamino)-2-oxoethyl]-2-[3-(4-methoxyphenyl)propyl]-3-oxo-3,4-dihydro-2H-1,4-benzothiazine-6-carboxylate (1.69 g, 99.9% e.e.). The optical purity analysis conditions are as follows. [Column: AD-H (CHIRALCEL, DAICEL Chemical Industries Ltd.); detecting wavelength (UV): 254 nm; flow rate: 1.0 ml/min; mobile phase: n-hexane/isopropyl alcohol/TFA=80/20/0.1]

Melting point: 143.5-144.5° C.

$[α]_D^{20}$=−85.3° (c: 1.0, CHCl$_3$)

$^1$H-NMR (CDCl$_3$) δ: 1.40 (t, J=7.2 Hz, 3H), 1.59 (m, 1H), 1.67 (m, 1H), 1.77-1.93 (m, 2H), 2.54 (m, 2H), 3.47 (m, 1H), 3.77 (s, 3H), 4.38 (q, J=7.2 Hz, 2H), 4.51 (d, J=16.0 Hz, 1H), 4.68 (d, J=16.0 Hz, 1H), 6.80 (m, 2H), 7.04 (m, 2H), 7.41 (d, J=8.0 Hz, 1H), 7.52 (br, 1H), 7.73 (m, 1H), 7.98 (br, 1H), 9.16 (br, 1H).

EXAMPLE 8

4-[2-(Hydroxyamino)-2-oxoethyl]-2-[3-(4-methoxyphenyl)propyl]-3-oxo-3,4-dihydro-2H-1,4-benzothiazine-6-carboxylic acid

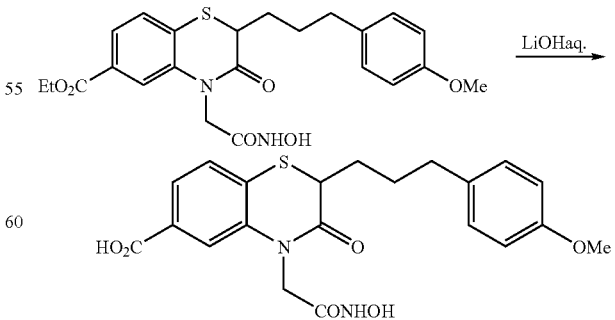

To the compound of Example 1 (0.51 g) were added THF (10 ml) and water (10 ml). After the resulting mixture was ice-cooled, a 0.5N aqueous lithium hydroxide solution (4.4 ml) was slowly added dropwise thereto. The resulting mixture was slowly warmed up to room temperature and stirred overnight. Ice-cooled 1N aqueous hydrochloric acid solution and ethyl acetate were added thereto to effect extraction. The oil layer was washed twice with a 1N aqueous hydrochloric acid solution, dried over anhydrous sodium sulfate and then concentrated under reduced pressure. Chloroform was added to the residue, and after standing for 4 days, the solid precipitated was collected by filtration and dried under reduced pressure. 4-[2-(Hydroxyamino)-2-oxoethyl]-2-[3-(4-methoxyphenyl)propyl]-3-oxo-3,4-dihydro-2H-1,4-benzothiazine-6-carboxylic acid (325 mg) was obtained as a white solid.

$^1$H-NMR (DMSO-d6) δ

1.43 (m, 1H), 1.66 (m, 3H), 2.45 (m, 2H), 3.69 (s, 3H), 4.38 (d, J=16.8 Hz, 1H), 4.54 (d, J=16.8 Hz, 1H), 6.80 (m, 2H), 7.05 (m, 2H), 7.51 (m, 1H), 7.58-7.60 (m, 2H), 9.02+9.43 (s, 1H), 10.36+10.81 (s, 1H), 13.20 (brs, 1H).

EXAMPLE 9

2-[3-(4-Chlorophenyl)propyl]-4-[2-(hydroxyamino)-2-oxoethyl]-3-oxo-3,4-dihydro-2H-1,4-benzothiazine-6-carboxylic acid

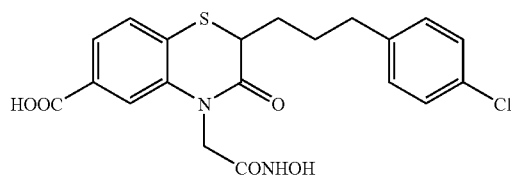

2-[3-(4-Chlorophenyl)propyl]-4-[2-(hydroxyamino)-2-oxoethyl]-3-oxo-3,4-dihydro-2H-1,4-benzothiazine-6-carboxylic acid was obtained by a process similar to the process described in Example 8.

$^1$H-NMR (DMSO-d6) δ

1.45 (m, 1H), 1.68 (m, 3H), 2.54 (m, 2H), 3.73 (m, 1H), 4.38 (d, J=16.4 Hz, 2H), 4.56 (d, J=16.4 Hz, 1H), 7.18 (m, 2H), 7.29 (m, 2H), 7.51 (d, J=8.0 Hz, 1H), 7.59-7.61 (m, 2H), 9.03+9.43 (s, 1H), 10.37+10.82 (s, 1H), 13.17 (br, 1H).

EXAMPLE 10

2-[3-(4-Fluorophenyl)propyl]-4-[2-(hydroxyamino)-2-oxoethyl]-3-oxo-3,4-dihydro-2H-1,4-benzothiazine-6-carboxylic acid

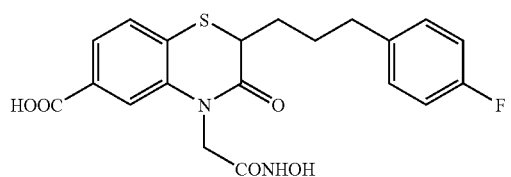

2-[3-(4-Fluorophenyl)propyl]-4-[2-(hydroxyamino)-2-oxoethyl]-3-oxo-3,4-dihydro-2H-1,4-benzothiazine-6-carboxylic acid was obtained by a process similar to the process described in Example 8.

$^1$H-NMR (DMSO-d6) δ

1.45 (m, 1H), 1.67 (m, 3H), 2.54 (m, 2H), 3.73 (m, 1H), 4.38 (d, J=16.8 Hz, 2H), 4.55 (d, J=16.8 Hz, 1H), 7.06 (m, 2H), 7.18 (m, 2H), 7.51 (d, J=8.0 Hz, 1H), 7.59 (m, 2H), 9.03+9.43 (s, 1H), 10.37+10.82 (s, 1H), 13.17 (br, 1H).

EXAMPLE 11

4-[2-(Hydroxyamino)-2-oxoethyl]-3-oxo-2-{3-[4-(trifluoromethoxy)phenyl]propyl}-3,4-dihydro-2H-1,4-benzothiazine-6-carboxylic acid

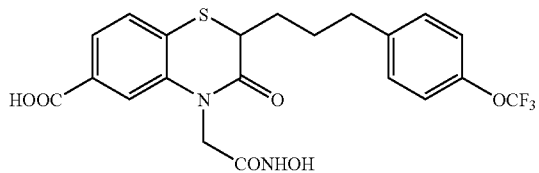

4-[2-(Hydroxyamino)-2-oxoethyl]-3-oxo-2-{3-[4-(trifluoromethoxy)phenyl]propyl}-3,4-dihydro-2H-1,4-benzothiazine-6-carboxylic acid was obtained by a process similar to the process described in Example 8.

$^1$H-NMR (DMSO-d6) δ

1.47 (m, 1H), 1.70 (m, 3H), 2.59 (m, 2H), 3.75 (m, 1H), 4.39 (d, J=16.8 Hz, 1H), 4.56 (d, J=16.8 Hz, 1H), 7.22 (m, 2H), 7.28 (m, 2H), 7.51 (m, 1H), 7.59 (m, 2H), 9.63+9.43 (s, 1H), 10.37+10.82 (s, 1H), 13.12 (br, 1H).

EXAMPLE 12

4-[2-(Hydroxyamino)-2-oxoethyl]-3-oxo-2-{3-[4-(trifluoromethyl)phenyl]propyl}-3,4-dihydro-2H-1,4-benzothiazine-6-carboxylic acid

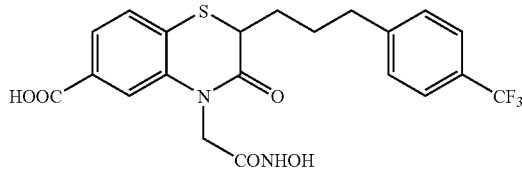

4-[2-(Hydroxyamino)-2-oxoethyl]-3-oxo-2-{3-[4-(trifluoromethyl)phenyl]propyl}-3,4-dihydro-2H-1,4-benzothiazine-6-carboxylic acid was obtained by a process similar to the process described in Example 8.

$^1$H-NMR (DMSO-d6) δ

1.47 (m, 1H), 1.72 (m, 3H), 2.64 (m, 2H), 3.76 (m, 1H), 4.38 (d, J=16.8 Hz, 1H), 4.56 (d, J=16.8 Hz, 1H), 7.49 (m, 2H), 7.51 (m, 1H), 7.58-7.61 (m, 3H), 9.03+9.44 (s, 1H), 10.37+10.82 (s, 1H), 13.13 (br, 1H).

EXAMPLE 13

4-[2-(Hydroxyamino)-2-oxoethyl]-2-[4-(4-methoxyphenyl)butyl]-3-oxo-3,4-dihydro-2H-1,4-benzothiazine-6-carboxylic acid

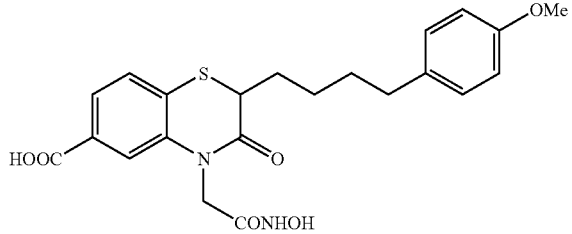

4-[2-(Hydroxyamino)-2-oxoethyl]-2-[4-(4-methoxyphenyl)butyl]-3-oxo-3,4-dihydro-2H-1,4-benzothiazine-6-carboxylic acid was obtained by a process similar to the process described in Example 8.

¹H-NMR (DMSO-d6) δ

1.35-1.56 (m, 5H), 1.75 (m, 1H), 2.45 (m, 2H), 3.68 (m, 1H), 3.70 (s, 3H), 4.41 (d, J=16.8 Hz, 1H), 4.53 (d, J=16.8 Hz, 1H), 6.80 (m, 2H), 7.05 (m, 2H), 7.52 (d, J=8.0 Hz, 1H), 7.58-7.62 (m, 2H), 9.03+9.43 (s, 1H), 10.36+10.81 (s, 1H), 13.06 (br, 1H).

EXAMPLE 14

(−)-4-[2-(Hydroxyamino)-2-oxoethyl]-2-[3-(4-methoxyphenyl)propyl]-3-oxo-3,4-dihydro-2H-1,4-benzothiazine-6-carboxylic acid

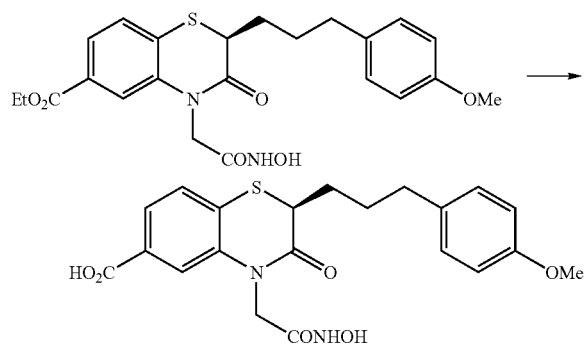

The compound of Example 7 (0.51 g) was added to a solution prepared by adding N-methylglucamine to a 0.1M aqueous sodium dihydrogenphosphate solution to adjust the pH to 8.0, and the resulting mixture was stirred at 40° C. Porcine liver esterase (250 mg) was added thereto and the resulting mixture was stirred at 40° C. for 8 hours and then at room temperature for 4 days. After the reaction mixture was filtered, potassium hydrogensulfate (13.0 g) was added to the filtrate, followed by extraction with ethyl acetate. The oil layer was washed with a 5% aqueous potassium hydrogensulfate solution and a saturated aqueous sodium chloride solution, dehydrated over anhydrous sodium sulfate and then concentrated under reduced pressure. To the residue were added THF and diisopropyl ether to effect crystallization, and the solid was collected by filtration and dried under reduced pressure. (−)-4-[2-(Hydroxyamino)-2-oxoethyl]-2-[3-(4-methoxyphenyl)propyl]-3-oxo-3,4-dihydro-2H-1,4-benzothiazine-6-carboxylic acid (376 mg, 99% e.e.) was obtained as a white solid. The optical purity analysis conditions are as follows. [Column: AS-RH (Chiralcel, DAICEL Chemical Industries Ltd.); detecting wavelength (UV): 254 nm; flow rate: 1.0 ml/min; mobile phase: acetonitrile/0.2M phosphate buffer (pH 2)=25/75]

$[\alpha]_D^{18}$=−92.1° (c: 0.1, EtOH)

¹H-NMR (DMSO-d6) δ

1.43 (m, 1H), 1.66 (m, 3H), 2.45 (m, 2H), 3.69 (s, 3H), 4.38 (d, J=16.8 Hz, 1H), 4.54 (d, J=16.8 Hz, 1H), 6.80 (m, 2H), 7.05 (m, 2H), 7.51 (m, 1H), 7.58-7.60 (m, 2H), 9.02+9.43 (s, 1H), 10.36+10.81 (s, 1H), 13.20 (brs, 1H).

EXAMPLE 15

(−)-4-[2-(Hydroxyamino)-2-oxoethyl]-2-[3-(4-methoxyphenyl)propyl]-3-oxo-3,4-dihydro-2H-1,4-benzothiazine-6-carboxylic acid

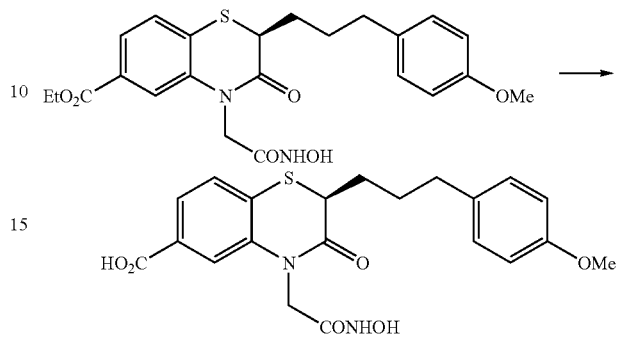

In THF (200 mL) was dissolved 4.59 g (10.0 mmol) of the compound of Example 7 (HPLC purity 99% and optical purity 100% ee), and 2N—KOH (12.5 mL, 25.0 mmol) was added thereto with stirring at −10° C. (internal temperature) and stirred at the same temperature for 5 hours. The reaction mixture was poured into a 0.1N-aqueous hydrochloric acid solution (500 mL) cooled at 0° C. and extracted twice with ethyl acetate (400+100 mL). The organic layer was collected, washed with water and a saturated aqueous sodium chloride solution, dried over magnesium sulfate and then concentrated with an evaporator to obtain 4.65 g of (−)-4-[2-(hydroxyamino)-2-oxoethyl]-2-[3-(4-methoxyphenyl)propyl]-3-oxo-3,4-dihydro-2H-1,4-benzothiazine-6-carboxylic acid (HPLC purity 97% and optical purity 94% ee) as a light-yellow solid.

EXAMPLE 16

(−)-4-[2-(Hydroxyamino)-2-oxoethyl]-2-[3-(4-methoxyphenyl)propyl]-3-oxo-3,4-dihydro-2H-1,4-benzothiazine-6-carboxylic acid

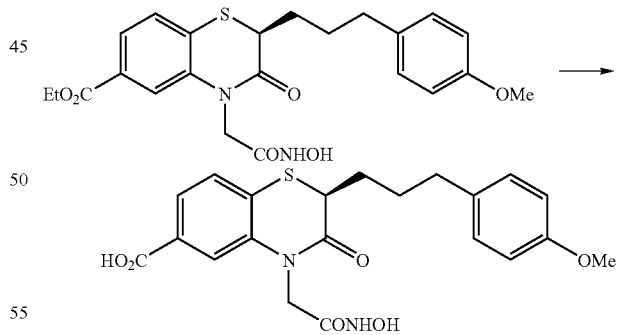

In THF (1 L) was dissolved 46.0 g (100 mmol) of the compound of Example 7 (HPLC purity 99% and optical purity 100% ee), and 2N—NaOH (125 mL, 250 mmol) was added thereto with stirring at −10° C. (internal temperature) and stirred at the same temperature for 3 hours. The reaction mixture was poured into a 0.2N-aqueous hydrochloric acid solution (2 L) cooled at 0° C. and extracted twice with ethyl acetate (1.5+0.5 L). The organic layer was collected, washed with water and a saturated aqueous sodium chloride solution, dried over magnesium sulfate and then concentrated with an evaporator to obtain 50.3 g of a light-yellow solid (HPLC purity 97% and optical purity 94% ee). Chloroform (500 ml) was added to the solid and the resulting mixture was heated under reflux on an oil bath. When the solid dissolved, the reactor was taken off the oil bath, and seed crystals (a earpickful) of the desired compound were added to the reaction solution and the resulting mixture was heated under reflux on the oil bath for 30 minutes to obtain a slurry. Then, the slurry was stirred overnight at room temperature. The slightly brown crystals precipitated were collected by filtration and dried under reduced pressure at 50° C. to obtain 35.7 g of the desired compound (HPLC purity 99% and optical purity 98% ee) as a crude product. The crude product was dissolved in ethanol (200 mL) and hexane (200 mL) was added thereto with stirring at room temperature. Then, hexane (200 mL) was added dropwise thereto while adding seed crystals (0.26 g, 0.60 mmol) of the desired compound in several portions. The resulting mixture was stirred overnight at room temperature. The crystals precipitated were collected by filtration and dried under reduced pressure at 50° C. to obtain 27.0 g of (−)-4-[2-(hydroxyamino)-2-oxoethyl]-2-[3-(4-methoxyphenyl)propyl]-3-oxo-3,4-dihydro-2H-1,4-benzothiazine-6-carboxylic acid (HPLC purity 99% and optical purity 99% ee or more) as white crystals.

EXAMPLE 17

(−)-4-[2-(Hydroxyamino)-2-oxoethyl]-2-[3-(4-methoxyphenyl)propyl]-3-oxo-3,4-dihydro-2H-1,4-benzothiazine-6-carboxylic acid

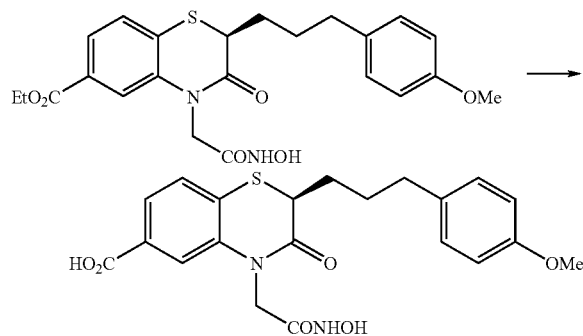

In THF (100 mL) was dissolved 9.19 g (20.0 mmol) of the compound of Example 7 (HPLC purity 99% and optical purity 100% ee), and 4N—NaOH (12.0 mL, 48.0 mmol) was added thereto with stirring at −10° C. (internal temperature) and stirred at the same temperature for 4 hours. The reaction mixture was poured into a 0.2N-aqueous hydrochloric acid solution (400 mL) cooled at 0° C. and extracted twice with ethyl acetate (300+100 mL). The organic layer was collected, washed with water and a saturated aqueous sodium chloride solution, dried over magnesium sulfate and then concentrated with an evaporator to obtain 9.27 g of a light-yellow solid (HPLC purity 94% and optical purity 96% ee). This solid was dissolved in ethanol (50 mL) and pentane (50 mL) was added thereto with stirring at room temperature. Then, pentane (50 mL) was added dropwise thereto while adding seed crystals (0.62 g, 1.44 mmol) of the desired compound in several portions. The resulting mixture was stirred overnight at room temperature. The crystals precipitated were collected by filtration and dried under reduced pressure at 50° C. to obtain 4.75 g of (−)-4-[2-(hydroxyamino)-2-oxoethyl]-2-[3-(4-methoxyphenyl)propyl]-3-oxo-3,4-dihydro-2H-1,4-benzothiazine-6-carboxylic acid (HPLC purity 99% and optical purity 99% ee or more) as white crystals.

Reference Example 1

(2E)-3-(4-Methoxyphenyl)acryl-aldehyde

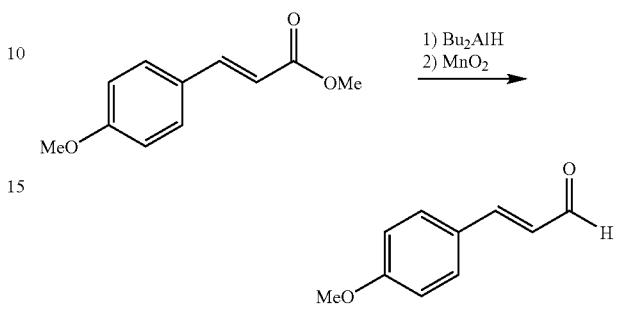

A solution of diisobutylaluminum hydride in hexane (0.95 molar concentration, 200 ml) was added dropwise to a solution of methyl (2E)-3-(4-methoxyphenyl)acrylate (18 g) in THF (150 ml) under ice-cooling. The resulting mixture was slowly warmed up to room temperature and then poured into an ice-cooled aqueous hydrochloric acid solution. After extraction with ethyl acetate, the oil layer was washed with a 1N aqueous hydrochloric acid solution and then a saturated aqueous sodium chloride solution, dehydrated over anhydrous sodium sulfate, and concentrated under reduced pressure. A white solid (13.67 g) was obtained.

Subsequently, manganese dioxide (38.4 g) was added to a solution of the white solid (7.67 g) in chloroform (200 ml), and the resulting mixture was stirred overnight at room temperature. The solid was collected by filtration through Celite and washed with chloroform and then the filtrate was concentrated under reduced pressure. The remaining white solid (6 g) was subjected to the same procedure as above. The concentrates thus obtained were combined to obtain (2E)-3-(4-methoxyphenyl)acrylaldehyde (13.7 g) as a yellow solid.

$^1$H-NMR (CDCl$_3$) δ 3.86 (s, 3H), 6.61 (dd, J=15.8, 7.8 Hz, 1H), 6.95 (d, J=8.6 Hz, 2H), 7.43 (d, J=15.9 Hz, 1H), 7.53 (d, J=8.6 Hz, 2H), 9.65 (d, J=7.7 Hz, 1H).

Reference Example 2

(2R)-2-hydroxy-5-(4-methoxy-phenyl)pentanoic acid

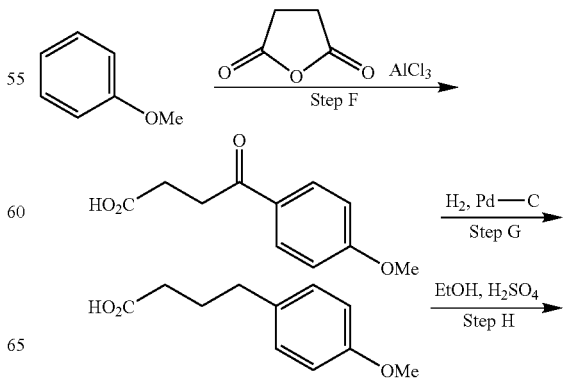

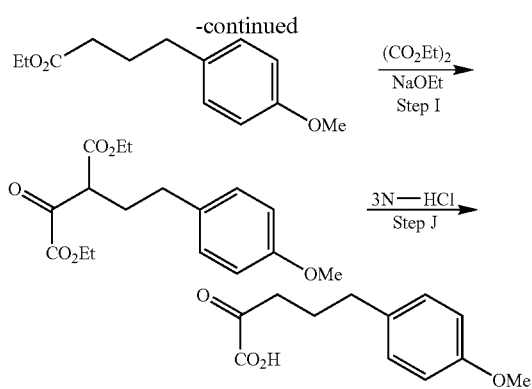

Step F

Methylene chloride (300 ml) was added to aluminum chloride (185.6 g) and anisole (100 ml) was added dropwise thereto at 0° C. Succinic anhydride (100 g) was added thereto in 5 portions and the resulting mixture was warmed up to room temperature and stirred for 3 hours. The reaction solution was added to a 4N aqueous hydrochloric acid solution (2 L) and ethyl acetate (1 L) under ice-cooling, and the crystals precipitated were collected by filtration and dried to obtain 4-(4-methoxyphenyl)-4-oxobutanoic acid (160 g) as a white solid.

$^1$H-NMR (DMSO-d6) δ 2.56 (t, J=6.3 Hz, 2H), 3.18 (t, J=6.3 Hz, 2H), 3.84 (s, 3H), 7.02-7.07 (m, 2H), 7.94-7.98 (m, 2H), 12.14 (brs, 1H).

Step G

After 4-(4-methoxyphenyl)-4-oxobutanoic acid (40 g) was added to (not completely dissolved in) a mixed solvent of acetic acid (100 ml) and THF (100 ml), 10% palladium-carbon (50%-wet) (4 g) was added thereto and the resulting mixture was stirred for 9 hours under a hydrogen atmosphere (0.4 MPa). The catalyst was removed by filtration through Celite and toluene was added to the residue. The solvent was distilled off under reduced pressure to obtain 4-(4-methoxyphenyl)butanoic acid quantitatively.

$^1$H-NMR (CDCl$_3$) δ
1.89 (m, 2H), 2.32 (t, J=7.3 Hz, 2H), 2.58 (t, J=7.4 Hz, 2H), 3.73 (s, 3H), 6.78-6.82 (m, 2H), 7.03-7.08 (m, 2H), 10.96 (brs, 1H).

Step H

After 4-(4-methoxyphenyl)butanoic acid (200 g) and then concentrated sulfuric acid (4 ml) were added to ethanol (400 ml), the resulting mixture was heated under reflux for 1 hour. About one-half of the solvent was distilled off under reduced pressure, and the residual reaction solution was poured into a saturated aqueous sodium hydrogencarbonate solution and extracted with ethyl acetate (1 L). The organic layer was washed with a saturated aqueous sodium chloride solution and dried over anhydrous magnesium sulfate. The solvent was distilled off under reduced pressure to obtain ethyl 4-(4-methoxyphenyl)butanoate quantitatively.

$^1$H-NMR (CDCl$_3$) δ
1.24 (t, J=7.1 Hz, 3H), 1.92 (m, 2H), 2.30 (t, J=7.5 Hz, 2H), 2.59 (t, J=7.4 Hz, 2H), 3.78 (s, 3H), 4.13 (q, J=7.1 Hz, 2H), 6.80-6.84 (m, 2H), 7.07-7.12 (m, 2H).

Step I

A previously prepared solution of NaOEt (184 g) in ethanol (940 ml) was added dropwise to ethyl 4-(4-methoxyphenyl)butanoate (200.1 g) and diethyl oxalate (407 ml) under ice-cooling. After stirring at 50° C. for 10 hours, the resulting solution was poured into an ice-cooled 3N aqueous hydrochloric acid solution (1.8 L). After extraction with ethyl acetate (600 ml×3 times), the extract solution was distilled under reduced pressure to remove the solvent, and the brown organic layer thus separated was collected. The crystals precipitated in the organic layer were collected by filtration and washed with hexane/ethyl acetate=10/2. The washings and the organic layer freed from the crystals were combined and the solvent was distilled off. The residue was used in the subsequent step.

$^1$H-NMR (CDCl$_3$) δ
1.25 (t, J=7.1 Hz, 3H), 1.36 (t, J=7.1 Hz, 3H), 2.16-2.28 (m, 2H), 2.59-2.67 (m, 2H), 3.89 (s, 3H), 4.00 (t, J=6.9 Hz, 1H), 4.19 (q, J=7.1 Hz, 2H), 4.32 (q, J=7.1 Hz, 2H), 6.80-6.84 (m, 2H), 7.07-7.12 (m, 2H).

Step J

The product described above (403 g) was dissolved in 1,4-dioxane (675 ml), followed by adding thereto a 3N aqueous hydrochloric acid solution (1100 ml), and the resulting mixture was heated under reflux for 23 hours. The reaction solution was cooled to room temperature and allowed to stand. The organic layer thus separated and an extract solution obtained by extracting the aqueous layer with ethyl acetate (500 ml) were collected, and the solvent was distilled off under reduced pressure. The residue was adjusted to pH 9 with a 2N aqueous sodium hydroxide solution and the solid precipitated was collected by filtration and washed with water. After a 3N aqueous hydrochloric acid solution was added to the recovered solid to adjust the pH to 2, the precipitate was collected by filtration, washed with water and then dried to obtain 5-(4-methoxyphenyl)-2-oxopentanoic acid (144.8 g) as a brown solid.

$^1$H-NMR (CDCl$_3$) δ
1.96 (m, 2H), 2.62 (t, J=7.4 Hz, 2H), 2.93 (t, J=7.2 Hz, 2H), 3.79 (s, 3H), 6.82-6.86 (m, 2H), 7.05-7.12 (m, 2H), 8.02 (brs, 1H).

Reference Example 3

2-Hydroxy-5-(4-methoxyphenyl)pentanoic acid

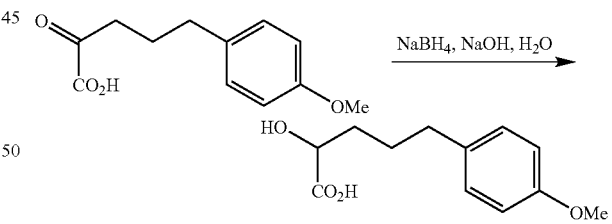

Sodium hydroxide (24.0 g) and water (450 ml) were added to 5-(4-methoxyphenyl)-2-oxopentanoic acid (66.6 g) (the compound of Reference Example 2), and the resulting mixture was ice-cooled. When to this slurry was added sodium tetrahydroborate (3.99 g) in portions, the reaction mixture once became clear. After the reaction mixture was stirred for 2 hours, a 3N aqueous hydrochloric acid solution (300 ml) was added thereto, followed by extraction with ethyl acetate (300 ml×twice). The organic layer was washed with water (100 ml×three times) and dried over anhydrous sodium sulfate. The solvent was distilled off under reduced pressure to obtain 2-hydroxy-5-(4-methoxyphenyl)pentanoic acid (63.4 g) as a crude product.

$^1$H-NMR (CDCl$_3$) δ: 1.67-1.80 (m, 3H), 1.83-1.90 (m, 1H), 2.62 (m, 2H), 3.79 (s, 3H), 4.28 (m, 1H), 6.82 (m, 2H), 7.10 (m, 2H).

Reference Example 4

(2R)-2-Hydroxy-5-(4-methoxyphenyl)pentanoic acid

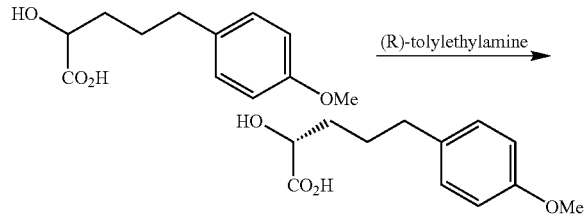

The compound of Reference Example 3 (2-hydroxy-5-(4-methoxyphenyl)pentanoic acid) (1.0 g) was dissolved in acetone (10 ml), followed by adding thereto (+)-tolylethylamine (0.6 g), and the resulting mixture was heated under reflux to dissolve completely. Crystals were precipitated at room temperature and collected by filtration as crude crystals. The crude crystals obtained were resuspended in acetone (10 ml) and the resulting suspension was refluxed and then slowly cooled. The crystals thus obtained were collected by filtration to obtain (+)-tolylethylamine salt (0.59 g, 98% e.e.) of (2R)-2-hydroxy-5-(4-methoxyphenyl)pentanoic acid. A 1N aqueous hydrochloric acid solution (20 ml) was added to the white crystals obtained and the resulting mixture was stirred at room temperature. The precipitate was collected by filtration and dried to obtain (2R)-2-hydroxy-5-(4-methoxyphenyl)pentanoic acid (0.36 g) having an optical purity of 98% e.e., as a white solid. The optical purity analysis conditions are as follows. [Optical purity analysis conditions: column=OJ-H (Chiralcel, DAICEL Chemical Industries Ltd.); detecting wavelength (UV)=276 nm; flow rate: 1.0 ml/min; mobile phase=n-hexane/ethanol/TFA (90/10/0.2)]

$^1$H-NMR (CDCl$_3$) δ: 1.66-1.92 (m, 4H), 2.61 (m, 1H), 3.78 (s, 3H), 4.26 (m, 1H), 6.80-6.85 (m, 2H), 7.03-7.12 (m, 2H).

Reference Example 5

4-Nitrobenzyl (2R)-2-hydroxy-5-(4-methoxyphenyl)pentanoate

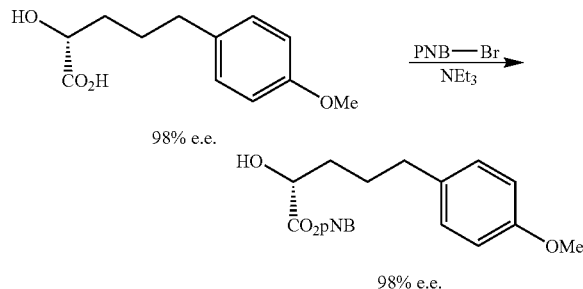

The compound of Reference Example 4 (4.21 g, 98% e.e.) was dissolved in DMF (40 ml), and p-nitrobenzyl bromide (4.06 g) and triethylamine (3.2 ml) were added thereto under ice-cooling. The resulting mixture was stirred for 5 minutes, warmed up to room temperature and then stirred for 2 hours. The reaction mixture was poured into a saturated aqueous ammonium chloride solution and extracted with ethyl acetate, and the extract solution was washed with a saturated aqueous sodium chloride solution and dried over anhydrous sodium sulfate. The drying agent was removed, followed by concentration under reduced pressure, and the residue was purified by a silica gel column chromatography (hexane/ethyl acetate=2/1) to obtain 4-nitrobenzyl (2R)-2-hydroxy-5-(4-methoxyphenyl)pentanoate (5.43 g, 98% e.e.). The optical purity analysis conditions are as follows. [Optical purity analysis conditions: column=AD-RH (Chiralcel, DAICEL Chemical Industries Ltd.); detecting wavelength (UV)=254 nm; flow rate: 1.0 ml/min; mobile phase=acetonitrile/water (50/50)]

$^1$H-NMR (CDCl$_3$) δ: 1.60-1.90 (m, 4H), 2.56 (m, 2H), 2.68 (d, J=5.8 Hz, 1H), 3.79 (s, 3H), 4.29 (m, 1H), 5.25 (d, J=13.2 Hz, 1H), 5.30 (d, J=13.2 Hz, 1H), 6.79-6.83 (m, 2H), 7.04-7.09 (m, 2H), 7.47 (d, J=8.8 Hz, 2H), 8.19-8.24 (m, 2H).

Reference Example 6

Ethyl 3-bromo-4-mercaptobenzoate

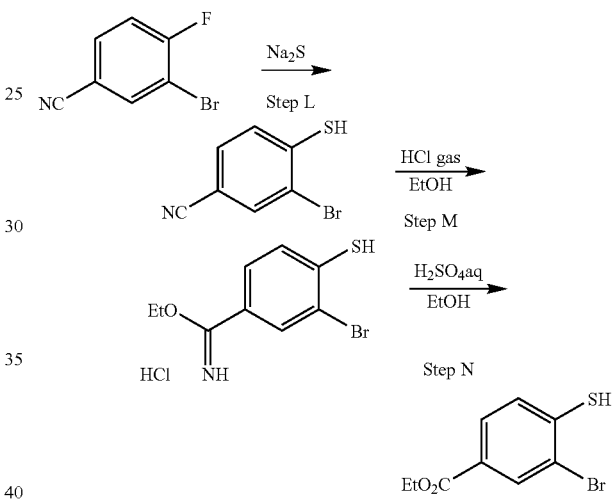

Step L

3-Bromo-4-fluorobenzonitrile (100 g) was dissolved in dimethylformamide (DMF) (500 ml), and sodium sulfide nonahydrate (132 g) was added thereto at 0° C. and then stirred overnight at room temperature. The reaction mixture was poured to ice water (1 L) and the insoluble material was filtered off. The filtrate was added to a 1N aqueous hydrochloric acid solution (700 ml) under ice-cooling and the precipitate was collected by filtration. The crystals thus obtained were washed with hexane/diisopropyl ether and water and then dried to obtain 3-bromo-4-mercaptobenzonitrile (95.0 g) as a light-yellow solid.

$^1$H-NMR (400M, DMSO-d6) δ
7.72 (s, 2H), 8.14 (s, 1H).

Step M

3-Bromo-4-mercaptobenzonitrile (10 g) was dissolved in toluene (50 ml) and chloroform (80 ml), followed by adding thereto ethanol (3.0 ml), and the resulting mixture was cooled to −10° C. Hydrochloric acid gas was bubbled into the mixture through a bubbler for 10 minutes and the resulting mixture was stirred at the same temperature for 30 minutes. The reaction mixture was allowed to stand in a refrigerator for 60 hours and then the completion of the reaction was confirmed by HPLC(ODS-A212). Dry nitrogen was bubbled into the reaction solution through a bubbler for 20 minutes and the hydrochloric acid gas was distilled off. The precipitate was collected by filtration, washed with toluene/chloroform and then dried to obtain ethyl 3-bromo-4-mercaptobenzene-carboximidate (13.6 g) as a light-yellow solid.

$^1$H-NMR (400M, DMSO-d6) δ

1.47 (t, J=7.0 Hz, 3H), 4.59 (q, J=7.0 Hz, 2H), 7.83-7.90 (m, 2H), 7.92-7.88 (m, 2H), 8.32 (s, 2H).

Step N

Ethyl 3-bromo-4-mercaptobenzenecarboximidate (3.00 g) was dissolved in ethanol (100 ml), and water (10 ml) and then concentrated sulfuric acid (10 ml) were added dropwise thereto at 0° C. and stirred overnight at room temperature. Zinc (1 g) was added to the reaction system and the resulting mixture was stirred at room temperature for 2 hours to induce the production of a monomer. After the zinc powder was removed by filtration through Celite, the ethanol was distilled off under reduced pressure, followed by extraction with ethyl acetate, and the organic layer was washed with water (×4). The organic layer was dried over anhydrous sodium sulfate and then concentrated to obtain ethyl 3-bromo-4-mercaptobenzoate (2.58 g) as a light-yellow solid.

$^1$H-NMR (400M, CDCl$_3$) δ

1.39 (t, J=7.2 Hz, 3H), 4.20 (s, 1H), 4.36 (q, J=7.1 Hz, 2H), 7.38 (d, J=8.2 Hz, 1H), 7.82 (dd, J=8.2, 1.8 Hz, 1H), 8.18 (d, J=1.8 Hz, 1H).

Reference Example 7

{(2S)-6-(Ethoxycarbonyl)-2-[3-(4-methoxyphenyl)propyl]-3-oxo-2,3-dihydro-4H-1,4-benzothiazin-4-yl}acetic acid

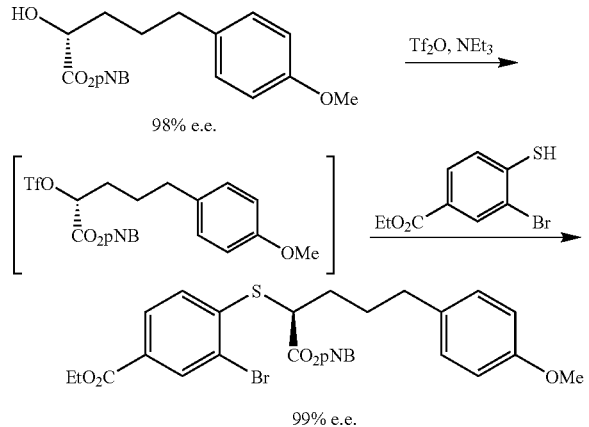

The 4-nitrobenzyl (2R)-2-hydroxy-5-(4-methoxyphenyl)pentanoate (5.43 g) described in Reference Example 5 was dissolved in acetonitrile (20 ml), followed by adding thereto trifluoroacetic anhydride (5.1 ml) and then triethylamine (4.2 ml) at −30 to −20° C., and the resulting mixture was allowed to warm to room temperature spontaneously. After 30 minutes, the reaction mixture was poured into a saturated aqueous ammonium chloride solution and extracted with ethyl acetate, and the organic layer was washed with a saturated aqueous sodium hydrogencarbonate solution and a saturated aqueous sodium chloride solution and dried over anhydrous sodium sulfate. After the drying agent was removed by filtration, the solvent was distilled off under reduced pressure and the residue was dissolved in acetonitrile (20 ml). The compound described in Reference Example 6 (ethyl 3-bromo-4-mercaptobenzoate (4.14 g, 15.7 mmol)) and then pyridine (1.28 ml, 15.7 mmol) were added thereto under ice-cooling. After 15 minutes, the resulting mixture was warmed up to room temperature. After 1 hour, the reaction mixture was poured into a saturated aqueous ammonium chloride solution and extracted with ethyl acetate. The organic layer was washed with a saturated aqueous sodium chloride solution and then dried over anhydrous sodium sulfate. The drying agent was removed by filtration and the solvent was distilled off under reduced pressure. The residue was purified by a silica gel column chromatography (hexane/ethyl acetate=4/1) to obtain ethyl 3-bromo-4-[((1S)-4-(4-methoxyphenyl)-1-{[(4-nitrobenzyl)oxy]carbonyl}-butyl)thio]benzoate (6.89 g) having an optical purity of 99% e.e. The optical purity analysis conditions are as follows. [Optical purity analysis conditions: column=OJ-R (Chiralcel, DAICEL Chemical Industries Ltd.); detecting wavelength (UV)=254 nm; flow rate: 1.0 ml/min; mobile phase=acetonitrile/water (68/32)]

$^1$H-NMR (CDCl$_3$) δ

1.39 (t, J=7.1 Hz, 3H), 1.65-1.87 (m, 2H), 1.93 (m, 1H), 2.05 (m, 1H), 2.61 (m, 1H), 3.79 (s, 3H), 3.95 (t, J=6.9 Hz, 1H), 4.37 (q, J=7.1 Hz, 2H), 5.17 (d, J=2.2 Hz, 2H), 6.79-6.83 (m, 2H), 7.04-7.09 (m, 2H), 7.30-7.38 (m, 3H), 7.78 (dd, J=8.3, 1.8 Hz, 1H), 8.10-8.18 (m, 3H).

Reference Example 8

(2S)-2-{[2-Bromo-4-(ethoxycarbonyl)phenyl]thio}-5-(4-methoxyphenyl)pentanoic acid

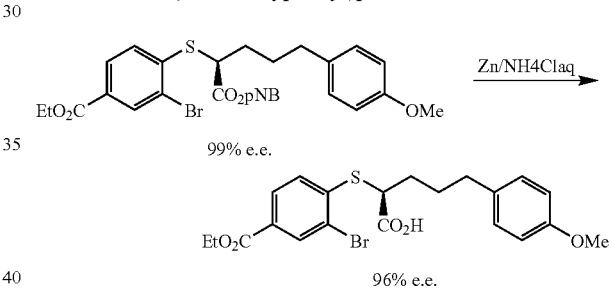

Zinc (3.73 g) and ammonium chloride (3.69 g) were added to water (34.5 ml), and a solution of the compound of Reference Example 7 (6.89 g, 99% e.e.) in THF (30 ml) was added dropwise thereto under ice-cooling. After completion of the dropwise addition, the resulting mixture was warmed up to room temperature and stirred for 6 hours. Ethyl acetate and water were added to the reaction mixture and the resulting mixture was filtered through Celite. The organic layer was washed with a 1N aqueous hydrochloric acid solution and a saturated aqueous sodium chloride solution and dried over anhydrous sodium sulfate. The drying agent was removed by filtration and the solvent was distilled off under reduced pressure. The thus obtained (2S)-2-{[2-bromo-4-(ethoxycarbonyl)phenyl]thio}-5-(4-methoxyphenyl)pentanoic acid (96% e.e.) was used in a subsequent step. The optical purity analysis conditions are as follows. [Optical purity analysis conditions: column=AD-H (Chiralcel, DAICEL Chemical Industries Ltd.); detecting wavelength (UV)=254 nm; flow rate: 1.0 ml/min; mobile phase=n-hexane/isopropyl alcohol/TFA (90/10/0.1)]

$^1$H-NMR (CDCl$_3$) δ: 1.38 (t, J=7.1 Hz, 3H), 1.75-1.96 (m, 3H), 2.03 (m, 1H), 2.62 (t, J=7.3 Hz, 2H), 3.78 (s, 3H), 3.85 (t, J=7.1 Hz, 1H), 4.37 (q, J=7.1 Hz, 2H), 6.79-6.83 (m, 2H), 7.08-7.10 (m, 2H), 7.41 (d, J=8.3 Hz, 1H), 7.90 (dd, J=8.3, 1.8 Hz, 1H), 8.18 (d, J=1.8 Hz, 1H).

Reference Example 9

Ethyl 3-bromo-4-({(1S)-4-(4-methoxyphenyl)-1-[(t-butoxycarbonylmethylamino)carbonyl]butyl}thio)benzoate

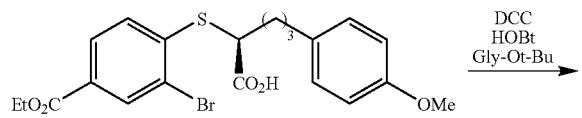

96% e.e.

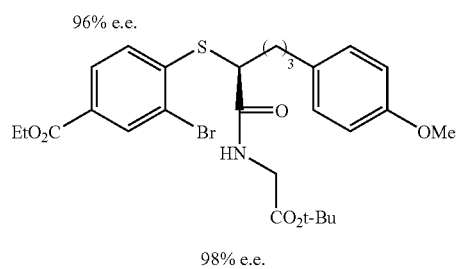

98% e.e.

Glycine tert-butyl ester hydrochloride (2.03 g) and dicyclohexylcarbodiimide (DCC) (2.5 g) were added to a solution of (2S)-2-{[2-bromo-4-(ethoxycarbonyl)phenyl]thio}-5-(4-methoxyphenyl)pentanoic acid (the compound of Reference Example 8) (96% e.e.) in dichloromethane (56.4 ml) at −5° C., and N-methylmorpholine (1.26 ml) was added dropwise thereto. After stirring at the same temperature for 1.5 hours, water was added thereto and the resulting mixture was filtered through Celite. The filtrate was extracted with chloroform and the extract solution was washed with a saturated aqueous ammonium chloride solution and a saturated aqueous sodium chloride solution and then dried over anhydrous sodium sulfate. The drying agent was removed by filtration and the solvent was distilled off under reduced pressure. The residue was purified by a silica gel column chromatography (hexane/ethyl acetate=3/1) to obtain ethyl 3-bromo-4-({(1S)-4-(4-methoxyphenyl)-1-[(tert-butoxycarbonylmethylamino)carbonyl]butyl}thio)benzoate (4.83 g, 98% e.e.). The optical purity analysis conditions are as follows. [Optical purity analysis conditions: column=AD-H (Chiralpak, DAICEL Chemical Industries Ltd.); detecting wavelength (UV)=254 nm; flow rate: 1.0 ml/min; mobile phase=n-hexane/isopropyl alcohol/TFA (90/10/0.1)]

$^1$H-NMR (CDCl$_3$) δ: 1.38 (t, J=7.1 Hz, 3H), 1.42 (s, 9H), 1.79-1.98 (m, 3H), 2.09 (m, 1H), 2.62 (t, J=7.3 Hz, 2H), 3.77 (dd, J=18.2, 4.9 Hz, 1H), 3.78 (s, 3H), 3.85 (t, J=6.9 Hz, 1H), 3.94 (dd, J=18.2, 5.6 Hz, 1H), 4.36 (q, J=7.1 Hz, 2H), 6.79-6.83 (m, 2H), 6.95 (m, 1H), 7.08-7.12 (m, 2H), 7.22 (d, J=8.4 Hz, 1H), 7.88 (dd, J=8.3, 1.8 Hz, 1H), 8.18 (d, J=1.8 Hz, 1H).

Reference Example 10

Ethyl (2S)-4-(2-tert-butoxy-2-oxoethyl)-2-[3-(4-methoxyphenyl)propyl]-3-oxo-3,4-dihydro-2H-1,4-benzothiazine-6-carboxylate

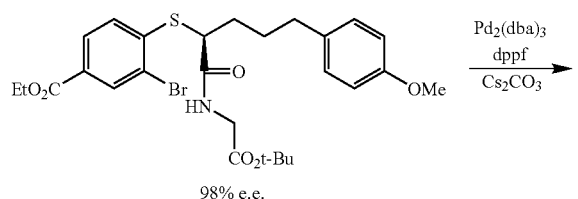

98% e.e.

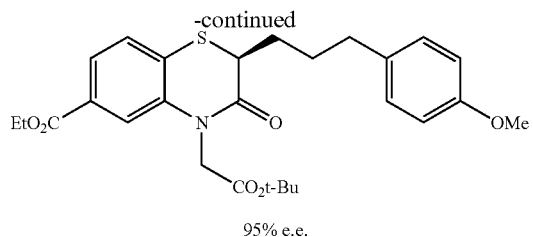

95% e.e.

The compound of Reference Example 9 (4.83 g, 98% e.e.) was dissolved in toluene (161 ml), and 1,1'-bis(diphenylphosphino)ferrocene (DPPF, 889 mg) and cesium carbonate (2.61 g) were added thereto. After the resulting mixture was treated with nitrogen to replace the air, tris(dibenzylideneacetone)palladium(0) (Pd$_2$(dba)$_3$, 366 mg) was added thereto, and the resulting mixture was stirred at 120° C. After 5 hours, the reaction mixture was cooled to room temperature and filtered through Celite. The filtrate was poured into a saturated aqueous ammonium chloride solution and extracted with ethyl acetate. The organic layer was washed with a saturated aqueous sodium chloride solution and then dried over anhydrous magnesium sulfate. The drying agent was removed by filtration and the residue was purified by a silica gel column chromatography (hexane/ethyl acetate=5/1) to obtain ethyl (2S)-4-(2-tert-butoxy-2-oxoethyl)-2-[3-(4-methoxyphenyl)propyl]-3-oxo-3,4-dihydro-2H-1,4-benzothiazine-6-carboxylate (2.37 g, 95% e.e.). The optical purity analysis conditions are as follows. [Optical purity analysis conditions: column=OD-RH (Chiralcel, DAICEL Chemical Industries Ltd.); detecting wavelength (UV)=254 nm; flow rate: 1.0 ml/min; mobile phase=acetonitrile/water (60/40)]

$^1$H-NMR (CDCl$_3$) δ: 1.38 (t, J=7.1 Hz, 3H), 1.49 (s, 9H), 1.60 (m, 1H), 1.71 (m, 1H), 1.75-1.98 (m, 2H), 2.54 (m, 2H), 3.48 (m, 1H), 3.76 (s, 3H), 4.32-4.41 (m, 3H), 4.82 (m, 1H), 6.76-6.80 (m, 2H), 7.02-7.06 (m, 2H), 7.40 (m, 1H), 7.50 (m, 1H), 7.70 (m, 1H).

Reference Example 11

{(2S)-6-(Ethoxycarbonyl)-2-[3-(4-methoxy-phenyl)propyl]-3-oxo-2,3-dihydro-4H-1,4-benzothiazin-4-yl}acetic acid

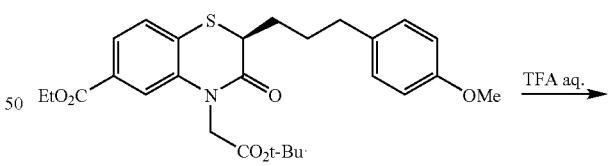

95% e.e.

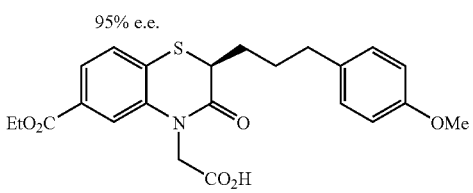

Water (6.25 ml) was added to a solution of the compound of Reference Example 10 (2.57 g, 95% e.e.) in TFA (25 ml) under ice-cooling. After 5 minutes, the resulting mixture was warmed up to room temperature and stirred for 1.5 hours. Toluene (60 ml) was added to the reaction solution and distilled off under reduced pressure. Toluene and water were added to the residue to effect separation into two layers, and the organic layer was washed with a saturated aqueous sodium chloride solution and then dried over anhydrous sodium sulfate. The drying agent was removed by filtration and the solvent was distilled off under reduced pressure to obtain {(2S)-6-(ethoxycarbonyl)-2-[3-(4-methoxyphenyl)propyl]-3-oxo-2,3-dihydro-4H-1,4-benzothiazin-4-yl}acetic acid (2.06 g).

$^1$H-NMR (CDCl$_3$) δ: 1.39 (t, J=7.2 Hz, 3H), 1.60 (m, 1H), 1.70 (m, 1H), 1.75-1.93 (m, 2H), 2.52 (m, 2H), 3.50 (m, 1H), 3.77 (s, 3H), 4.38 (q, J=7.2 Hz, 2H), 4.59 (m, 1H), 4.92 (m, 1H), 6.76-6.80 (m, 2H), 7.00-7.04 (m, 2H), 7.41 (d, J=8.1 Hz, 1H), 7.55 (m, 1H), 7.71 (m, 1H).

Reference Example 12

(+)-Ethyl 4-[2-(hydroxyamino)-2-oxoethyl]-2-[3-(4-methoxyphenyl)propyl]-3-oxo-3,4-dihydro-2H-1,4-benzothiazine-6-carboxylate

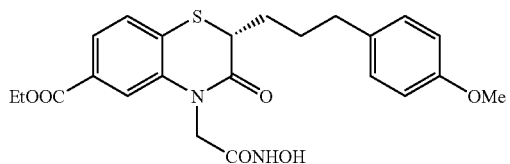

Using 4-nitrobenzyl (2S)-2-hydroxy-5-(4-methoxyphenyl)pentanoate, (+)-ethyl 4-[2-(hydroxyamino)-2-oxoethyl]-2-[3-(4-methoxyphenyl)propyl]-3-oxo-3,4-dihydro-2H-1,4-benzothiazine-6-carboxylate having an optical purity of 99.9% e.e. was synthesized by the same process as described in Example 7. The optical purity was determined by the method described in Example 7. $[\alpha]_D^{20}$=+86.1° (c: 1.0, CHCl$_3$)

$^1$H-NMR (CDCl$_3$) δ: 1.40 (t, J=7.2 Hz, 3H), 1.59 (m, 1H), 1.67 (m, 1H), 1.77-1.93 (m, 2H), 2.54 (m, 2H), 3.47 (m, 1H), 3.77 (s, 3H), 4.38 (q, J=7.2 Hz, 2H), 4.51 (d, J=16.0 Hz, 1H), 4.68 (d, J=16.0 Hz, 1H), 6.80 (m, 2H), 7.04 (m, 2H), 7.41 (d, J=8.0 Hz, 1H), 7.52 (br, 1H), 7.73 (m, 1H), 7.98 (br, 1H), 9.16 (br, 1H).

Reference Example 13

(+)-4-[2-(Hydroxyamino)-2-oxoethyl]-2-[3-(4-methoxyphenyl)propyl]-3-oxo-3,4-dihydro-2H-1,4-benzothiazine-6-carboxylic acid

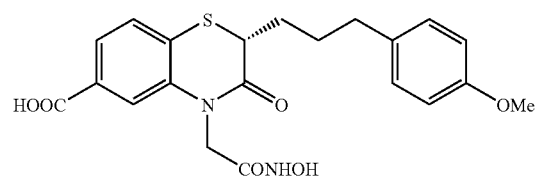

Using the compound of Reference Example 12, (+)-4-[2-(hydroxyamino)-2-oxoethyl]-2-[3-(4-methoxyphenyl)propyl]-3-oxo-3,4-dihydro-2H-1,4-benzothiazine-6-carboxylic acid (99% e.e.) was obtained by a process similar to the process described in Example 14. The optical purity was determined by the method described in Example 14.

$^1$H-NMR (DMSO-d6) δ 1.43 (m, 1H), 1.66 (m, 3H), 2.45 (m, 2H), 3.69 (s, 3H), 4.38 (d, J=16.8 Hz, 1H), 4.54 (d, J=16.8 Hz, 1H), 6.80 (m, 2H), 7.05 (m, 2H), 7.51 (m, 1H), 7.58-7.60 (m, 2H), 9.02+9.43 (s, 1H), 10.36+10.81 (s, 1H), 13.20 (brs, 1H).

Reference Example 14

Ethyl (2R)-4-(2-tert-butoxy-2-oxoethyl)-2-[3-(4-methoxyphenyl)propyl]-3-oxo-3,4-dihydro-2H-1,4-benzothiazine-6-carboxylate

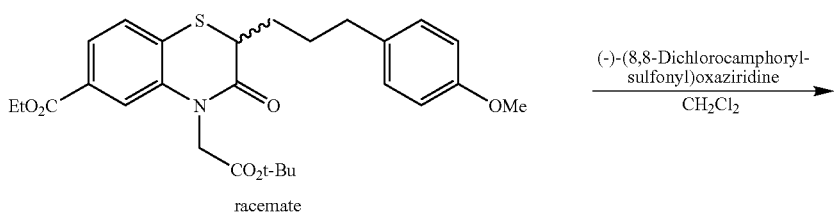

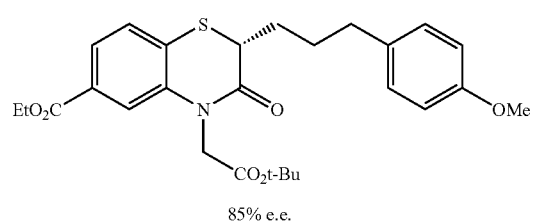

85% e.e.

The compound obtained in step B in Example 1 (62 mg) was dissolved in methylene chloride (2.5 ml), followed by adding (−)-(8,8-dichlorocamphorylsulfonyl) oxaziridine (37 mg), and the resulting mixture was stirred at room temperature for 10 days. The reaction mixture was poured into a saturated aqueous sodium chloride solution and extracted with ethyl acetate. The organic layer was collected, dried over anhydrous magnesium sulfate and then concentrated with an evaporator. The residue was purified by a silica gel flash chromatography (hexane/ethyl acetate=4/1) to obtain ethyl (2R)-4-(2-tert-butoxy-2-oxoethyl)-2-[3-(4-methoxyphenyl) propyl]-3-oxo-3,4-dihydro-2H-1,4-benzothiazine-6-carboxylate (15 mg, 85% e.e.) as a light-yellow oil. The optical purity was determined by the method described in Reference Example 10.

Reference Example 15

(+)-Ethyl 4-[2-(hydroxyamino)-2-oxoethyl]-2-[3-(4-methoxyphenyl)propyl]-3-oxo-3,4-dihydro-2H-1,4-benzothiazine-6-carboxylate

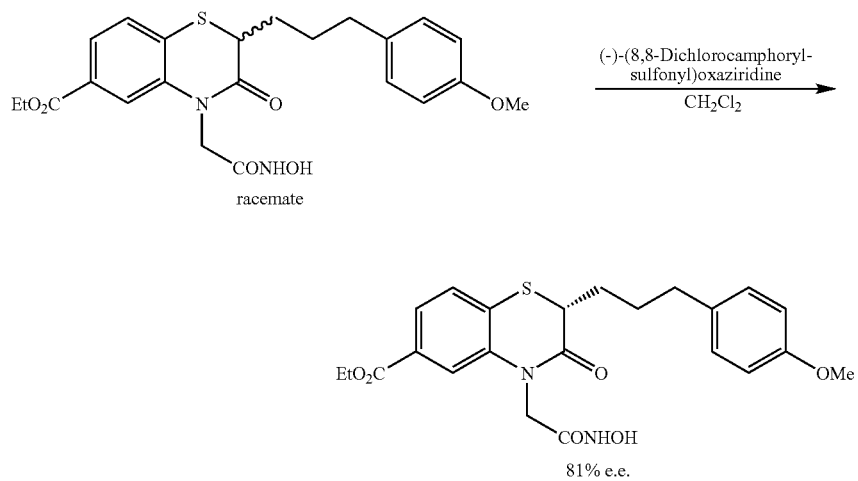

Using the compound of Example 1, the compound of Reference Example 12 (17% and 81% e.e.) was obtained by the same process as described in Reference Example 14. The optical purity was determined by the method described in Example 7.

Reference Example 16

(−)-4-[2-(Hydroxyamino)-2-oxoethyl]-2-[3-(4-methoxyphenyl)propyl]-3-oxo-3,4-dihydro-2H-1,4-benzothiazine-6-carboxylic acid

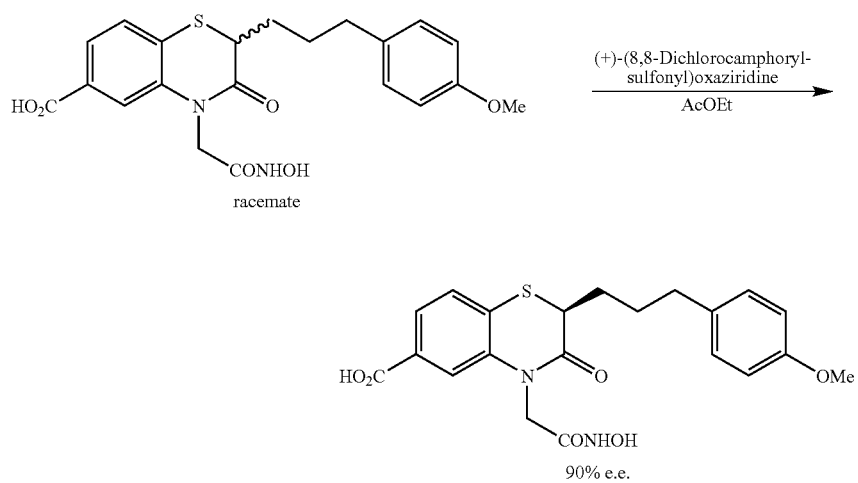

The compound of Example 14 (25% and 90% e.e.) was obtained by the same process as described in Reference Example 14, except for using the compound of Example 8, (+)-(8,8-dichlorocamphorylsulfonyl)oxaziridine and ethyl acetate as solvent. The optical purity was determined by the method described in Example 14.

Reference Example 17

Ethyl (2E,4E)-5-(4-methoxyphenyl)penta-2,4-dienoate

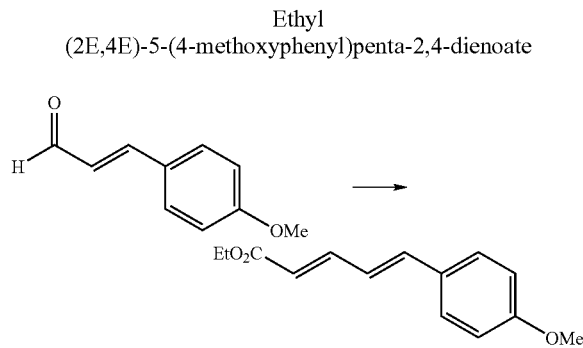

After NaH (2.7 g, 60%) was washed with hexane, tetrahydrofuran (100 ml) was added thereto. The reaction mixture was cooled to 0° C. and then triethyl phosphonoacetate (14.7 ml) was added dropwise thereto. After 30 minutes, the resulting mixture was warmed up to room temperature and stirred for another 30 minutes. The reaction mixture was cooled to 0° C. again and a solution of the compound obtained in Reference Example 1 (10 g) in tetrahydrofuran (50 ml) was added dropwise thereto. After 30 minutes, a saturated aqueous ammonium chloride solution was added thereto, followed by extraction with ethyl acetate. The organic layer was washed with water, dried, and then concentrated, and the residue was crystallized from ethanol-hexane. The crystals were filtered and then dried to obtain ethyl (2E,4E)-5-(4-methoxyphenyl)penta-2,4-dienoate (11.5 g).

$^1$H-NMR (CDCl$_3$) δ

1.31 (t, J=7.1 Hz, 3H), 3.83 (s, 3H), 4.22 (q, J=7.1 Hz, 2H), 5.94 (d, J=15.2 Hz, 1H), 6.75 (dd, J=15.2, 10.7 Hz, 1H), 6.82-6.93 (m, 3H), 7.38-7.48 (m, 3H).

Reference Example 18

5-(4-Methoxyphenyl)pentanoic acid

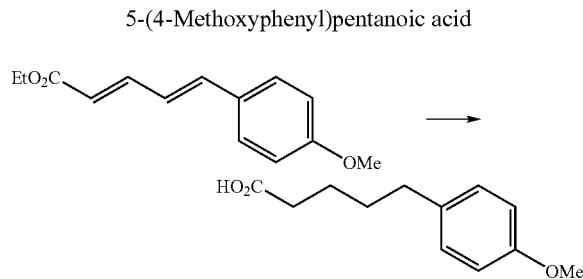

The compound obtained in Reference Example 17 (11.5 g), tetrahydrofuran (150 ml) and 10% Pd—C (1.5 g) were mixed and then stirred under a hydrogen atmosphere. After 3 hours, the reaction mixture was filtered through Celite and the filtrate was concentrated. Ethanol (150 ml) and a 1N aqueous potassium hydroxide solution (50 ml) were added to the residue and the resulting mixture was stirred with heating at 70° C. for 30 minutes. Water was added thereto and the ethanol was concentrated. The thus obtained solution was acidified with a 1N aqueous hydrochloric acid solution and the precipitate formed was filtered and then dried to obtain 5-(4-methoxyphenyl)pentanoic acid (10.2 g).

$^1$H-NMR (CDCl$_3$) δ

1.59-1.73 (m, 4H), 2.35-2.41 (m, 2H), 2.55-2.63 (m, 2H), 3.79 (s, 3H), 6.83 (m, 2H), 7.09 (m, 2H).

Reference Example 19

(4R)-4-Benzyl-3-[5-(4-methoxyphenyl)pentanoyl]-1,3-oxazolidin-2-one

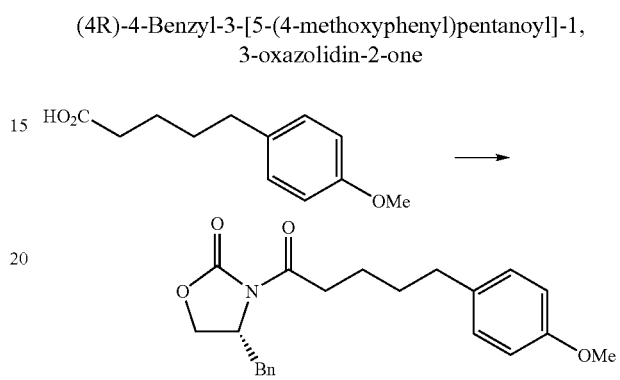

5-(4-Methoxyphenyl)pentanoic acid (the compound obtained in Reference Example 18) (6.2 g) was dissolved in dichloromethane (60 ml), and oxalyl chloride (3.1 ml) and DMF (a drop) were added thereto at room temperature. After 1 hour, the reaction mixture was concentrated, dried under reduced pressure and then dissolved in tetrahydrofuran (20 ml) to obtain a solution named A.

(R)-4-Benzyl-2-oxazolidinone (6.4 g) was dissolved in tetrahydrofuran (80 ml) and the resulting solution was cooled to −78° C., followed by adding dropwise thereto n-butyllithium (1.58M, 23 ml). The resulting mixture was stirred for 1 hour and then the solution A prepared as above was added dropwise thereto. After 30 minutes, the resulting mixture was warmed up to 0° C. and stirred for another 30 minutes. After the reaction was quenched with a saturated aqueous ammonium chloride solution, the reaction mixture was extracted with ethyl acetate. The organic layer was washed with water, dried and then concentrated, and the residue was purified by a silica gel chromatography (300 g, ethyl acetate:hexane=1:3) to obtain (4R)-4-benzyl-3-[5-(4-methoxyphenyl)pentanoyl]-1,3-oxazolidin-2-one (9.0 g).

$^1$H-NMR (CDCl$_3$) δ

1.63-1.79 (m, 4H), 2.57-2.65 (m, 2H), 2.75 (dd, J=13.3, 9.6 Hz, 1H), 2.88-3.04 (m, 2H), 3.29 (dd, J=13.3, 3.3 Hz, 1H), 3.79 (s, 3H), 4.13-4.22 (m, 2H), 4.66 (m, 1H), 6.83 (m, 2H), 7.11 (m, 2H), 7.20 (m, 2H), 7.25-7.36 (m, 3H).

Reference Example 20

(4R)-3-[5-(4-Methoxyphenyl)pentanoyl]-4-phenyl-1,3-oxazolidin-2-one

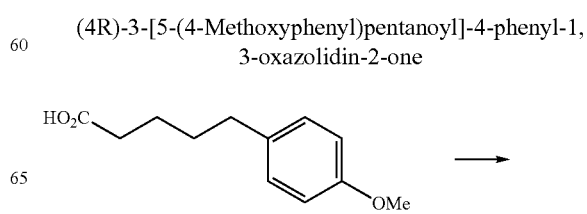

-continued

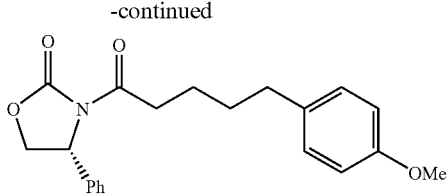

(4R)-3-[5-(4-Methoxyphenyl)pentanoyl]-4-phenyl-1,3-oxazolidin-2-one (2.6 g) was obtained from 5-(4-methoxyphenyl)pentanoic acid (2 g) and (R)-4-phenyl-2-oxazolidinone (1.6 g) by a process similar to the process described in Reference Example 19.

$^1$H-NMR (CDCl$_3$) δ

1.55-1.70 (m, 4H), 2.54 (t, J=6.8 Hz, 2H), 2.95 (t, J=7.5 Hz, 2H), 3.78 (s, 3H), 4.27 (dd, J=8.9, 3.7 Hz, 1H), 4.68 (t, J=8.9 Hz, 1H), 5.41 (dd, 1H, J=8.9, 3.7 Hz, 1H), 6.80 (m, 2H), 7.05 (m, 2H), 7.26 (m, 5H).

Reference Example 21

(4R)-4-Benzyl-3-[(2R)-2-bromo-5-(4-methoxyphenyl)pentanoyl]-1,3-oxazolidin-2-one

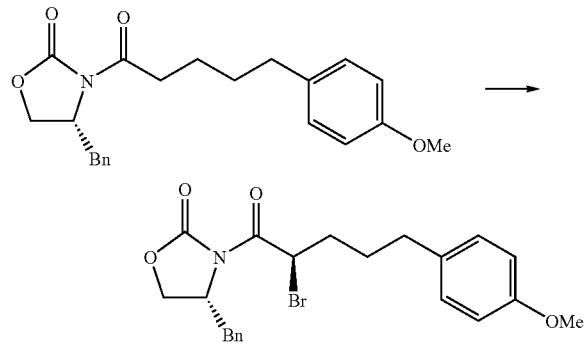

(4R)-4-Benzyl-3-[5-(4-methoxyphenyl)pentanoyl]-1,3-oxazolidin-2-one (Reference Example 19) (1.4 g) was dissolved in dichloromethane (25 ml), and dibutylborane triflate (1M, 8.3 ml) and diisopropylethylamine (1.6 ml) were added thereto under ice-cooling. After 30 minutes, the reaction mixture was cooled to −78° C. and added dropwise to a solution of N-bromosuccinimide (NBS) (1.1 g) in dichloromethane (25 ml) which had been cooled to −78° C., via a cannula. After 2 hours, an aqueous sodium sulfite solution was added thereto and the resulting mixture was stirred at room temperature for 30 minutes. Chloroform was added to the reaction mixture to effect separation and extraction. The organic layer was dried, concentrated, and then the residue was purified by a silica gel chromatography (150 g, ethyl acetate hexane=1:4) to obtain (4R)-4-benzyl-3-[(2R)-2-bromo-5-(4-methoxyphenyl)pentanoyl]-1,3-oxazolidin-2-one (0.9 g).

$^1$H-NMR (CDCl$_3$) δ

1.62-1.89 (m, 2H), 2.04-2.22 (m, 2H), 2.56-2.70 (m, 2H), 2.79 (dd, J=13.5, 9.5 Hz, 1H), 3.29 (dd, J=13.5, 3.3 Hz, 1H), 3.78 (s, 3H), 4.20-4.23 (m, 2H), 4.68 (m, 1H), 5.63 (t, J=6.8 Hz, 1H), 6.83 (m, 2H), 7.10 (m, 2H), 7.22-7.38 (m, 5H).

Reference Example 22

Ethyl 4-{[(1S)-1-{[(4R)-4-benzyl-2-oxo-1,3-oxazolidin-3-yl]carbonyl}-4-(4-methoxyphenyl)butyl]thio}-3-nitrobenzoate

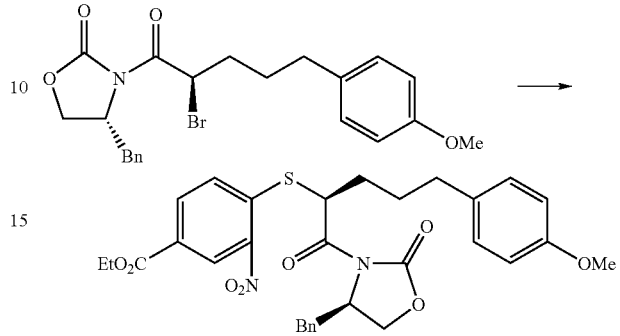

Diethyl 4,4'-dithiobis(3-nitrobenzoate) (0.64 g) was dissolved in tetrahydrofuran (10 ml), and dithiothreitol (0.24 g) and N-methylmorpholine (0.21 ml) were added thereto at room temperature. After 40 minutes, the reaction mixture was cooled to 0° C. and a solution of (4R)-4-benzyl-3-[(2R)-2-bromo-5-(4-methoxyphenyl)pentanoyl]-1,3-oxazolidin-2-one (Reference Example 21) (0.7 g) in tetrahydrofuran (10 ml) was slowly added dropwise thereto. After 2 hours, the reaction was quenched by the addition of a 1N aqueous hydrochloric acid solution (20 ml) and the reaction mixture was extracted with ethyl acetate. The organic layer was washed with a saturated aqueous sodium hydrogencarbonate solution, water and a saturated aqueous sodium chloride solution, dried, concentrated, and then the residue was purified by a silica gel chromatography (150 g, ethyl acetate:hexane=1:4) to obtain ethyl 4-{[(1S)-1-{[(4R)-4-benzyl-2-oxo-1,3-oxazolidin-3-yl]carbonyl}-4-(4-methoxyphenyl)butyl]thio}-3-nitrobenzoate (0.7 g).

$^1$H-NMR (CDCl$_3$) δ

1.42 (t, J=7.1 Hz, 3H), 1.78-2.00 (m, 3H), 2.19 (m, 1H), 2.64 (m, 1H), 2.74 (dd, J=13.3, 9.7 Hz, 1H), 3.30 (dd, J=13.3, 3.3 Hz, 1H), 3.79 (s, 3H), 4.19-4.30 (m, 2H), 4.42 (q, J=7.1 Hz, 2H), 4.70 (m, 1H), 5.53 (t, J=7.3 Hz, 1H), 6.82 (m, 2H), 7.10 (m, 2H), 7.19 (m, 2H), 7.25-7.35 (m, 3H), 7.48 (d, J=8.5 Hz, 1H), 8.11 (dd, J=8.5, 1.9 Hz, 1H), 8.73 (d, J=1.9 Hz, 1H).

Reference Example 23

Ethyl (2S)-2-[3-(4-methoxyphenyl)propyl]-3-oxo-3,4-dihydro-2H-1,4-benzothiazine-6-carboxylate

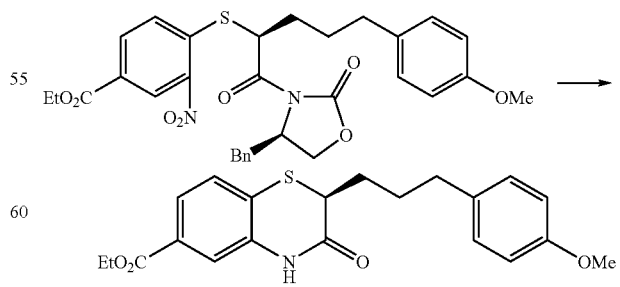

Ethyl 4-{[(1S)-1-{[(4R)-4-benzyl-2-oxo-1,3-oxazolidin-3-yl]carbonyl}-4-(4-methoxyphenyl)butyl]thio}-3-3-nitrobenzoate (Reference Example 22) (0.62 g, 0.11 mmol), ethanol (10 ml), acetic acid (5 ml) and 10% Pd—C (1.5 g) were mixed, and the mixture was stirred for 3 hours at room temperature under a hydrogen atmosphere. The reaction mixture was filtered through Celite and the filtrate was concentrated. The residue was purified by a silica gel chromatography (40 g, ethyl acetate:hexane=1:3) to obtain ethyl (2S)-2-[3-(4-methoxyphenyl)propyl]-3-oxo-3,4-dihydro-2H-1,4-benzothiazine-6-carboxylate (0.2 g, 98.3% e.e.), i.e., the compound described in Example 7.

The optical purity analysis conditions are as follows:

Column: AD-H (Chiralcel, DAICEL Chemical Industries Ltd.)

Detecting wavelength (UV): 254 nm

Flow rate: 1.0 ml/min

Mobile phase=n-hexane/isopropyl alcohol/TFA=80/20/0.1

$^1$H-NMR (CDCl$_3$) δ

1.40 (t, J=7.1 Hz, 3H), 1.60-1.75 (m, 2H), 1.80-1.98 (m, 2H), 2.56 (m, 2H), 3.44 (m, 1H), 3.77 (s, 3H), 4.38 (q, J=7.1 Hz, 2H), 6.78-6.82 (m, 2H), 7.03-7.08 (m, 2H), 7.35 (d, J=8.1 Hz, 1H), 7.55 (d, J=1.5 Hz, 1H), 7.67 (dd, J=8.1, 1.5 Hz, 1H), 8.52 (s, 1H).

Reference Example 24

(4R)-3-[(2R)-2-Hydroxy-5-(4-methoxyphenyl)pentanoyl]-4-phenyl-1,3-oxazolidin-2-one

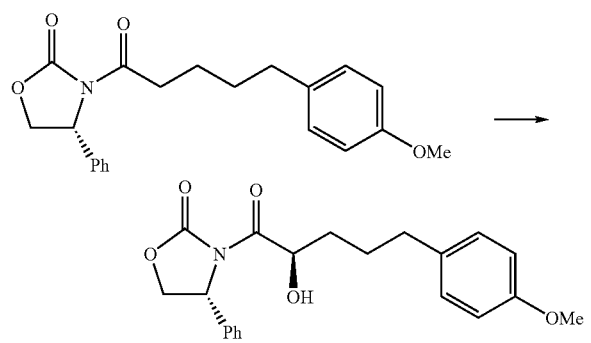

(4R)-3-[5-(4-Methoxyphenyl)pentanoyl]-4-phenyl-1,3-oxazolidin-2-one (Reference Example 20) (1.0 g) was dissolved in tetrahydrofuran (10 ml) and the resulting solution was cooled to −78° C., followed by adding thereto sodium hexamethyldisilazide (1M, 3.4 ml). After 30 minutes, a solution of Davis reagent (0.9 g) in tetrahydrofuran (5 ml) was added dropwise thereto. After stirring for 1 hour, a solution of camphorsulfonic acid (1.5 g) in tetrahydrofuran (5 ml) was added thereto and stirred for 30 minutes. Ethyl acetate and water were added to the reaction mixture to effect separation and extraction. The organic layer was washed with a saturated aqueous sodium hydrogencarbonate solution, water and a saturated aqueous sodium chloride solution, dried, concentrated, and then the residue was purified by a silica gel chromatography (100 g, ethyl acetate:hexane=1:3) to obtain (4R)-3-[(2R)-2-hydroxy-5-(4-methoxyphenyl)pentanoyl]-4-phenyl-1,3-oxazolidin-2-one (0.75 g).

$^1$H-NMR (CDCl$_3$) δ

1.59 (m, 1H), 1.75-1.92 (m, 3H), 2.60 (m, 2H), 3.78 (s, 3H), 4.35 (dd, J=8.7, 3.2 Hz, 1H), 4.75 (t, J=8.7 Hz, 1H), 5.01 (dd, J=8.1, 3.2 Hz, 1H), 5.38 (dd, J=8.7, 3.2 Hz, 1H), 6.82 (m, 2H), 7.10 (m, 2H), 7.26-7.42 (m, 5H).

Reference Example 25

Methyl (2R)-2-hydroxy-5-(4-methoxyphenyl)pentanoate

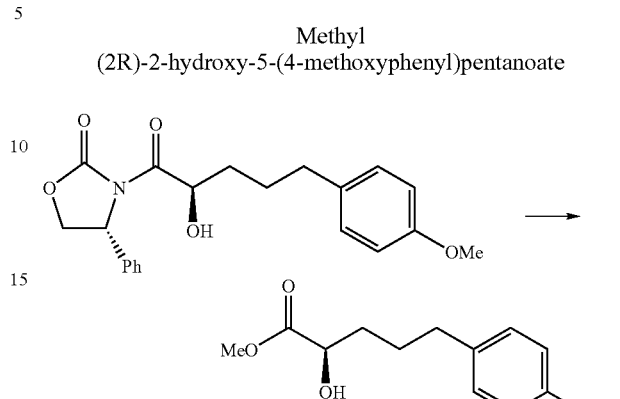

(4R)-3-[(2R)-2-Hydroxy-5-(4-methoxyphenyl)pentanoyl]-4-phenyl-1,3-oxazolidin-2-one (Reference Example 24) (0.23 g) was dissolved in methanol (3 ml), and sodium methoxide (a 1.2M methanol solution, 1 ml) was added thereto under ice-cooling. After 5 minutes, the reaction was quenched by adding a saturated aqueous ammonium chloride solution to the reaction mixture, and then the reaction mixture was extracted with ethyl acetate. The organic layer was washed with water, dried, concentrated, and then the residue was purified by a silica gel chromatography (20 g, ethyl acetate:hexane=1:3) to obtain methyl (2R)-2-hydroxy-5-(4-methoxyphenyl)pentanoate (0.06 g, 98% e.e.).

The optical purity analysis conditions are as follows:

Column: OD-H (Chiralcel, DAICEL Chemical Industries Ltd.)

Detecting wavelength (UV): 276 nm

Flow rate: 1.0 ml/min

Mobile phase=n-hexane/isopropyl alcohol=90/10

$^1$H-NMR (CDCl$_3$) δ

1.60-1.87 (m, 4H), 2.55-2.62 (m, 2H), 2.73 (br., 1H), 3.76 (s, 3H), 3.77 (s, 3H), 4.20 (m, 1H), 6.80-6.84 (m, 2H), 7.06-7.12 (m, 2H)

Reference Example 26

(2R)-2-Hydroxy-5-(4-methoxyphenyl)pentanoic acid

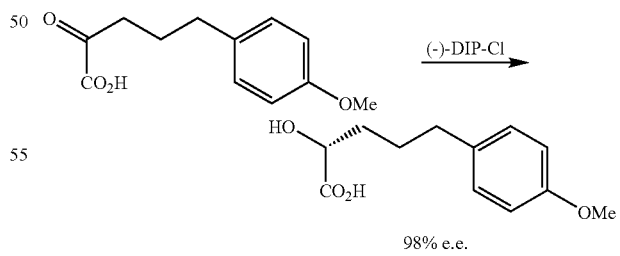

5-(4-Methoxyphenyl)-2-oxopentanoic acid (62.7 g) was dissolved in THF (1 L) and triethylamine (46.8 ml) was added thereto. A solution of (−)-DIP-Cl (100 g) in THF (600 ml) was added dropwise thereto while maintaining the temperature at −25° C. to −35° C. The resulting mixture was warmed up to room temperature and stirred for 2 hours, and then water (500 ml) was added thereto at 20° C. or lower. A 6N aqueous sodium hydroxide solution (120 ml) was added thereto and stirred for 15 minutes. Thereafter, diisopropyl ether (300 ml) was added thereto to effect separation into two layers. The aqueous layer was washed twice with diisopropyl ether (300 ml) and then a 6N aqueous hydrochloric acid solution was added thereto, followed by extraction with ethyl acetate. The organic layer was washed with a saturated aqueous sodium chloride solution and then dried over anhydrous sodium sulfate. The solvent was distilled off under reduced pressure to obtain a crude product. The crude product was dissolved in acetonitrile (640 ml), followed by adding thereto (+)-tolylethylamine (39 g), and the resulting mixture was heated under reflux to dissolve the amine completely. Crystals were precipitated at room temperature and collected by filtration. A 1N aqueous hydrochloric acid solution was added to the crystals obtained, followed by extraction with ethyl acetate. The organic layer was washed with a saturated aqueous sodium chloride solution and then dried over anhydrous sodium sulfate. The solvent was distilled off under reduced pressure and the residue was crystallized from a mixed solvent of diisopropyl ether and hexane (1/1) to obtain (2R)-2-hydroxy-5-(4-methoxyphenyl)pentanoic acid (29.8 g, 98% e.e.).

The optical purity was determined by the method described in Reference Example 4.

$^1$H NMR (300 MHz, CDCl$_3$) δ 1.70-1.89 (m, 4H), 2.60 (brt, J=6.6 Hz, 2H), 3.79 (s, 3H), 4.27-4.29 (m, 1H), 6.80-6.85 (m, 2H), 7.08-7.11 (m, 2H).

Reference Example 27

Methyl (2R)-2-hydroxy-5-(4-methoxyphenyl)pentanoate

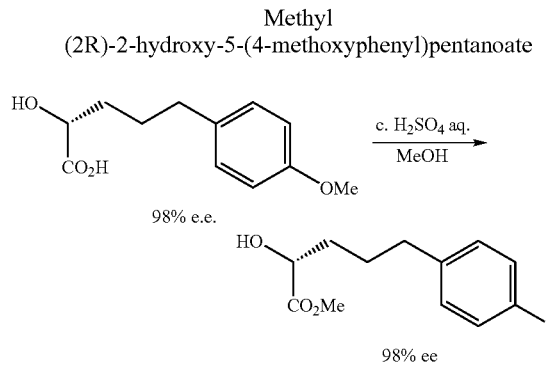

The compound obtained in Reference Example 26 (134 g, 98% e.e.) was dissolved in methanol (1072 ml), followed by adding thereto concentrated sulfuric acid (13.4 ml), and the resulting mixture was stirred at 60° C. for 1 hour. About one-half of the methanol was distilled off under reduced pressure and the residual reaction solution was poured into water (1 L). After extraction with ethyl acetate (600 ml+300 ml), the organic layer was washed with a saturated aqueous sodium hydrogencarbonate solution and a saturated aqueous sodium chloride solution and then dried over anhydrous sodium sulfate. The solvent was distilled off under reduced pressure to obtain methyl 2-hydroxy-5-(4-methoxyphenyl) pentanoate quantitatively (98% e.e.). The optical purity analysis conditions are as follows. [Optical purity analysis conditions: column=OD-H (Chiralcel, DAICEL Chemical Industries Ltd.); detecting wavelength (UV)=276 nm; flow rate: 1.0 ml/min; mobile phase=n-hexane/isopropyl alcohol (90/10)]

$^1$H-NMR (CDCl$_3$) δ

1.60-1.87 (m, 4H), 2.55-2.62 (m, 2H), 2.73 (br., 1H), 3.76 (s, 3H), 3.77 (s, 3H), 4.20 (m, 1H), 6.80-6.84 (m, 2H), 7.06-7.12 (m, 2H).

Reference Example 28

(2S)-2-Hydroxy-5-(4-methoxyphenyl)pentanoic acid

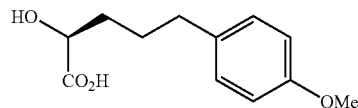

(2S)-2-Hydroxy-5-(4-methoxyphenyl)pentanoic acid was obtained by the same process as described in Reference Example 26, except for using (+)-DIP-Cl in place of (−)-DIP-Cl, and (−)-tolylethylamine in place of (+)-tolylethylamine. (The optical purity was 97% e.e.).

The optical purity was determined by the method described in Reference Example 4.

$^1$H-NMR (CDCl$_3$) δ

1.66-1.92 (m, 4H), 2.61 (m, 1H), 3.78 (s, 3H), 4.26 (m, 1H), 6.80-6.85 (m, 2H), 7.03-7.12 (m, 2H).

Reference Example 29

Diethyl 4,4'-dithiobis(3-nitrobenzoate)

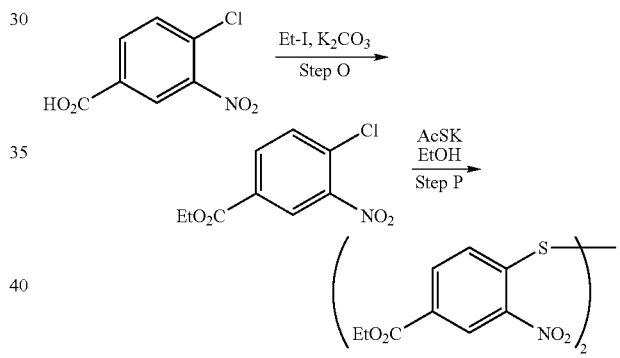

Step O

To potassium carbonate (103 g) was added DMF (1 L), and a solution of 3-nitro-4-chlorobenzoic acid (125 g) in DMF (500 ml) was added thereto under ice-cooling. Ethyl iodide (116 g) was added thereto and the resulting mixture was stirred at 60° C. for 3 hours. The reaction solution was added to a 1N aqueous hydrochloric acid solution and the crystals precipitated were collected by filtration, washed with a 1N aqueous hydrochloric acid solution and water and then dried under reduced pressure to obtain ethyl 4-chloro-3-nitrobenzoate quantitatively.

$^1$H-NMR (CDCl$_3$) δ

1.42 (t, J=7.1 Hz, 3H), 4.43 (q, J=7.1 Hz, 2H), 7.65 (d, J=8.4 Hz, 1H), 8.17 (dd, J=8.4, 2.0 Hz, 1H), 8.52 (d, J=2.0 Hz, 1H).

Step P

Ethyl 4-chloro-3-nitrobenzoate (113 g) was dissolved in ethanol (1 L) and potassium thioacetate (58.9 g) was added thereto at room temperature. The resulting mixture was stirred at 60° C. for 30 minutes and cooled to room temperature, and the crystals precipitated were collected by filtration. After the crystals were washed with ethanol and then water, acetonitrile (200 ml) was added thereto, and the resulting mixture was heated under reflux for 15 minutes. After cooling to room temperature, the crystals were collected by filtration and dried to obtain diethyl 4,4'-dithiobis(3-nitrobenzoate) (57.1 g).

$^1$H-NMR (400M, DMSO-d6) δ

1.32 (t, J=6.8 Hz, 6H), 4.35 (q, J=7.2 Hz, 4H), 8.01 (m, 2H), 8.15 (m, 2H), 8.94 (s, 2H).

Reference Example 30

Ethyl 4-{[(1S)-1-(methoxycarbonyl)-4-(4-methoxyphenyl)butyl]thio}-3-nitrobenzoate

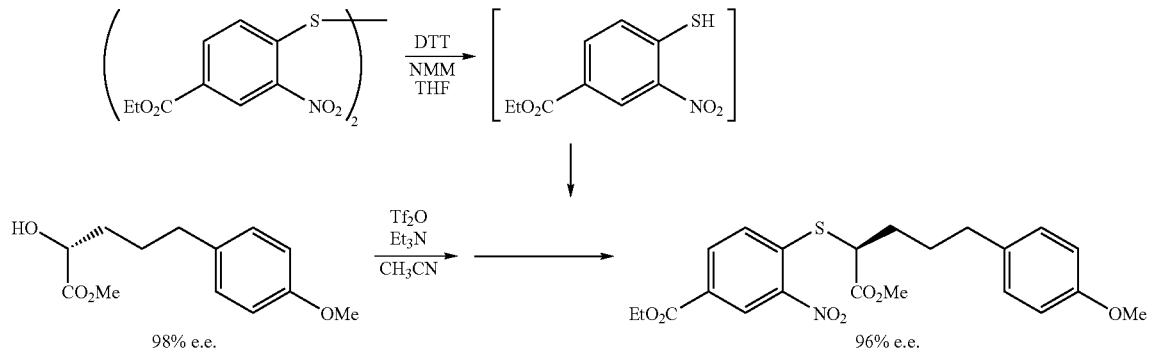

98% e.e.

96% e.e.

The methyl (2R)-2-hydroxy-5-(4-methoxyphenyl)pentanoate (10 g, 98% e.e.) synthesized in Reference Example 27 was dissolved in acetonitrile (50 mL), followed by adding trifluoromethanesulfonic acid anhydride (9 ml) and then triethylamine (6.5 ml) under ice-cooling, and the resulting mixture was stirred at the same temperature for 1 hour. A saturated aqueous ammonium chloride solution was added thereto, followed by extraction with ethyl acetate. The organic layer was washed with a saturated aqueous sodium hydrogencarbonate solution and a saturated aqueous sodium chloride solution and then dried over anhydrous sodium sulfate. The solvent was distilled off under reduced pressure and the residue was dissolved in THF (50 ml) (a solution A).

The compound of Reference Example 29 (diethyl 4,4'-dithiobis(3-nitrobenzoate)) (12.1 g) was added to THF (60 ml), and dithiothreitol (4.8 g) and then N-methylmorpholine (5.9 ml) were added thereto under a nitrogen atmosphere. The resulting mixture was stirred for 30 minutes to prepare a solution of ethyl 4-thio-3-nitrobenzoate. Although this ethyl 4-thio-3-nitrobenzoate was isolatable, the solution was used as it was in the subsequent reaction. The solution was added dropwise to the above-mentioned THF solution A under ice-cooling and the resulting mixture was stirred at the same temperature for 30 minutes. A 1N aqueous hydrochloric acid solution (110 ml) was added thereto under ice-cooling, followed by extraction with ethyl acetate (100 ml). The organic layer was washed with a saturated aqueous sodium hydrogencarbonate solution and a saturated aqueous sodium chloride solution and then dried over anhydrous sodium sulfate. The solvent was distilled off under reduced pressure to obtain ethyl 4-{[(1S)-1-(methoxycarbonyl)-4-(4-methoxyphenyl)butyl]thio}-3-nitrobenzoate (96% e.e.). This compound was used in a subsequent step without purification. The optical purity analysis conditions are as follows:

Column: AD-H (Chiralcel, DAICEL Chemical Industries Ltd.)

Detecting wavelength (UV): 254 nm

Flow rate: 1.0 ml/min

Mobile phase=n-hexane/isopropyl alcohol/TFA=95/5/0.1

1H-NMR (CDCl$_3$) δ: 1.41 (t, J=7.1 Hz, 3H), 1.70-1.98 (m, 3H), 2.05 (m, 1H), 2.62 (m, 2H), 3.72 (s, 3H), 3.78 (s, 3H), 3.94 (t, J=7.0 Hz, 1H), 4.41 (q, J=7.1 Hz, 2H), 6.78-6.84 (m, 2H), 7.06-7.09 (m, 2H), 7.62 (d, J=8.6 Hz, 1H), 8.14 (dd, J=8.5, 1.9 Hz, 1H), 8.82 (d, J=1.9 Hz, 1H).

Reference Example 31

Ethyl (2S)-2-[3-(4-methoxyphenyl)propyl]-3-oxo-3,4-dihydro-2H-1,4-benzothiazine-6-carboxylate

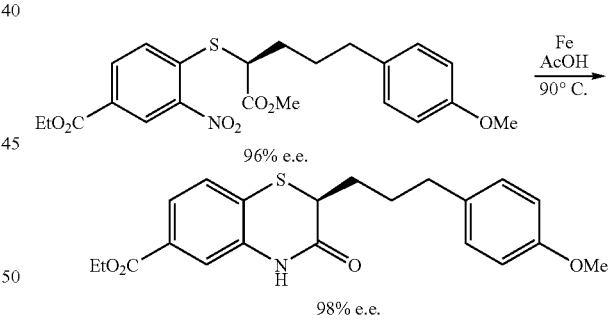

96% e.e.

98% e.e.

Acetic acid (50 ml) was added to reduced iron (8.2 g) and a solution of the compound obtained in Reference Example 30 in toluene (50 ml, the insoluble material was removed by Kiriyama filtration) was added thereto at 90° C. The resulting mixture was stirred at the same temperature for 5 hours, cooled to room temperature and then filtered through Celite. The filtrate was poured into a 1N aqueous hydrochloric acid solution (200 ml). After extraction with ethyl acetate (100 ml), the organic layer was washed with a saturated aqueous sodium chloride solution and dried over anhydrous sodium sulfate. The solvent was distilled off under reduced pressure and the residue was recrystallized from a mixed solvent of diisopropyl ether (250 ml) and ethyl acetate (50 ml) to obtain ethyl (2S)-2-[3-(4-methoxyphenyl)propyl]-3-oxo-3,4-dihydro-2H-1,4-benzothiazine-6-carboxylate (8.71 g, 98% e.e.). The optical purity was determined by the method described in Reference Example 23.

¹H-NMR (CDCl₃) δ 1.40 (t, J=7.1 Hz, 3H), 1.60-1.75 (m, 2H), 1.80-1.98 (m, 2H), 2.56 (m, 2H), 3.44 (m, 1H), 3.77 (s, 3H), 4.38 (q, J=7.1 Hz, 2H), 6.78-6.82 (m, 2H), 7.03-7.08 (m, 2H), 7.35 (d, J=8.1 Hz, 1H), 7.55 (d, J=1.5 Hz, 1H), 7.67 (dd, J=8.1, 1.5 Hz, 1H), 8.52 (s, 1H)

Reference Example 32

Ethyl (2S)-4-(2-tert-butoxy-2-oxoethyl)-2-[3-(4-methoxyphenyl)propyl]-3-oxo-3,4-dihydro-2H-1,4-benzothiazine-6-carboxylate

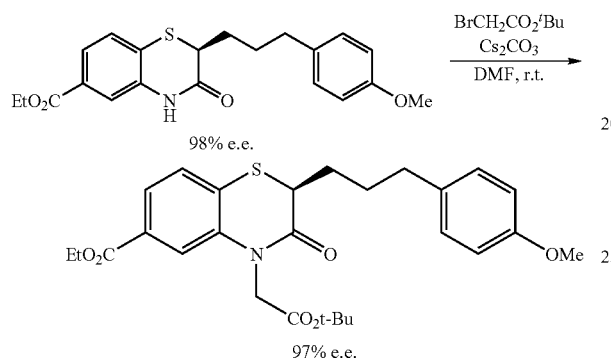

The above-mentioned product (21.7 g, 98% e.e.) was dissolved in DMF (450 ml) and cesium carbonate (18.33 g) was added thereto at 4° C. tert-Butyl bromoacetate (21.95 g) was added thereto and stirred overnight. Cesium carbonate (9.17 g) was added thereto and the resulting mixture was stirred at room temperature for 2 hours. Then, the reaction solution was poured into a saturated aqueous ammonium chloride solution under ice-cooling. After extraction with a mixed solvent of ethyl acetate (500 ml) and toluene (200 ml), the organic layer was washed with a saturated aqueous ammonium chloride solution and a saturated aqueous sodium chloride solution and then dried over anhydrous sodium sulfate. The solvent was distilled off under reduced pressure to obtain ethyl (2S)-4-(2-tert-butoxy-2-oxoethyl)-2-[3-(4-methoxyphenyl)propyl]-3-oxo-3,4-dihydro-2H-1,4-benzothiazine-6-carboxylate (97% e.e.) as a crude product. This crude product was used in a subsequent step without purification. The optical purity was determined by the method described in Reference Example 10.

¹H-NMR (CDCl₃) δ 1.38 (t, J=7.1 Hz, 3H), 1.49 (s, 9H), 1.60 (m, 1H), 1.71 (m, 1H), 1.75-1.98 (m, 2H), 2.54 (m, 2H), 3.48 (m, 1H), 3.76 (s, 3H), 4.32-4.41 (m, 3H), 4.82 (m, 1H), 6.76-6.80 (m, 2H), 7.02-7.06 (m, 2H), 7.40 (m, 1H), 7.50 (m, 1H), 7.70 (m, 1H).

Reference Example 33

Ethyl (2R)-2-hydroxy-5-(4-methoxyphenyl)pentanoate

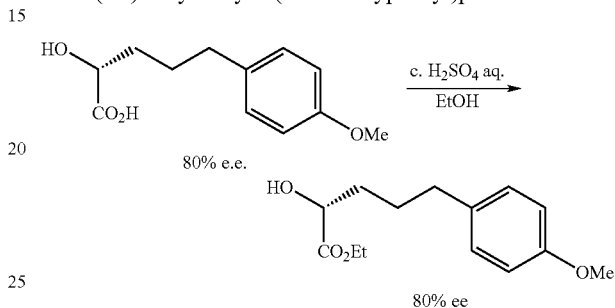

Using (2R)-2-hydroxy-5-(4-methoxyphenyl)pentanoic acid (80% e.e.), ethyl 2-hydroxy-5-(4-methoxyphenyl)pentanoate was quantitatively obtained (80% e.e.) by a process similar to the process described in Reference Example 27. The optical purity analysis conditions are as follows: Column: AD-H (Chiralcel, DAICEL Chemical Industries Ltd.)

Detecting wavelength (UV): 276 nm
Flow rate: 1.0 ml/min
Mobile phase=n-hexane/isopropyl alcohol=90/10
¹H-NMR (CDCl₃) δ
1.28 (t, J=7.1 Hz, 3H), 1.60-1.90 (m, 4H), 2.50-2.70 (m, 2H), 2.76 (m, 1H), 3.78 (s, 3H), 4.15-4.23 (m, 1H), 4.23 (q, J=7.1 Hz, 2H), 6.78-6.84 (m, 2H), 7.06-7.12 (m, 2H).

Reference Example 34

Ethyl 4-{[(1S)-1-(ethoxycarbonyl)-4-(4-methoxyphenyl)butyl]thio}-3-nitrobenzoate

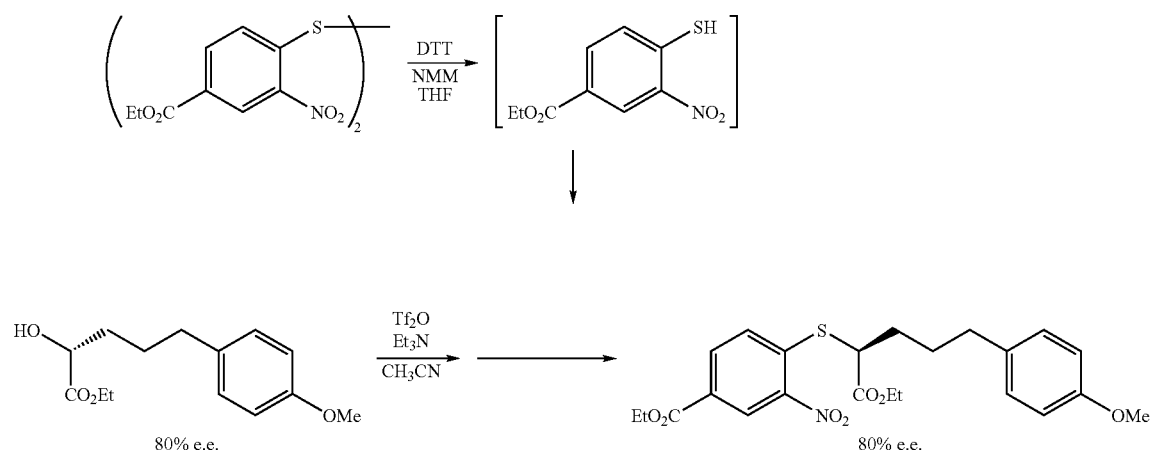

Using the ethyl (2R)-2-hydroxy-5-(4-methoxyphenyl)pentanoate (80% e.e.) described in Reference Example 33, ethyl 4-{[(1S)-1-(ethoxycarbonyl)-4-(4-methoxyphenyl)butyl]thio}-3-nitrobenzoate (80% e.e.) was obtained by a process similar to the process described in Reference Example 30. The optical purity was determined by the method described in Reference Example 30.

¹H-NMR (CDCl₃) δ

1.22 (t, J=7.1 Hz, 3H), 1.42 (t, J=7.1 Hz, 3H), 1.70-1.98 (m, 3H), 2.05 (m, 1H), 2.63 (m, 2H), 3.79 (s, 3H), 3.92 (t, J=7.0 Hz, 1H), 4.09-4.26 (m, 2H), 4.42 (q, J=7.1 Hz, 2H), 6.80-6.84 (m, 2H), 7.06-7.10 (m, 2H), 7.64 (d, J=8.6 Hz, 1H), 8.14 (dd, J=8.5, 1.9 Hz, 1H), 8.80 (d, J=1.9 Hz, 1H).

Reference Example 35

Ethyl (2S)-2-[3-(4-methoxyphenyl)propyl]-3-oxo-3,4-dihydro-2H-1,4-benzothiazine-6-carboxylate

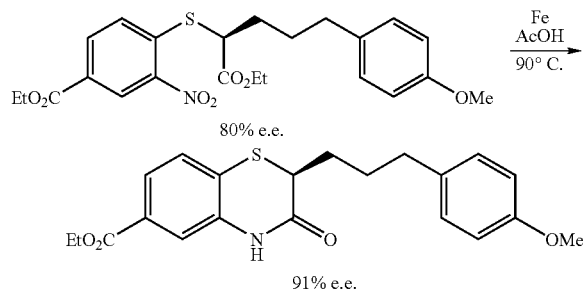

Using ethyl 4-{[(1S)-1-(ethoxycarbonyl)-4-(4-methoxyphenyl)butyl]thio}-3-nitrobenzoate (80% e.e.), ethyl (2S)-2-[3-(4-methoxyphenyl)propyl]-3-oxo-3,4-dihydro-2H-1,4-benzothiazine-6-carboxylate was quantitatively obtained (91% e.e.) by a process similar to the process described in Reference Example 31. The optical purity was determined by the method described in Reference Example 23.

¹H-NMR (CDCl₃) δ

1.40 (t, J=7.1 Hz, 3H), 1.60-1.75 (m, 2H), 1.80-1.98 (m, 2H), 2.56 (m, 2H), 3.44 (m, 1H), 3.77 (s, 3H), 4.38 (q, J=7.1 Hz, 2H), 6.78-6.82 (m, 2H), 7.03-7.08 (m, 2H), 7.35 (d, J=8.1 Hz, 1H), 7.55 (d, J=1.5 Hz, 1H), 7.67 (dd, J=8.1, 1.5 Hz, 1H), 8.52 (s, 1H).

Reference Example 36

(2S)-2-Hydroxy-5-(4-methoxyphenyl)pentanoic acid

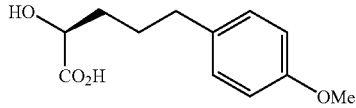

Using (S)-tolylethylamine, (2S)-2-hydroxy-5-(4-methoxyphenyl)pentanoic acid having an optical purity of 97% e.e. was obtained from the compound of Reference Example 3 as starting material by a process similar to the process described in Reference Example 4. The optical purity was determined by the method described in Reference Example 4.

¹H-NMR (CDCl₃) δ

1.66-1.92 (m, 4H), 2.61 (m, 1H), 3.78 (s, 3H), 4.26 (m, 1H), 6.80-6.85 (m, 2H), 7.03-7.12 (m, 2H).

Reference Example 37

2-Bromo-5-(4-methoxyphenyl)pentanoic acid

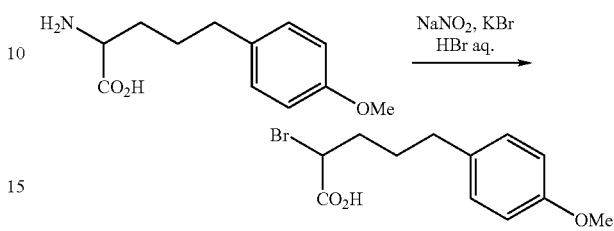

At −5° C., sodium nitrite (176 mg) was slowly added to a solution of potassium bromide (591 mg) in a 0.75M aqueous hydrobromic acid solution and then 5-(4-methylphenyl)norvaline (300 mg) was added thereto. After stirring at the same temperature for 2 hours, the reaction mixture was poured into water (50 ml) and extracted with ethyl acetate (20 ml×twice). The organic layer was collected, washed with a saturated aqueous sodium chloride solution (30 ml), dried over sodium sulfate, and then concentrated under reduced pressure. 2-Bromo-5-(4-methoxyphenyl)pentanoic acid was obtained as 355 mg of a crude product.

¹H-NMR (CDCl₃) δ

1.65-1.84 (m, 2H), 1.95-2.18 (m, 2H), 2.59-2.63 (m, 2H), 3.79 (s, 3H), 4.24 (t, J=6.8 Hz, 1H), 6.82-6.85 (m, 2H), 7.08-7.11 (m, 2H).

Reference Example 38

Ethyl 2-bromo-5-(4-methoxyphenyl)pentanoate

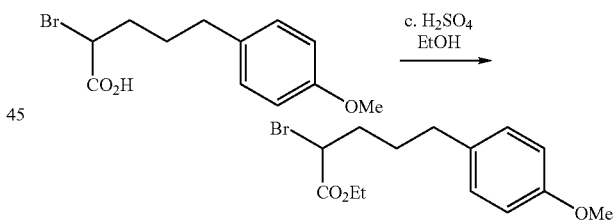

Concentrated sulfuric acid (1 ml) was added to a solution of the 2-bromo-5-(4-methoxyphenyl)pentanoic acid crude product (Reference Example 37) (1000 mg) in ethanol (15 ml) at room temperature and the resulting mixture was heated under reflux for 2 hours. After being allowed to cool to room temperature, the reaction solution was poured into water (50 ml) and extracted with ethyl acetate (50 ml). The organic layer was washed with a saturated aqueous sodium hydrogencarbonate solution (30 ml) and a saturated aqueous sodium chloride solution (30 ml) and then dried over sodium sulfate. The dried organic layer was concentrated under reduced pressure and the crude product thus obtained was purified by HPLC to obtain ethyl 2-bromo-5-(4-methoxyphenyl)pentanoate (740 mg).

¹H-NMR (CDCl₃) δ

1.59-1.81 (m, 2H), 1.95-2.15 (m, 2H), 2.58-2.62 (m, 2H), 3.79 (s, 3H), 4.18-4.25 (m, 3H), 6.81-6.85 (m, 2H), 7.07-7.10 (m, 2H).

Reference Example 39

Methyl 2-bromo-5-(4-methoxyphenyl)pentanoate

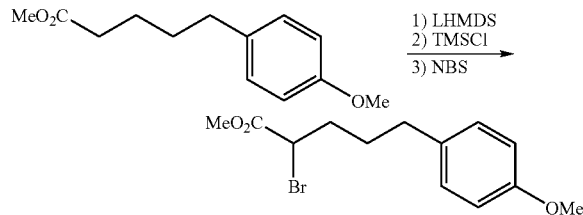

To a solution of methyl 5-(4-methoxyphenyl)pentanoate (Reference Example 18) (100 mg) in tetrahydrofuran (5 ml) was added LHMDS (1.0M in THF, 0.54 ml) at −78° C. under a nitrogen atmosphere. After stirring at the same temperature for 1 hour, TMSCl (63 μl) was added thereto and the resulting mixture was stirred for 50 minutes and then stirred at room temperature for another 10 minutes. The reaction mixture was concentrated under reduced pressure and hexane (10 ml) was added thereto. After the precipitate was filtered off, the filtrate was concentrated under reduced pressure again. To the resulting residue was added dimethylformamide (5 ml), followed by adding NBS (97 mg) at −78° C., and the resulting mixture was allowed to warm to room temperature spontaneously. The reaction mixture was poured into water (20 ml) and extracted with ethyl acetate (20 ml). The organic layer was washed with a saturated aqueous sodium chloride solution (20 ml) and then dried over sodium sulfate. The dried organic layer was concentrated under reduced pressure and the crude product thus obtained was purified by a column chromatography (hexane:ethyl acetate=5:1) to obtain methyl 2-bromo-5-(4-methoxyphenyl)pentanoate (34.2 mg).

$^1$H-NMR (CDCl$_3$) δ
1.58-1.68 (m, 1H), 1.72-183 (m, 1H), 1.99-2.12 (m, 2H), 2.54-2.63 (m, 2H), 3.77 (s, 3H), 3.78 (s, 3H), 4.22 (dd, 1H, J=7.8, 6.9 Hz), 6.81-6.85 (m, 2H), 7.06-7.12 (m, 2H).

Reference Example 40

Diethyl 4,4'-dithiobis(3-nitrobenzoate)

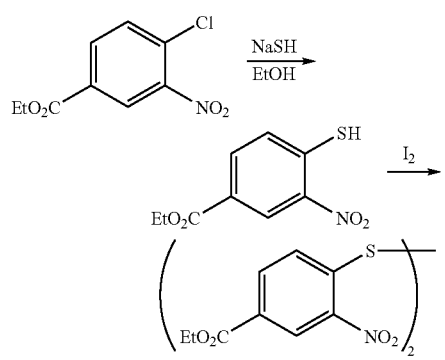

Under a nitrogen atmosphere, ethyl 4-chloro-3-nitrobenzoate (60.00 g) was suspended in ethanol (300 ml) and NaSH nH$_2$O (c.a. 70 wt %, 21.94 g) was added thereto under ice-cooling. After 30 minutes, the resulting mixture was stirred for 1 hour on a water bath at 20° C. to obtain ethyl 4-thio-3-nitrobenzoate. An aqueous solution (water 780 ml) of NaHCO$_3$ (60.00 g) and then iodine (33.16 g) were added to the ethyl 4-thio-3-nitrobenzoate and stirred for 1 hour. The crystals in the reaction mixture in the form of a homogeneous yellow slurry were filtered. After the crystals were washed with ethanol/water (1/1 (v/v), 200 ml), acetonitrile (200 ml) was added to the crystals and the resulting mixture was heated under reflux for 15 minutes. After this mixture was cooled to room temperature and stirred for 2 hours, the crystals were filtered and then washed with acetonitrile/water (1/1 (v/v), 200 ml). Water (400 ml) was added to the crystals and stirred. Thereafter, the crystals were filtered, washed with water (200 ml) and then dried to obtain diethyl 4,4'-dithiobis(3-nitrobenzoate) (50.95 g).

$^1$H-NMR (400M, DMSO-d6) δ
1.32 (t, J=6.8 Hz, 6H), 4.35 (q, J=7.2 Hz, 4H), 8.01 (m, 2H), 8.15 (m, 2H), 8.94 (s, 2H).

Reference Example 41

Ethyl 4-thio-3-nitrobenzoate

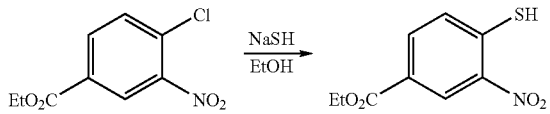

Under a nitrogen atmosphere, ethyl 4-chloro-3-nitrobenzoate (1.00 g) was suspended in ethanol (10 ml) and NaSH nH$_2$O (c.a. 70 wt %, 0.34 g) was added thereto under ice-cooling. After 30 minutes, the resulting mixture was stirred for 1 hour on a water bath at 20° C. The ethanol was concentrated to one-half of its original volume and then water was added to the residual reaction mixture, followed by extraction with toluene. The organic layer was concentrated under reduced pressure to obtain ethyl 4-thio-3-nitrobenzoate (1.00 g).

$^1$H-NMR (400M, DMSO-d6) δ
1.34 (t, J=7.1 Hz, 3H), 4.35 (q, J=7.1 Hz, 2H), 7.94 (m, 1H), 8.06 (m, 1H), 8.61 (s, 1H).

Reference Example 42

Ethyl 4-thio-3-nitrobenzoate

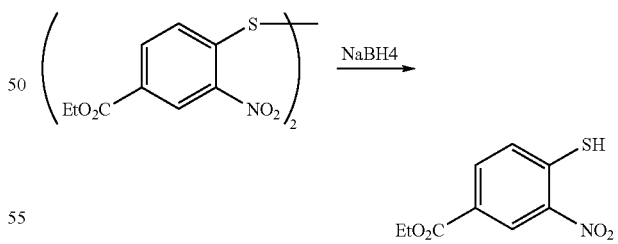

Under a nitrogen atmosphere, diethyl 4,4'-dithiobis(3-nitrobenzoate) (22.8 g) was suspended in ethanol (151 ml), and sodium tetrahydroborate (4.79 g) was added thereto in small portions under ice-cooling and stirred for 1 hour. A 1N aqueous hydrochloric acid solution (554 ml) was added to the reaction mixture under ice-cooling, followed by extraction with toluene (228 ml×2). The organic layer was washed with water (114 ml) and then distilled under reduced pressure to remove the solvent, whereby ethyl 4-thio-3-nitrobenzoate was quantitatively obtained as yellow needles.

Reference Example 43

Ethyl 4-{[(1S)-1-(methoxycarbonyl)-4-(4-methoxyphenyl)butyl]thio}-3-nitrobenzoate

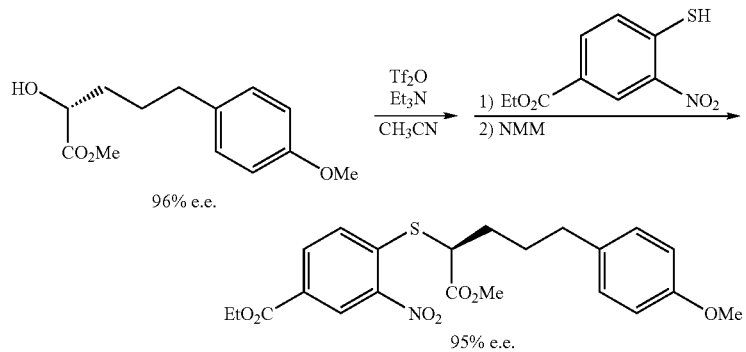

The methyl (2R)-2-hydroxy-5-(4-methoxyphenyl)pentanoate (20.0 g, 96% e.e.) synthesized in Reference Example 27 was dissolved in acetonitrile (100 ml), followed by adding thereto trifluoromethanesulfonic acid anhydride (17 ml) and then triethylamine (12.3 ml) under ice-cooling, and the resulting mixture was stirred at the same temperature for 1 hour. Water (200 ml) was added thereto under ice-cooling, followed by extraction with toluene (200 ml×2). The organic layer was washed with water (200 ml), a saturated aqueous sodium hydrogencarbonate solution (200 ml) and water (200 ml) and then distilled under reduced pressure to remove the solvent. The brown oil thus obtained was dissolved in THF (50 ml) (a solution A).

A solution of the compound obtained in Reference Example 41 or Reference Example 42 (ethyl 4-thio-3-nitrobenzoate) (22.8 g) in THF (50 ml) was added dropwise to the above-mentioned THF solution A under ice cooling. A solution of N-methylmorpholine (11.1 ml) in THF (120 ml) was slowly added dropwise to the reaction mixture while paying attention to heat generation, and the resulting mixture was stirred at the same temperature for 30 minutes. A 1N aqueous hydrochloric acid solution (220 ml) was added thereto under ice-cooling, followed by extraction with toluene (220 ml×2). The organic layer was washed with water (220 ml), a saturated aqueous sodium hydrogencarbonate solution (110 ml×2) and water (110 ml×2) and then distilled under reduced pressure to remove the solvent, whereby ethyl 4-{[(1S)-1-(methoxycarbonyl)-4-(4-methoxyphenyl)butyl]thio}-3-nitrobenzoate (95% e.e.) was obtained. This compound was used in a subsequent step without purification. The optical purity was determined by the method described in Reference Example 30.

Formulation Example 1

Tablets

| | |
|---|---|
| (−)-Ethyl 4-[2-(hydroxyamino)-2-oxoethyl]-2-[3-(4-methoxyphenyl)propyl]-3-oxo-3,4-dihydro-2H-1,4-benzothiazine-6-carboxylate | 50 mg |
| Lactose | 93 mg |
| Corn starch | 40 mg |
| Hydroxypropylmethyl cellulose 2910 | 6 mg |
| Carmelose calcium | 10 mg |
| Magnesium stearate | 1 mg |

The above ingredients were mixed each in an amount of 100 times the amount specified above, and 200 mg of the resulting mixed powder was compressed at a pressure of 50 kgf with a hydraulic press (mfd. by Riken Co. Ltd.) to obtain 100 tablets having a diameter of 8 mm and a weight of 200 mg.

Formulation Example 2

Capsules

| | |
|---|---|
| (−)-Ethyl 4-[2-(hydroxyamino)-2-oxoethyl]-2-[3-(4-methoxyphenyl)propyl]-3-oxo-3,4-dihydro-2H-1,4-benzothiazine-6-carboxylate | 100 mg |
| Lactose | 100 mg |
| Corn starch | 39 mg |
| Carmelose calcium | 10 mg |
| Magnesium stearate | 1 mg |

The above ingredients were mixed each in an amount of 100 times the amount specified above, and the resulting mixed powder was packed in capsules of No. 2 to obtain 100 capsules each having 250 mg of the contents.

Formulation Example 3

Injection

| | |
|---|---|
| (−)-4-[2-(Hydroxyamino)-2-oxoethyl]-2-[3-(4-methoxyphenyl)propyl]-3-oxo-3,4-dihydro-2H-1,4-benzothiazine-6-carboxylic acid | 50 mg |
| N-methylglucamine | 23 mg |
| Sodium chloride | 22.5 mg |
| Water for injection | 2404 mg |

N-methylglucamine (23 mg) and sodium chloride (22.5 mg) were mixed with (−)-4-[2-(hydroxyamino)-2-oxoethyl]-2-[3-(4-methoxyphenyl)propyl]-3-oxo-3,4-dihydro-2H-1,4-benzothiazine-6-carboxylic acid (50 mg), and water for injection was added thereto to carry out an adjustment. The liquid thus obtained was filled into a vial to obtain an intra-articular injection.

Test Example 1

Oral Absorbability Evaluation Test

Each of the compounds of Example 7 and Example 14 was orally administered to each of Crj:CD (SD) strain male rats (Charles River Japan Inc.) aged 7 weeks in a dose of 30 mg/kg without fasting.

Blood was collected from each rat under etherisation 15 and 30 minutes and 1, 2, 4, 6 and 24 hours after the administration, and serum was obtained from the blood and stored at −20° C. or lower till analysis. To 50 µl of the serum was added 125 µl of methanol, and stirred, followed by centrifugation (10000 rpm, 2 minutes, 4° C.). To the supernatant was added an equal volume of a 10 mM aqueous ammonium acetate solution and the resulting mixture was subjected to centrifugal filtration through Centricut (W-MR, Kurabo Industries Ltd.). Then, 10 µl of the filtrate was analyzed by LC-MS/MS. The result is shown in FIG. 1.

As a result, the bioavailability (BA) in the case of orally administering the compound of Example 7 was found to be 18.4%. Thus, it was confirmed that the compound of Example 7 is a prodrug having a superior oral absorbability as compared with the oral administration of the compound of Example 14 (bioavailability: 2.7%).

Test Example 2

Inhibitory Activity against MMP-13

As MMP-13, there was used one which had been prepared by genetic engineering (using a well-known human chondrocyte cDNA library as a template, cDNA fragments were amplified by PCR by the use of primers 5'-AATAAGCTTC-CACCATGCATCCAGGGGTCCTGGC-3' (SEQ ID NO: 1) and 5'-CCGCTCGAGTTACCCCAAATGCTCTTCAGG-3' (SEQ ID NO: 2) and each of the cDNA fragments amplified was inserted in a vector pcDNA I, and the vector was introduced into COS-1 cells derived from Afurikamidorizaru kidney, followed by culture and the recovery of the supernatant of a culture medium) on the basis of the well-known genetic base sequence of human MMP-13. (J. Biol. Chem., 269 (24), 16766-16773 (1994)) and had been activated by maintaining the thus prepared MMP-13 at 37° C. for 2 hours in the presence of 1 mM mercury 4-aminophenylacetate.

Inhibitory activity against human MMP-13 was measured according to the method of C. G. Knight et al. (FEBS Lett., 296 (3), 263-266 (1992)).

That is, 45 µl of assay buffer (0.1M Tris-hydrochloric acid, 0.1M sodium chloride, 0.01M calcium chloride, 0.05% Brigy 35, pH=7.5) was placed in a 96-well micro-titer plate for fluorometry, and 5 µl of a solution of a test compound in dimethyl sulfoxide was added thereto. Then, 25 µl of the activated human MMP-13 and 25 µl of a substrate solution obtained by diluting a 1 mM solution of (7-methoxycoumarin-4-yl)acetyl-L-prolyl-L-leucyl-glycyl-L-leucyl-L-[N-(2,4-dinitrophenyl)-L-2,3-diaminopropiony]-L-alanyl-L-argininamide (MCA; SEQ ID NO: 3) (mfd. by Peptide Laboratories Co., Ltd.) in dimethyl sulfoxide to a concentration of 80 µM with the assay buffer were added thereto, and fluorescence (ex. 320 nm, em. 405 nm) was measured with a fluorescence plate reader. After the micro-titer plate was maintained at 37° C. for 12 hours to carry out the reaction, fluorescence was measured with the fluorescence plate reader to measure the residual enzyme activity. The inhibitory activity against MMP-13 of the compound of Example 14 was 44 nM as IC50 value.

Test Example 3

Pharmacological Test on Rat Partial-Meniscectomy Models

SD (IGS) male rats aged 6 weeks (purchased from Charles River Japan Inc.) were used. The hair on the knee joint portion of right hind leg of each rat was shaved with a hair clipper under etherisation, and then the skin on the joint side of the lateral collateral ligament was incised along the ligament. Subsequently, the fascia was incised and the lateral collateral ligament was resected in a length of about 3 mm. Thereafter, the medial meniscus was exposed and the matters adhering to the meniscus were removed. The meniscus was picked up with tweezers and a part of the meniscus was cut off along the tweezers with microscissors. The fascia and the skin were sutured. One week after the above treatment, the administration of each test compound was started. The volume of the test compound administered was 10 ml/kg (solvent: 0.5% methyl cellulose) and the test compound was orally administered six times per week for 3 weeks. After the body weight was measured, the shinbone of the right hind leg was collected and fixed in 10% neutral buffered formalin. A paraffin section was prepared as a preparation. The shinbone was embedded in paraffin at first and then sliced in a thickness of 6 µm, and the slice was stained with safranine O/Fast Green. A portion of the shinbone used for preparing the preparation was a portion 3 mm apart from the front where degeneration was most remarkable when visually observed after the fixation in formalin. Evaluation was carried out as follows by taking the decrease of the stainability of proteoglycan as an indication of chondrodegeneration. The cartilage portion inside the shinbone was divided into 9 portions as shown in the following drawing and the decrease of the stainability of proteoglycan in each portion is given a score in a blind test. The highest score of each portion was taken as 1 and evaluation was expressed by numeral values on the basis of the percentage of decrease in the stainability (for example, a score of 0.25 in the case where the stainability was decreased in one-fourth of the portion). The total score of the 9 portions was taken as the score (0 to 9) of the preparation. The average of scores for rats in each group was calculated and the degree of chondrodegeneration of a pathosis control group was taken as 100%. The chondrodegeneration inhibition rate of each compound was calculated by the following equation:

Inhibition rate=1−(average score value of drug-treated group/score value of control group)×100

As a result, the compound of Example 7 showed a chondrodegeneration inhibition rate of 52% at 50 mg/kg, indicating that the compound of the present invention has an excellent pharmacological action on arthrosis deformans.

INDUSTRIAL APPLICABILITY

Owing to the present invention, it has become possible to provide a novel benzothiazin-3-one compound useful as the active ingredient of a medicine. That is, since the compound of the present invention exhibits a good oral absorbability and is metabolized in a living body to give a compound having an excellent inhibitory activity against matrix metalloproteases, it is useful as a therapeutic or preventive agent for arthrosis deformans, chondrodegenerative diseases such as chronic articular rheumatism, the metastasis of cancerous cells, and the like or as an anti-inflammatory agent and the like. In addition, it has become possible to produce a 2-thiocarboxylic acid derivative or an optically active 2-hydroxycarboxylic acid, which is an intermediate for producing the above-mentioned benzothiazin-3-one compound in high yield.

Sequence Listing Free Text

SEQ ID NO: 1: a PCR primer

SEQ ID NO: 2: another PCR primer

SEQ ID NO: 3: a synthetic peptide

The invention claimed is:

1. A benzothiazin-3-one compound represented by the formula (1):

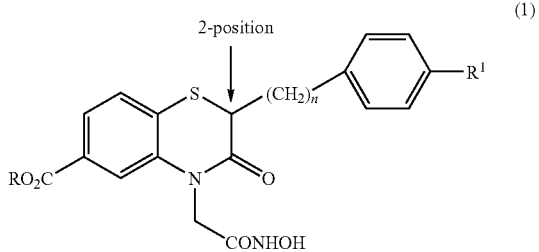

(1)

wherein n is 3 or 4; R is an ethyl group or a hydrogen atom; and $R^1$ is a halogen atom, an alkoxy group, a haloalkyl group or a haloalkoxy group, or a pharmaceutically acceptable salt thereof.

2. A benzothiazin-3-one compound or a pharmaceutically acceptable salt thereof according to claim 1, wherein in the formula (1), $R^1$ is a fluorine atom, a chlorine atom, a methoxy group, a trifluoromethyl group or a trifluoromethoxy group.

3. A benzothiazin-3-one compound or a pharmaceutically acceptable salt thereof according to claim 1, wherein in the formula (I), the configuration relating to the carbon atom at the 2-position is an S-configuration.

4. A benzothiazin-3-one compound or a pharmaceutically acceptable salt thereof according to claim 1, wherein R is an ethyl group.

5. A benzothiazin-3-one compound or a pharmaceutically acceptable salt thereof according to claim 1, wherein R is a hydrogen atom.

6. A compound or a pharmaceutically acceptable salt thereof according to claim 1, wherein the compound represented by the formula (1) is (−)-ethyl 4-[2-(hydroxyamino)-2-oxoethyl]-2-[3-(4-methoxyphenyl)propyl]-3-oxo-3,4-dihydro-2H-1,4-benzothiazine-6-carboxylate.

7. A compound or a pharmaceutically acceptable salt thereof according to claim 1, wherein the compound represented by the formula (1) is (−)-4-[2-(hydroxyamino)-2-oxoethyl]-2-[3-(4-methoxyphenyl)propyl]-3-oxo-3,4-dihydro-2H-1,4-benzothiazine-6-carboxylic acid.

8. A pharmaceutical composition comprising a benzothiazin-3-one compound or a pharmaceutically acceptable salt thereof according to claim 1 as an active ingredient.

* * * * *